US008101585B2

(12) United States Patent
Yu et al.

(10) Patent No.: US 8,101,585 B2
(45) Date of Patent: Jan. 24, 2012

(54) COMPOSITIONS AND METHODS FOR THE MODULATION OF JNK PROTEINS

(75) Inventors: Xing-Xian Yu, San Diego, CA (US); Sanjay Bhanot, Carlsbad, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 11/834,672

(22) Filed: Aug. 6, 2007

(65) Prior Publication Data

US 2008/0255030 A1 Oct. 16, 2008

Related U.S. Application Data

(60) Provisional application No. 60/835,822, filed on Aug. 4, 2006.

(51) Int. Cl.
*C07H 21/02* (2006.01)
*C07H 21/04* (2006.01)
*A61K 31/70* (2006.01)

(52) U.S. Cl. ..... 514/44; 536/23.1; 536/24.3; 536/24.33; 536/24.5

(58) Field of Classification Search ................. 536/23.1, 536/24.3, 24.33, 24.5; 514/44
See application file for complete search history.

(56) References Cited

U.S. PATENT DOCUMENTS

| | | |
|---|---|---|
| 4,689,320 A | 8/1987 | Kaji |
| 4,835,263 A | 5/1989 | Nguyen et al. |
| 4,981,957 A | 1/1991 | Lebleu et al. |
| 5,004,810 A | 4/1991 | Draper |
| 5,087,617 A | 2/1992 | Smith |
| 5,098,890 A | 3/1992 | Gewirtz et al. |
| 5,118,800 A | 6/1992 | Smith et al. |
| 5,135,917 A | 8/1992 | Burch |
| 5,138,045 A | 8/1992 | Cook et al. |
| 5,166,195 A | 11/1992 | Ecker |
| 5,194,428 A | 3/1993 | Agrawal et al. |
| 5,212,295 A | 5/1993 | Cook |
| 5,218,105 A | 6/1993 | Cook et al. |
| 5,242,906 A | 9/1993 | Pagano et al. |
| 5,264,423 A | 11/1993 | Cohen et al. |
| 5,276,019 A | 1/1994 | Cohen et al. |
| 5,286,717 A | 2/1994 | Cohen et al. |
| 5,319,080 A | 6/1994 | Leumann |
| 5,359,044 A | 10/1994 | Cook et al. |
| 5,393,878 A | 2/1995 | Leumann |
| 5,446,137 A | 8/1995 | Maag et al. |
| 5,446,786 A | 8/1995 | Shtulman |
| 5,459,255 A | 10/1995 | Cook et al. |
| 5,514,785 A | 5/1996 | Van Ness et al. |
| 5,519,134 A | 5/1996 | Acevedo et al. |
| 5,521,302 A | 5/1996 | Cook et al. |
| 5,539,082 A | 7/1996 | Nielsen et al. |
| 5,539,083 A | 7/1996 | Cook et al. |
| 5,567,811 A | 10/1996 | Misiura et al. |
| 5,576,427 A | 11/1996 | Cook et al. |
| 5,578,718 A | 11/1996 | Cook et al. |
| 5,587,361 A | 12/1996 | Cook et al. |
| 5,591,722 A | 1/1997 | Montgomery et al. |
| 5,597,909 A | 1/1997 | Urdea et al. |
| 5,610,300 A | 3/1997 | Altmann et al. |
| 5,627,053 A | 5/1997 | Usman et al. |
| 5,639,873 A | 6/1997 | Barascut et al. |
| 5,646,265 A | 7/1997 | McGee |
| 5,658,873 A | 8/1997 | Bertsch-Frank et al. |
| 5,670,633 A | 9/1997 | Cook et al. |
| 5,700,920 A | 12/1997 | Altmann et al. |
| 5,801,154 A | 9/1998 | Baracchini et al. |
| 6,133,246 A | 10/2000 | McKay et al. |
| 6,221,850 B1 * | 4/2001 | McKay et al. ................. 514/44 |
| 6,262,241 B1 | 7/2001 | Cook et al. |
| 6,582,908 B2 | 6/2003 | Fodor et al. |
| 2001/0053519 A1 | 12/2001 | Fodor et al. |
| 2003/0228597 A1 | 12/2003 | Cowsert et al. |
| 2007/0031844 A1 | 2/2007 | Khvorova et al. |

FOREIGN PATENT DOCUMENTS

| | | |
|---|---|---|
| WO | WO 93/24510 | 12/1993 |
| WO | WO 96/32496 | 10/1996 |
| WO | WO 96/34008 | 10/1996 |

OTHER PUBLICATIONS

Bogoyevitch, M. (BioEssays, 2006 vol. 28:923-934).*
Wierzbicki, AS (Expert Opinion in Pharmacotherapy, 2001 vol. 2(5):819-830).*
Khoi et al. (Journal of Gastrointestinal Surgery, 2003 vol. 7:857-863).*
International Preliminary Report on Patentability mailed Feb. 19, 2009, in International Application No. PCT/US2007/075301.
Schattenberg et al., "JNK1 but not JNK 2 promotes the development of steatohepatitis in mice," *Hepatology* 43:163-172 (2006).
Alahari et al., "The fission yeast prp4+ gene involved in pre-mRNA splicing codes for a predicted serine/threonine kinase and is essential for growth" *Nucl. Acids Res.* (1993) 21:4079-4083.
Albert et al., "Antisense knockouts: molecular scalpels for the dissection of signal transduction." Trends Pharmacol. Sci. (1994) 15:250.
Angel et al., "Oncogene jun encodes a sequence-specific trans-activator similar to AP-1" Nature (1988) 332:166-171.
Berge et al., "Pharmaceutical Salts" J. of Pharma Sci. (1977) 66:1.
Biedler et al., "Morphology and growth, tumorigenicity, and cytogenetics of human neuroblastoma cells in continuous culture." Cancer Res. (1973) 33:2643-2652.
Binetruy et al., "Ha-Ras augments c-Jun activity and stimulates phosphorylation of its activation domain" Nature (1991) 351:122-127.
Bohmann et al., "Human proto-oncogene c-jun encondes a DNA binding protein with structural and functional properties of transcription factor AP-1" Science (1987) 238:1386.
Brigstock et al., "Species-specific high molecular weight forms of basic fibroblast growth factor" Growth Factors (1990) 4:45.
Cano et al., "Parallel signal processing among mammalian MAPKs" Trends Biochem. Sci. (1995) 20:117.

(Continued)

*Primary Examiner* — Terra Cotta Gibbs
(74) *Attorney, Agent, or Firm* — Jones Day

(57) ABSTRACT

The invention provides compositions and methods for the treatment and diagnosis of diseases or disorders amenable to treatment through modulation of expression of a gene encoding a Jun N-terminal kinase 1 (JNK1 protein.

30 Claims, No Drawings

OTHER PUBLICATIONS

Cheng et al., "Bidirectional regulation of p38 kinase and c-Jun N-terminal protein kinase by insulin-like growth factor-1" J. Biol. Chem. (1998) 273(23):14560-5.

Cioffi et al., "Selective inhibition of A-Raf and C-Raf mRNA expression by antisense oligodeoxynucleotides in rat vascular smooth muscle cells: role of A-Raf and C-Raf in serum-induced proliferation" Mol. Pharmacol. (1997) 51:383-9.

Cobb et al., "How MAP kinases are regulated" J. Biol. Chem (1995) 270:14843-6.

Crooke et al., Exp. Opin. Ther. Patents (1996) 6:855.

Crooke et al., "Pharmacokinetic properties of several novel oligonucleotide analogs in mice" J. Pharmacol. Exp. Ther. (1996) 277:923-37.

Derijard et al., "JNK1: a protein kinase stimulated by UV light and Ha-Ras that binds and phosphorylates the c-Jun activation domain" Cell (1994) 76:1025.

Dean et al., "Inhibition of protein kinase C-alpha expression in mice after systemic administration of phosphorothioate antisense oligodeoxynucleotides" Proc. Natl. Acad. Sci. USA (1994) 91:11762-6.

Devirgilio et al. "Cloning and disruption of a gene required for growth on acetate but not on ethanol: The acetyl-coenzyme a synthetase gene of *Saccharmoyces cerevisiae*" Yeast (1992) 8:1043-51.

French et al., "Expression of two related nonstructural proteins of bluetongue virus (BTV) type 10 in insect cells by a recombinant baculovirus: production of polyclonal ascitic fluid and characterization of the gene product in BTV-infected BHK cells" J. Virol. (1989) 63:3270-8.

Gao et al., "Cloning and characterization of a mouse gene with homology to the human von Hippel-Lindau disease tumor suppressor gene: implications for the potential organization of the human von Hippel-Lindau disease gene." Cancer Res. (1995) 55:743-7.

Gebeyehu, G. et al., "Novel biotinylated nucleotide—analogs for labeling and colorimetric detection of DNA." Nucleic Acids Res. (1987) 15:4513-34.

Gelbert et al. "Analysis of GPT activity in mammalian cells with a chromosomally integrated shuttle vector containing altered gpt genes." Somat. Cell. Mol. Genet. (1990) 16:173-84.

Gupta et al., "Selective interaction of JNK protein kinase isoforms with transcription factors." EMBO Journal (1996) 15:2760-70.

Hibi et al., "Identification of an oncoprotein- and UV-responsive protein kinase that binds and potentiates the c-Jun activation domain" Genes & Dev. (1993) 7:2135-48.

Hirosumi et al., "A central role for JNK in obesity and insulin resistance" Nature (2002) 420:333-336.

International Search Report for PCT/US07/75301 dated Nov. 16, 2007 (DIBIS-0089WO).

Jalava et al., "Effects of bryostatins 1 and 2 on morphological and functional differentiation of SH-SY5Y human neuroblastoma cells." Cancer Res. (1990) 50:3422-8.

Kabanov et al., "A new class of antivirals: antisense oligonucleotides combined with a hydrophobic substituent effectively inhibit influenza virus reproduction and synthesis of virus-specific proteins in MDCK cells." FEBS Lett. (1990) 259:327-30.

Kallunki et al., "JNK2 contains a specificity-determining region responsible for efficient c-Jun binding and phosphorylation." Genes & Development (1994) 8:2996-3007.

Kanagasundaram et al., "Isolation and characterization of the gene encoding gluconolactonase from Zymomonas mobilis." Biochim. Biophys. Acta (1992) 1171:198-200.

Kyriakis et al., "The stress-activated protein kinase subfamily of c-Jun kinases." Nature (1994) 369:156-160.

Letsinger et al., "Cholesteryl-conjugated oligonucleotides: synthesis, properties, and activity as inhibitors of replication of human immunodeficiency virus in cell culture." Proc. Natl. Acad. Sci. USA (1989) 86:6553-6.

Manoharan et al., "Chemical modifications to improve uptake and bioavailability of antisense oligonucleotides." Ann. N. Y. Acad. Sci (1992) 660:306-9.

Manoharan et al., Bioorg Med. Chem. Let. (1993) 3:2765.

Manoharan et al., Bioorg. Med. Chem. Let. (1994) 4:1053.

Manoharan et al., Tetrahedron Lett. (1995) 36:3651.

Manoharan et al., Nucleosides & Nucleotides (1995) 14:969.

Markussen et al., "Translational control of oskar generates short OSK, the isoform that induces pole plasma assembly." Development (1995) 121:3723-32.

Martin et al., Helv. Chim. Acta (1995) 78:486-504.

Martin et al., "Developmental expression in the mouse nervous system of the p493F12 SAP kinase." Brain Res. Mol. Brain Res. (1996) 35:47-57.

McDermott et al., "Structure and lens expression of the gene encoding chicken beta A3/A1-crystallin." Gene (1992) 117:193-200.

Mishra et al., "Improved leishmanicidal effect of phosphorotioate antisense oligonucleotides by LDL-mediated delivery." Biochim. Biophys. Acta (1995) 1264:229-37.

Mohit et al., "p493F12 kinase: a novel MAP kinase expressed in a subset of neurons in the human nervous system" Neuron (1994) 14:67-78.

Monaco et al., "Structure of two rat genes coding for closely related rolipram-sensitive cAMP phosphodiesterases. Multiple mRNA variants originate from alternative splicing and multiple start sites." J.Biol. Chem. (1994) 269:347-57.

Oberhauser et al., "Effective incorporation of 2'-O-methyl-oligoribonucleotides into liposomes and enhanced cell association through modification with thiocholesterol." Nucl. Acids Res. (1992) 20:533-8.

Olsen et al., "Inhibition of protein kinase-A by overexpression of the cloned human protein kinase inhibitor." Mol Endocrinol. (1991) 5:1246-56.

Perri et al., "Interactions of plasmid-encoded replication initiation proteins with the origin of DNA replication in the broad host range plasmid RK2." J. Biol. Chem (1991) 266:12536-43.

Pushpa-Rekha et al., "Rat phospholipid-hydroperoxide glutathione peroxidase. cDNA cloning and identification of multiple transcription and translation start sites." J. Biol. Chem. (1995) 270:26993-9.

Nielsen et al., "Sequence-selective recognition of DNA by strand displacement with a thymine-substituted polyamide." Science (1991) 254:1497-1500.

Rogers et al., "Alternative splicing dictates translational start in Epstein-Barr virus transcripts." EMBO J. (1990) 9:2273-7.

Saison-Behmoaras et al., "Short modified antisense oligonucleotides directed against Ha-ras point mutation induce selective cleavage of the mRNA and inhibit T24 cells proliferation." EMBO J. (1991) 10:1111-8.

Saul et al., "celB, a gene coding for a bifunctional cellulase from the extreme thermophile "Caldocellum saccharolyticum"." Appl. Environ. Microbiol. (1990) 56:3117-24.

Seger et al., "The MAPK signaling cascade." FASEB J. (1995) 9:726-35.

Shea et al., "Synthesis, hybridization properties and antiviral activity of lipid-oligodeoxynucleotide conjugates." Nucl. Acids Res. (1990) 18:3777-83.

Singleton et al., "Type I insulin-like growth factor receptor activation regulates apoptotic proteins." J. Biol. Chem (1996) 271:31791-4.

Sluss et al., "Signal transduction by tumor necrosis factor mediated by JNK protein kinases." Mol. Cell Biol. (1994) 14:8376-84.

Smeal et al., "Oncogenic and transcriptional cooperation with Ha-Ras requires phosphorylation of c-Jun on serines 63 and 73." Nature (1991) 354:494-6.

Svinarchuk et al., "Inhibition of HIV proliferation in MT-4 cells by antisense oligonucleotide conjugated to lipophilic groups." Biochimie (1993) 75:49-54.

Wahlestedt et al., "Antisense oligodeoxynucleotides to NMDA-R1 receptor channel protect cortical neurons from excitotoxicity and reduce focal ischaemic infarctions." Nature (1993) 363:260-3.

Wahlestedt et al., "Modulation of anxiety and neuropeptide Y-Y1 receptors by antisense oligodeoxynucleotides." Science (1993) 259:528-31.

Yang, Y. et al., "C-Jun NH2-terminal Kinase Mediates Proliferation and Tumor Growth of Human Prostate Carcinoma" *Clinical Caner Research* (2003) 9:391-401.

Yaoita et al., "Xenopus laevis alpha and beta thyroid hormone receptors." Proc. Natl. Acad. Sci USA (1990) 87:7090-4.

Bogoyevitch et al., "Targeting the JNK MAPK cascade for inhibition: basic science and therapeutic potential" Biochimica et Biophysica Acta—Proteins & Proteomics (2004) 1697:1-2.

Branch et al., "A good antisense molecule is hard to find," TIBS (1998) 23:45-50.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002.

Crooke et al., "Basic Principles of Antisense Therapeutics" Antisense Research and Application (1998) Chapter 1:1-50.

Gunawan et al., "c-Jun N-Terminal Kinase Plays a Major Role in Murine Acetaminophen Hepatotoxicity" Gastroenterology (2006) 131(1):165-178.

Kaneto et al., "Possible novel therapy for diabetes with cell-permeable JNK-inhibitory peptide" Nature Medicine (2004) 10(10):1128-1132.

New England Biolabs 1998/99 Catalog (cover page and pp. 121 and 284).

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

European Search Report for application EP 07840710.3 dated May 26, 2011.

* cited by examiner

COMPOSITIONS AND METHODS FOR THE MODULATION OF JNK PROTEINS

CROSS-REFERENCE TO RELATED APPLICATIONS

This application claims the benefit of U.S. provisional application Ser. No. 60/835,822 filed Aug. 4, 2006 which is incorporated herein by reference in its entirety.

SEQUENCE LISTING

The present application is being filed along with a Sequence Listing in electronic format. The Sequence Listing is provided as a file entitled BIOL0089USSEQ.txt, created on Aug. 6, 2007 which is 64 Kb in size. The information in the electronic format of the sequence listing is incorporated herein by reference in its entirety.

FIELD OF THE INVENTION

The present invention provides compositions and methods for detecting and modulating levels of Jun N-terminal kinases (JNK proteins), enzymes which are encoded by JNK genes.

BACKGROUND OF THE INVENTION

The rapid increase in the prevalence of obesity, type-2 diabetes and associated complications is a major global health problem. About two-thirds of adults in the United States are overweight, and almost one-third are obese, according to data from the National Health and Nutrition Examination Survey (NHANES) 2001 to 2004. While overweight and obesity are found worldwide, the prevalence of these conditions in the United States ranks high among developed nations. Overweight refers to an excess of body weight compared to set standards. The excess weight can come from muscle, bone, fat, and/or body water. Obesity refers specifically to having an abnormally high proportion of body fat. Individuals who are obese have a 10- to 50-percent increased risk of death from all causes, compared with healthy weight individuals. Most of the increased risk is due to cardiovascular causes. Obesity is associated with about 112,000 excess deaths per year in the U.S. population relative to healthy weight individuals. Obesity is a known risk factor for diabetes, coronary heart disease, high blood cholesterol, stroke, hypertension, gallbladder disease, osteoarthritis, sleep apnea and other breathing problems as well as some forms of cancer (breast, colorectal, endometrial, and kidney).

Diabetes is a disorder characterized by hyperglycemia due to deficient insulin action that can result from reduced insulin production or insulin resistance or both. Additionally, glucotoxicity, which results from long-term hyperglycemia, induces tissue-dependent insulin resistance exacerbating the disease. Chronic hyperglycemia is also a major risk factor for diabetes-associated complications, including heart disease, retinopathy, nephropathy and neuropathy. Diabetes and obesity, sometimes now collectively referred to as "diabesity") are interrelated in that obesity is known to exacerbate the pathology of diabetes and greater than 60% of diabetics are obese. Most human obesity is associated with insulin resistance and leptin resistance. Obesity can have an even greater impact on insulin action than diabetes itself.

Effective treatments are needed for diabetes, obesity, metabolic syndrome and other diseases and conditions associated with glucose and/or lipid metabolism and/or the disregulation thereof. The present invention satisfies this need and provides related advantages as well.

SUMMARY OF THE INVENTION

The present invention provides methods of reducing glucose levels in a subject by administering a therapeutically effective amount of an antisense compound targeted to a JNK1 nucleic acid. In a distinct embodiment, the invention also provides methods of reducing lipid levels in a subject by administering a therapeutically effective amount of an antisense compound targeted to a JNK1 nucleic acid. In a further embodiment, methods of treating metabolic syndrome in a subject by administering a therapeutically effective amount of an antisense compound targeted to a JNK1 nucleic acid also are provided by the present invention.

In additional distinct embodiments, the invention also provides methods of treating obesity, diabetes and metabolic syndrome in a subject. The methods of the invention encompass administration of a therapeutically effective amount of an antisense compound targeted to a JNK1 nucleic acid to a subject in need thereof.

The invention also provides methods of treating diabetes in a subject by administering a glucose-lowering agent and a therapeutically effective amount of an antisense compound targeted to a JNK1 nucleic acid.

In particular embodiments, the methods of treating diabetes in a subject include administering a pharmaceutical composition encompassing a glucose-lowering agent and a therapeutically effective amount of an antisense compound targeted to a JNK1 nucleic acid.

Also provided are methods of treating diabetes, diabetes and/or metabolic syndrome in a subject by administering a lipid lowering agent and a therapeutically effective amount of an antisense compound targeted to a JNK1 nucleic acid. In certain embodiments, the methods of treating diabetes in a subject include administering a pharmaceutical composition encompassing a lipid lowering agent and a therapeutically effective amount of an antisense compound targeted to a JNK1 nucleic acid.

Antisense compounds useful for practicing the claimed methods, including antisense oligonucleotides, that are complementary to SEQ ID NOS: 87, 89, 90 and 91 also are provided.

DETAILED DESCRIPTION OF THE INVENTION

Definitions

Unless defined otherwise, all technical and scientific terms used herein have the same meaning as is commonly understood by one of skill in the art to which the invention(s) belong. Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, chemical analysis, pharmaceutical preparation, formulation and delivery, and treatment of subjects. Certain such techniques and procedures can be found for example in "Carbohydrate Modifications in Antisense Research" Edited by Sangvi and Cook, American Chemical Society, Washington D.C., 1994; and "Remington's Pharmaceutical Sciences," Mack Publishing Co., Easton, Pa., 18th edition, 1990; and which is hereby incorporated by reference for any purpose.

Where permitted, all patents, patent applications, published applications and publications, GENBANK sequences, websites and other published materials referred to throughout the entire disclosure herein, unless noted otherwise, are incorporated by reference in their entirety. In the event that there is a plurality of definitions for terms herein, those in this section prevail. Where reference is made to a URL or other such identifier or address, it is understood that such identifiers can change and particular information on the internet can command go, but equivalent information can be found by searching the internet. Reference thereto evidences the availability and public dissemination of such information.

"Obesity" is defined as an excessively high amount of body fat or adipose tissue in relation to lean body mass. The amount of body fat (or adiposity) includes concern for both the distribution of fat throughout the body and the size of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese.

Insulin resistance is a condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Type 2 diabetes," (also known as diabetes mellitus type 2, and formerly called diabetes mellitus type II, non-insulin-dependent diabetes (NIDDM), obesity related diabetes, or adult-onset diabetes) is a metabolic disorder that is primarily characterized by insulin resistance, relative insulin deficiency, and hyperglycemia.

A glucose tolerance test is the administration of glucose to determine how quickly it is cleared from the blood. The test is usually used to test for diabetes, insulin resistance, and sometimes reactive hypoglycemia. The glucose is most often given orally so the common test is technically an oral glucose tolerance test (OGTT).

"Metabolic rate" refers to the amount of energy expended. Basal metabolic rate (also known as BMR) is the amount of energy expended while at rest in a neutrally temperate environment, in the post-absorptive state (meaning that the digestive system is inactive, which requires about twelve hours of fasting in humans). The release of energy in this state is sufficient only for the functioning of the vital organs, such as the heart, lungs, brain and the rest of the nervous system, liver, kidneys, sex organs, muscles and skin. BMR decreases with age and with the loss of lean body mass. Increased cardiovascular exercise and muscle mass can increase BMR. Illness, previously consumed food and beverages, environmental temperature, and stress levels can affect one's overall energy expenditure, and can affect one's BMR as revealed by gas analysis. It is measured when the person is at complete rest, but awake. An accurate BMR measurement requires that the person's sympathetic nervous system is not stimulated. Basal metabolic rate is measured under very restrictive circumstances. A more common and closely related measurement, used under less strict conditions, is resting metabolic rate (RMR). "Metabolic" and "metabolism" are terms well know in the art and generally include the whole range of biochemical processes that occur within a living organism. Metabolic disorders include, but are not limited to, hyperglycemia, pre-diabetes, diabetes (type I and type II), obesity, insulin resistance and metabolic syndrome.

As used herein, the terms "treatment" and "treating" refer to administering a composition of the invention to effect an alteration or improvement of the disease or condition. Prevention, amelioration, and/or treatment can require administration of multiple doses at regular intervals, or prior to onset of the disease or condition to alter the course of the disease or condition. Moreover, a single agent can be used in a single individual for each prevention, amelioration, and treatment of a condition or disease sequentially, or concurrently.

As used herein, the term "pharmaceutical agent," including, for example, an antisense oligonucleotide, a lipid lowering agent or a glucose lowering agent, refers to a substance provides a therapeutic benefit when administered to a subject. In certain embodiments, an antisense oligonucleotide targeted to JNK1 is a pharmaceutical agent.

"Therapeutically effective amount" means an amount of a pharmaceutical agent that provides a therapeutic benefit to a subject. In certain embodiments, a therapeutically effective amount of antisense compound targeted to a JNK1 nucleic acid is an amount that decreases LDL-C in the subject.

A "pharmaceutical composition" means a mixture of substances suitable for administering to a subject. A pharmaceutical composition can comprise, for example, a combination of antisense oligonucleotides, a combination of antisense oligonucleotides and non-antisense pharmaceutical agents as well as the presence of a sterile aqueous solution or other standard pharmaceutical additive known in the art.

"Administering" means providing a pharmaceutical agent or composition to a subject, and includes, but is not limited to administering by a medical professional and self-administering. Co-administration is the administration of two or more pharmaceutical agents to an animal. The two or more pharmaceutical agents can be in a single pharmaceutical composition, or can be in separate pharmaceutical compositions. Each of the two or more pharmaceutical agents can be administered through the same or different routes of administration. Co-administration encompasses administration in parallel, concomitant or sequentially.

As used herein, the term "subject" refers to an animal, including, but not limited to a human, to whom a pharmaceutical composition is administered. Animals include humans or non-human animal, including, but not limited to, mice, rats, rabbits, dogs, cats, pigs, and non-human primates, including, but not limited to, monkeys and chimpanzees.

"Parenteral administration," means administration through injection or infusion. Parenteral administration includes, but is not limited to, subcutaneous administration, intravenous administration, or intramuscular administration.

Duration refers to the period of time during which an activity or event continues. In certain embodiments, the duration of treatment is the period of time during which doses of a pharmaceutical agent are administered.

"Subcutaneous administration" means administration just below the skin. "Intravenous administration" means administration into a vein.

Dose means a specified quantity of a pharmaceutical agent provided in a single administration. In certain embodiments, a dose can be administered in two or more boluses, tablets, or injections. For example, in certain embodiments, where subcutaneous administration is desired, the desired dose requires a volume not easily accommodated by a single injection. In such embodiments, two or more injections can be used to achieve the desired dose. In certain embodiments, a dose can be administered in two or more injections to minimize injection site reaction in a subject. Dosage unit is the form in which a pharmaceutical agent is provided. In certain embodiments, a dosage unit is a vial containing lyophilized antisense oligonucleotide. In certain embodiments, a dosage unit is a vial containing reconstituted antisense oligonucleotide.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

As used herein, the term major risk factors refers to factors that contribute to a high risk for a particular disease or condition. In certain embodiments, major risk factors for coronary heart disease include, without limitation, cigarette smoking, hypertension, low HDL-C, family history of coronary heart disease, and age.

"CHD risk factors" mean CHD risk equivalents and major risk factors.

"Coronary heart disease (CHD)" means a narrowing of the small blood vessels that supply blood and oxygen to the heart, which is often a result of atherosclerosis.

"Reduced coronary heart disease risk" means a reduction in the likelihood that a subject will develop coronary heart disease. In certain embodiments, a reduction in coronary heart disease risk is measured by an improvement in one or more CHD risk factors, for example, a decrease in LDL-C levels.

"Atherosclerosis" means a hardening of the arteries affecting large and medium-sized arteries and is characterized by the presence of fatty deposits. The fatty deposits are called "atheromas" or "plaques," which consist mainly of cholesterol and other fats, calcium and scar tissue, and damage the linking of arteries.

"History of coronary heart disease" means the occurrence of clinically evident coronary heart disease in the medical history of a subject or a subject's family member.

"Early onset coronary heart disease" means a diagnosis of coronary heart disease prior to age 50.

"Statin intolerant individual" means a individual who as a result of statin therapy experiences one or more of creatine kinase increases, liver function test abnormalities, muscle aches, or central nervous system side effects.

"Efficacy" means the ability to produce a desired effect. For example, efficacy of a lipid-lowering therapy can be reduction in the concentration of one or more of LDL-C, VLDL-C, IDL-C, non-HDL-C, ApoB, lipoprotein(a), or triglycerides.

"Acceptable safety profile" means a pattern of side effects that is within clinically acceptable limits.

"Side effects" means physiological responses attributable to a treatment other than desired effects. In certain embodiments, side effects include, without limitation, injection site reactions, liver function test abnormalities, renal function abnormalities, liver toxicity, renal toxicity, central nervous system abnormalities, and myopathies. For example, increased aminotransferase levels in serum can indicate liver toxicity or liver function abnormality. For example, increased bilirubin can indicate liver toxicity or liver function abnormality.

"Injection site reaction" means inflammation or abnormal redness of skin at a site of injection in a subject.

"Individual compliance" means adherence to a recommended or prescribed therapy by a subject.

"Lipid-lowering therapy" means a therapeutic regimen provided to a subject to reduce one or more lipids in a subject. In certain embodiments, a lipid-lowering therapy is provide to reduce one or more of ApoB, total cholesterol, LDL-C, VLDL-C, IDL-C, non-HDL-C, triglycerides, small dense LDL particles, and Lp(a) in a subject.

"Lipid-lowering agent" means a pharmaceutical agent provided to a subject to achieve a lowering of lipids in the individual. For example, in certain embodiments, a lipid-lowering agent is provided to a subject to reduce one or more of ApoB, LDL-C, total cholesterol, and triglycerides.

"LDL-C target" means an LDL-C level that is desired following lipid-lowering therapy.

"Comply" means the adherence with a recommended therapy by a subject.

"Recommended therapy" means a therapeutic regimen recommended by a medical professional for the treatment, amelioration, or prevention of a disease.

"Low LDL-receptor activity" means LDL-receptor activity that is not sufficiently high to maintain clinically acceptable levels of LDL-C in the bloodstream.

"Cardiovascular outcome" means the occurrence of major adverse cardiovascular events.

"Improved cardiovascular outcome" means a reduction in the occurrence of major adverse cardiovascular events, or the risk thereof. Examples of major adverse cardiovascular events include, without limitation, death, reinfarction, stroke, cardiogenic shock, pulmonary edema, cardiac arrest, and atrial dysrhythmia.

"Surrogate markers of cardiovascular outcome" means indirect indicators of cardiovascular events, or the risk thereof. For example, surrogate markers of cardiovascular outcome include carotid intimal media thickness (CIMT). Another example of a surrogate marker of cardiovascular outcome includes atheroma size. Atheroma size can be determined by intravascular ultrasound (IVUS).

"Increased HDL-C" means an increase in serum HDL-C in a subject over time.

"Lipid-lowering" means a reduction in one or more serum lipids in a subject over time.

"Therapeutic lifestyle change" means dietary and lifestyle changes intended to lower cholesterol and reduce the risk of developing heart disease, and includes recommendations for dietary intake of total daily calories, total fat, saturated fat, polyunsaturated fat, monounsaturated fat, carbohydrate, protein, cholesterol, insoluble fiber, as well as recommendations for physical activity.

"Statin" means a pharmaceutical agent that inhibits the activity of HMG-CoA reductase.

"HMG-CoA reductase inhibitor" means a pharmaceutical agent that acts through the inhibition of the enzyme HMG-CoA reductase.

"Cholesterol absorption inhibitor" means a pharmaceutical agent that inhibits the absorption of exogenous cholesterol obtained from diet.

"LDL apheresis" means a form of apheresis by which LDL-C is removed from blood. Typically, a subject's blood is removed from a vein, and separated into red cells and plasma. LDL-C is filtered out of the plasma prior to return of the plasma and red blood cells to the individual.

"MTP inhibitor" means a pharmaceutical agent that inhibits the enzyme microsomal triglyceride transfer protein.

"Low density lipoprotein-cholesterol (LDL-C)" means cholesterol carried in low density lipoprotein particles. Concentration of LDL-C in serum (or plasma) is typically quantified in mg/dL or nmol/L. "Serum LDL-C" and "plasma LDL-C" mean LDL-C in the serum and plasma, respectively.

"Very low density lipoprotein-cholesterol (VLDL-C)" means cholesterol associated with very low density lipoprotein particles. Concentration of VLDL-C in serum (or plasma) is typically quantified in mg/dL or nmol/L. "Serum VLDL-C" and "plasma VLDL-C" mean VLDL-C in the serum or plasma, respectively.

"Intermediate low density lipoprotein-cholesterol (IDL-C)" means cholesterol associated with intermediate density lipoprotein. Concentration of IDL-C in serum (or plasma) is typically quantified in mg/mL or nmol/L. "Serum IDL-C" and "plasma IDL-C" mean IDL-C in the serum or plasma, respectively.

"Non-high density lipoprotein-cholesterol (Non-HDL-C)" means cholesterol associated with lipoproteins other than high density lipoproteins, and includes, without limitation, LDL-C, VLDL-C, and IDL-C.

"High density lipoprotein-C (HDL-C)" means cholesterol associated with high density lipoprotein particles. Concentration of HDL-C in serum (or plasma) is typically quantified in mg/dL or nmol/L. "Serum HDL-C" and "plasma HDL-C" mean HDL-C in the serum and plasma, respectively.

"Total cholesterol" means all types of cholesterol, including, but not limited to, LDL-C, HDL-C, IDL-C and VLDL-C. Concentration of total cholesterol in serum (or plasma) is typically quantified in mg/dL or nmol/L.

"Lipoprotein(a)" or "Lp(a)" means a lipoprotein particle that is comprised of LDL-C, an apolipoprotein(a) particle, and an apolipoproteinB-100 particle.

"ApoA1" means apolipoprotein-A1 protein in serum. Concentration of ApoA1 in serum is typically quantified in mg/dL or nmol/L.

"ApoB:ApoA1 ratio" means the ratio of ApoB concentration to ApoA1 concentration.

"ApoB-containing lipoprotein" means any lipoprotein that has apolipoprotein B as its protein component, and is understood to include LDL, VLDL, IDL, and lipoprotein(a).

"Small LDL particle" means a subclass of LDL particles characterized by a smaller, denser size compared to other LDL particles. In certain embodiments, intermediate LDL particles are 23-27 nm in diameter.

In certain embodiments, large LDL particles are 21.2-23 nm in diameter. In certain embodiments, small LDL particles are 18-21.2 nm in diameter. In certain embodiments, particle size is measured by nuclear magnetic resonance analysis.

"Small VLDL particle" means a subclass of VLDL particles characterized by a smaller, denser size compared to other VLDL particles. In certain embodiments, large VLDL particles are greater than 60 nm in diameter. In certain embodiments, medium VLDL particles are 35-60 nm in diameter. In certain embodiments, small VLDL particles are 27-35 nm in diameter. In certain embodiments, particle size is measured by nuclear magnetic resonance analysis.

"Triglycerides" means lipids that are the triesters of glycerol. "Serum triglycerides" mean triglycerides present in serum. "Liver triglycerides" mean triglycerides present in liver tissue.

"Serum lipids" mean cholesterol and triglycerides in the serum.

"Elevated total cholesterol" means total cholesterol at a concentration in a subject at which lipid-lowering therapy is recommended, and includes, without limitation, elevated LDL-C", "elevated VLDL-C," "elevated IDL-C" and "elevated non-HDL-C." In certain embodiments, total cholesterol concentrations of less than 200 mg/dL, 200-239 mg/dL, and greater than 240 mg/dL are considered desirable, borderline high, and high, respectively. In certain embodiments, LDL-C concentrations of 100 mg/dL, 100-129 mg/dL, 130-159 mg/dL, 160-189 mg/dL, and greater than 190 mg/dL are considered optimal, near optimal/above optimal, borderline high, high, and very high, respectively.

"Elevated triglyceride" means concentrations of triglyceride in the serum or liver at which lipid-lowering therapy is recommended, and includes "elevated serum triglyceride" and "elevated liver triglyceride." In certain embodiments, serum triglyceride concentration of 150-199 mg/dL, 200-499 mg/dL, and greater than or equal to 500 mg/dL is considered borderline high, high, and very high, respectively.

"Elevated small LDL particles" means a concentration of small LDL particles in a subject at which lipid-lowering therapy is recommended.

"Elevated small VLDL particles" means a concentration of small VLDL particles in a subject at which lipid-lowering therapy is recommended.

"Elevated lipoprotein(a)" means a concentration of lipoprotein(a) in a subject at which lipid-lowering therapy is recommended.

"Low HDL-C" means a concentration of HDL-C in a subject at which lipid-lowering therapy is recommended. In certain embodiments lipid-lowering therapy is recommended when low HDL-C is accompanied by elevations in non-HDL-C and/or elevations in triglyceride. In certain embodiments, HDL-C concentrations of less than 40 mg/dL are considered low. In certain embodiments, HDL-C concentrations of less than 50 mg/dL are considered low.

"ApoB" means apolipoprotein B-100 protein. Concentration of ApoB in serum (or plasma) is typically quantified in mg/dL or nmol/L. "Serum ApoB" and "plasma ApoB" mean ApoB in the serum and plasma, respectively.

"LDL/HDL ratio" means the ratio of LDL-C to HDL-C.

"Oxidized-LDL" or "Ox-LDL-C" means LDL-C that is oxidized following exposure to free radicals.

"Individual having elevated LDL-C levels" means a subject who has been identified by a medical professional (e.g. a physician) as having LDL-C levels near or above the level at which therapeutic intervention is recommended, according to guidelines recognized by medical professionals. Such a subject can also be considered "in need of treatment" to decrease LDL-C levels.

"Individual having elevated apoB-100 levels" means a subject who has been identified as having apoB-100 levels near or below the level at which therapeutic intervention is recommended, according to guidelines recognized by medical professionals. Such a subject can also be considered "in need of treatment" to decrease apoB-100 levels.

"Treatment of elevated LDL-C levels" means administration of an antisense compound targeted to a JNK1 nucleic acid to a subject having elevated LDL-C levels.

"Treatment of atherosclerosis" means administration of an antisense compound targeted to a JNK1 nucleic acid to a subject who, based upon a physician's assessment, has or is likely to have atherosclerosis. "Prevention of atherosclerosis" means administration of an antisense compound targeted to a JNK1 nucleic acid to a subject who, based upon a physician's assessment, is susceptible to atherosclerosis.

As used herein, the term "modulation" refers to a perturbation of function or activity when compared to the level of the function or activity prior to modulation. For example, modulation includes the change, either an increase (stimulation or induction) or a decrease (inhibition or reduction) in gene expression. As further example, modulation of expression can include perturbing splice site selection of pre-mRNA processing.

As used herein, the term "expression" refers to all the functions and steps by which a gene's coded information is converted into structures present and operating in a cell. Such structures include, but are not limited to the products of transcription and translation.

"Antisense inhibition" means reduction of a target nucleic acid levels in the presence of an antisense compound complementary to a target nucleic acid compared to target nucleic acid levels in the absence of the antisense compound.

As used herein, the term "target" refers to a protein, the modulation of which is desired.

As used herein, the term "target gene" refers to a gene encoding a target.

"Targeting" means the process of design and selection of an antisense compound that will specifically hybridize to a target nucleic acid or a particular region of nucleotides within a target nucleic acid molecule and induce a desired effect.

"Targeted" means having a nucleobase sequence that will allow specific hybridization of an antisense compound to a target nucleic acid or a particular region of nucleotides within a target nucleic acid molecule to induce a desired effect. In certain embodiments, a desired effect is reduction of a target nucleic acid. In certain such embodiments, a desired effect is reduction of JNK1 mRNA.

As used herein, the terms "target nucleic acid," "target RNA," "target RNA transcript," "nucleic acid target" and "nucleic acid molecule encoding a target" refer to any nucleic acid molecule the expression or activity of which is capable of being modulated by an antisense compound. Target nucleic acids include, but are not limited to, RNA (including, but not limited to pre-mRNA and mRNA or portions thereof) transcribed from DNA encoding a target, and also cDNA derived from such RNA, and miRNA. For example, the target nucleic acid can be a cellular gene (or mRNA transcribed from the gene) whose expression is associated with a particular disorder or disease state, or a nucleic acid molecule from an infectious agent.

A "JNK1 nucleic acid" means any nucleic acid encoding JNK1. For example, in certain embodiments, a JNK1 nucleic acid includes, without limitation, a DNA sequence encoding JNK1, an RNA sequence transcribed from DNA encoding JNK1, and an mRNA sequence encoding JNK1. "JNK1 mRNA" means an mRNA encoding a JNK1 protein.

As used herein, the term "5' target site" refers to the nucleotide of a target nucleic acid which is complementary to the 5'-most nucleotide of a particular antisense compound.

As used herein, the term "3' target site" refers to the nucleotide of a target nucleic acid which is complementary to the 3'-most nucleotide of a particular antisense compound.

As used herein, the term "target region," refers to a portion of a target nucleic acid to which one or more antisense compounds is complementary.

As used herein, the term "target segment" refers to a smaller or sub-portions of a region within a target nucleic acid.

As used herein, the term "complementarity" refers to the ability of a nucleobase to base pair with another nucleobase. For example, in DNA, adenine (A) is complementary to thymine (T). For example, in RNA, adenine (A) is complementary to uracil (U). In certain embodiments, complementary nucleobase refers to a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair.

As used herein, the term "non-complementary nucleobase" refers to a nucleobase that does not form hydrogen bonds with another nucleobase or otherwise support hybridization.

As used herein, the term "complementary" refers to the capacity of an oligomeric compound to hybridize to another oligomeric compound or nucleic acid through base pairing. In certain embodiments, an antisense compound and its target are complementary to each other when a sufficient number of corresponding positions in each molecule are occupied by nucleobases that can pair with each other to allow stable association between the antisense compound and the target. One skilled in the art recognizes that the inclusion of mismatches is possible without eliminating the ability of the oligomeric compounds to remain in association. Therefore, described herein are antisense compounds that can comprise up to about 20% nucleotides that are mismatched (i.e., are not nucleobase complementary to the corresponding nucleotides of the target). Preferably the antisense compounds contain no more than about 15%, more preferably not more than about 10%, most preferably not more than about 5% or no mismatches. The remaining nucleotides are nucleobase complementary or otherwise do not disrupt hybridization (e.g., universal bases). One of ordinary skill in the alt would recognize the compounds provided herein are at least 80%, at least 85%, at least 90%, at least 95%, at least 96%, at least 97%, at least 98%, at least 99% or 100% complementary to a target nucleic acid.

As used herein, the term "mismatch" refers to a non-complementary nucleobase within a complementary oligomeric compound.

As used herein, "hybridization" means the pairing of complementary oligomeric compounds (e.g., an antisense compound and its target nucleic acid). While not limited to a particular mechanism, the most common mechanism of pairing involves hydrogen bonding, which can be Watson-Crick, Hoogsteen or reversed Hoogsteen hydrogen bonding, between complementary nucleoside or nucleotide bases (nucleobases). For example, the natural base adenine is nucleobase complementary to the natural nucleobases thymidine and uracil which pair through the formation of hydrogen bonds. The natural base guanine is nucleobase complementary to the natural bases cytosine and 5-methyl cytosine. Hybridization can occur under varying circumstances.

As used herein, the term "specifically hybridizes" refers to the ability of an oligomeric compound to hybridize to one nucleic acid site with greater affinity than it hybridizes to another nucleic acid site. In certain embodiments, an antisense oligonucleotide specifically hybridizes to more than one target site.

As used herein, "designing" or "designed to" refer to the process of designing an oligomeric compound that specifically hybridizes with a selected nucleic acid molecule.

"Portion" means a defined number of contiguous (i.e. linked) nucleobases of a target nucleic acid. In certain embodiments, a portion is a defined number of contiguous nucleobases of a target nucleic acid. In certain embodiments, a portion is a defined number of contiguous nucleobases of an antisense compound.

As used herein, the term "oligomeric compound" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

As used herein, the term "antisense compound" refers to an oligomeric compound that is at least partially complementary to a target nucleic acid molecule to which it hybridizes. In certain embodiments, an antisense compound modulates (increases or decreases) expression of a target nucleic acid. Antisense compounds include, but are not limited to, compounds that are oligonucleotides, oligonucleosides, oligonucleotide analogs, oligonucleotide mimetics, and chimeric combinations of these. Consequently, while all antisense compounds are oligomeric compounds, not all oligomeric compounds are antisense compounds.

As used herein, the term "oligonucleotide" refers to an oligomeric compound comprising a plurality of linked nucleotides. In certain embodiment, one or more nucleotides of an oligonucleotide is modified. In certain embodiments, an oligonucleotide contains ribonucleic acid (RNA) or deoxyribonucleic acid (DNA). In certain embodiments, oligonucleotides are composed of naturally- and/or non-naturally-occurring nucleobases, sugars and covalent internucleotide linkages, and can further include non-nucleic acid conjugates.

"Oligonucleoside" means an oligonucleotide in which the internucleoside linkages do not contain a phosphorus atom.

"Antisense oligonucleotide" means a single-stranded oligonucleotide having a nucleobase sequence that will permits hybridization to a corresponding region of a target nucleic acid.

"Motif" means the pattern of unmodified and modified nucleosides in an antisense compound.

"Chimeric antisense compounds" means an antisense compounds that have at least 2 chemically distinct regions, each region having a plurality of subunits.

As used herein, the term "gapmer" refers to a chimeric oligomeric compound comprising a central region (a "gap") and a region on either side of the central region (the "wings"), wherein the gap comprises at least one modification that is different from that of each wing. Such modifications include nucleobase, monomeric linkage, and sugar modifications as well as the absence of modification (unmodified). The gap region generally supports RNaseH cleavage.

As used herein, the term "nucleoside" means a glycosylamine comprising a nucleobase and a sugar. Nucleosides includes, but are not limited to, naturally occurring nucleosides, a basic nucleosides, modified nucleosides, and nucleosides having mimetic bases and/or sugar groups.

As used herein, the term "nucleotide" refers to a glycosomine comprising a nucleobase and a sugar having a phosphate group covalently linked to the sugar. Nucleotides can be modified with any of a variety of substituents.

As used herein, the term "nucleobase" refers to the base portion of a nucleoside or nucleotide. A nucleobase can comprise any atom or group of atoms capable of hydrogen bonding to a base of another nucleic acid.

As used herein, the term "monomer" refers to a single unit of an oligomer. Monomers include, but are not limited to, nucleosides and nucleotides, whether naturally occurring or modified.

As used herein, the term "deoxyribonucleotide" means a nucleotide having a hydrogen at the 2' position of the sugar portion of the nucleotide. Deoxyribonucleotides can be modified with any of a variety of substituents.

As used herein, the term "ribonucleotide" means a nucleotide having a hydroxy at the 2' position of the sugar portion of the nucleotide. Ribonucleotides can be modified with any of a variety of substituents.

"Unmodified nucleotide" means a nucleotide composed of naturally occurring nucleobases, sugar moieties and internucleoside linkages. In certain embodiments, an unmodified nucleotide is an RNA nucleotide (i.e., β-D-ribonucleosides) or a DNA nucleotide (i.e., β-D-deoxyribonucleoside).

"Modified nucleotide" means a nucleotide having, independently, a modified sugar moiety, modified internucleoside linkage, or modified nucleobase. A "modified nucleoside" means a nucleotide having, independently, a modified sugar moiety or modified nucleobase.

"Internucleoside linkage" means a covalent linkage between adjacent nucleosides.

"Naturally occurring internucleoside linkage" means a 3' to 5' phosphodiester linkage.

"Modified internucleoside linkage" means substitution and/or any change from a naturally occurring internucleoside linkage "Modified sugar moiety" means substitution and/or any change from a natural sugar moiety. For the purposes of this disclosure, a "natural sugar moiety" is a sugar moiety found in DNA (2'-H) or RNA (2'-OH).

"Modified nucleobase" means any nucleobase other than adenine, cytosine, guanine, thymidine, or uracil. An "unmodified nucleobase" means the purine bases adenine (A) and guanine (G), and the pyrimidine bases thymine (T), cytosine (C) and uracil (U).

"Natural sugar moiety" means a sugar moiety found in DNA (2'-H) or RNA (2'-OH).

"2'-O-methoxyethyl sugar moiety" means a 2'-substituted furanosyl ring having a 2'-O(CH2)2-OCH3(2'-O-methoxyethyl or 2'-MOE) substituent group.

"2'-O-methoxyethyl nucleotide" means a nucleotide comprising a 2'-O-methoxyethyl modified sugar moiety.

"Bicyclic nucleic acid sugar moiety" means a furanosyl ring modified by the bridging of two non-geminal ring atoms.

"Prodrug" means a therapeutic agent that is prepared in an inactive form that is converted to an active form (i.e., drug) within the body or cells thereof by the action of endogenous enzymes or other chemicals and/or conditions.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Cap structure" or "terminal cap moiety" means chemical modifications, which have been incorporated at either terminus of an antisense compound.

Overview

In the context of the invention, the terms "Jun N-terminal kinase," "c-Jun N-terminal kinase" and "JNK1 protein" refer to proteins actually known to phosphorylate the amino terminal (N-terminal) portion of the Jun subunit of AP-1, as well as those that have been tentatively identified as JNK1 proteins based on amino acid sequence but which can in fact additionally or alternatively bind and/or phosphorylate either other transcription factors (e.g., ATF2) or kinase substrates that are not known to be involved in transcription (Derijard et al., *Cell*, 1994, 76, 1025; Kallunki et al., *Genes & Development*, 1994, 8, 2996; Gutta et al., *EMBO J.*, 1996, 15, 2760).

AP-1 is one member of a family of related heterodimeric transcription factor complexes found in eukaryotic cells or viruses (*The* FOR *and* JUN *Families of Transcription Factors*, Angel and Hairlike, Eds., CBC Press, Boca Raton, Fla., 1994; Bohmann et al., *Science,* 1987, 238, 1386; Angel et al., *Nature,* 1988, 332, 166). Two relatively well-characterized AP-1 subunits are c-For and c-Jun; these two proteins are products of the c-for and c-jun proto-oncogenes, respectively. (Rahmsdorf, Chapter 13, and Rapp et al., Chapter 16 *In: The FOS and JUN Families of Transcription Factors,* Angel and Herrlich, Eds., CBC Press, Boca Raton, Fla., 1994)

The phosphorylation of proteins plays a key role in the transduction of extracellular signals into the cell. Typical MAP kinase pathways are known and recited in the literature. (See e.g., Cano et al., *Trends Biochem. Sci.,* 1995, 20, 117 Cobb et al., *J. Biol. Chem.,* 1995, 270, 14843; Seger et al., *FASEB J.,* 1995, 9, 726; Cano et al., *Trends Biochem. Sci.,* 1995, 20, 117).

One of the signal transduction pathways involves the MAP kinases Jun N-terminal kinase 1 (JNK1) and Jun N-terminal kinase 2 (JNK2) which are responsible for the phosphorylation of specific sites (Serine 63 and Serine 73) on the amino terminal portion of c-Jun. Phosphorylation of these sites potentiates the ability of AP-1 to activate transcription (Binetruy et al., *Nature,* 1991, 351, 122; Smeal et al., *Nature,* 1991, 354, 494). Besides JNK1 and JNK2, other JNK family members have been described, including JNK3 (Gutta et al., *EMBO J.,* 1996, 15, 2760), initially named p49$^{3F12}$ kinase (Mohit et al., *Neuron,* 1994, 14, 67).

Recent studies have indicated that JNKs interfere with insulin action in cultured cells and are activated by free fatty acids and inflammatory cytokines; both implicated in the development of type-2 diabetes. Thus, JNK can be a mediator of obesity and insulin resistance. (Hirosumi et al., *Nature,* 2002, 420:333-336).

JNKs or c-Jun N-terminal kinases are a family of serine/threonine protein kinases of the mitogen-activated protein kinase (MAPK) group and are involved in a variety of physiological functions. They are activated in response to different stimuli which cause cellular stress including heat shock, irradiation, hypoxia, chemotoxins, peroxides, and some cytokines (Bennett et al., 2003; Bogoyevitch et al., 2004). Obesity also causes cellular stress due to mechanical changes, excess lipid accumulation, abnormalities in intracellular energy fluxes, and altered nutrient availability, as well as changed plasma levels of cytokines (Hotamisligil, 2005; Ozcan et al., 2004; Waetzig and Herdegen, 2005). JNK activity is much higher in liver, fat and muscle in both genetically obese (ob/ob) mice and diet-induced obese (DIO) mice than in their respective controls (Hirosumi et al., 2002; Ozcan et al., 2004).

Obesity is considered a long-term disease. There are over thirty serious medical concerns related to obesity. Metabolic syndrome is a combination of medical disorders that increase one's risk for cardiovascular disease and diabetes. The symptoms, including high blood pressure, high triglycerides, decreased HDL and obesity, tend to appear together in some individuals. It affects a large number of people in a clustered fashion. In some studies, the prevalence in the USA is calculated as being up to 25% of the population. Metabolic syndrome is known under various other names, such as (metabolic) syndrome X, insulin resistance syndrome, Reaven's syndrome or CHAOS.

The present invention is based, in part, on the discovery of antisense compounds that target nucleic acid encoding JNK1 and which function to reduce JNK1 levels in a subject.

Effective treatments are needed for diabetes, obesity, metabolic syndrome and other diseases and conditions associated with glucose and/or lipid metabolism and/or the disregulation thereof. Certain compounds on the market for the treatment of diabetes are known to induce weight gain, a very undesirable side effect to the treatment of this disease. Therefore, a compound that has the potential to treat both diabetes and obesity would provide a significant improvement over current treatments.

A role for JNK1 in both insulin resistance and obesity is identified and JNK1 is presented herein as a therapeutic target for a range of metabolic diseases and conditions, including diabetes, obesity and metabolic syndrome. Therefore, provided herein are compounds and compositions targeting JNK1 and methods for the treatment of metabolic diseases and conditions. Metabolic conditions are characterized by an alteration or disturbance in metabolic function.

In accordance with the present invention, oligonucleotides are provided which specifically hybridize with a nucleic acid encoding a JNK1 protein. Certain oligonucleotides of the invention are designed to bind either directly to mRNA transcribed from, or to a selected DNA portion of, a JNK1 gene that encodes a JNK1 protein, thereby modulating the expression thereof and/or the phosphorylation of one or more substrates for the JNK1 protein. Pharmaceutical compositions comprising the oligonucleotides of the invention, and various methods of using the oligonucleotides of the invention, including methods of modulating one or more metastatic events, are also herein provided.

Provided herein are methods, compounds and compositions for modulating JNK1 expression in a subject. In certain embodiments, methods, compounds and compositions are provided for reducing JNK1 levels, expression, and/or activity in a subject. In certain embodiments the reduction of JNK1 expression, activity and/or nucleic acid levels occurs in liver and fat tissues of a subject. In certain embodiments the subject is an animal. In certain embodiments the animal is a human.

Provided herein are methods, compounds and compositions for the treatment, prevention and/or amelioration of diseases or conditions associated with glucose and/or lipid metabolism and/or the disregulation thereof. In certain embodiments, the methods, compounds and compositions are for the treatment, prevention and/or amelioration of diabetes, obesity and metabolic syndrome. In certain embodiments, the methods, compounds and compositions are for the treatment, prevention and/or amelioration of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease. In certain embodiments, such methods, compounds and compositions are used to treat, slow, prevent, delay or ameliorate the sequalae of diabetes including, but not limited to, retinopathy, neuropathy, cardiovascular complications and nephropathy.

Provided herein are methods, compounds and compositions for improving blood glucose control or tolerance. In certain embodiments, the methods, compounds and compositions are for improving insulin sensitivity. Also provided are methods, compounds and compositions for the reduction of glucose levels. In certain embodiments, such glucose levels can be blood, plasma and/or serum glucose levels. In certain embodiments, such glucose levels can be fed or fasting glucose levels Also provided are methods, compounds and compositions for the reduction of lipids. Also provided are methods, compounds and compositions for the reduction of triglyceride levels in a subject. In certain embodiments, such triglyceride levels are plasma triglyceride levels. In certain embodiments, such triglyceride levels are liver triglyceride levels. Also provided are methods of improving liver steatosis. Also provided are methods, compounds and compositions for the reduction of cholesterol levels. In certain embodiments, such cholesterol levels are plasma cholesterol levels.

Also provided are methods, compounds and compositions for modulating expression of metabolic and/or lipogenic genes. In certain embodiments, the metabolic and/or lipogenic genes listed in Table 35 below. In certain embodiments expression levels of one or more of ACC1, ACC2, FAS, SCD1 and DGAT1, DGAT2, RBP4, G6 Pase and PKCε are lowered. In certain embodiments, levels are reduced by about 30% to about 70%. Also provided are methods, compounds and compositions for lowering lipogenesis. In certain embodiments lipogenesis is lowered by lowering expression of such metabolic or lipogenic genes. In certain embodiments, expression levels of $AR\beta_3$, UCP1, UCP2 and PPARα are increased. In certain embodiments, levels are increased by up to about 70%. Such methods include administering to a subject an antisense compound targeted to a nucleic acid encoding JNK1. In certain embodiments, such methods include the administration of a therapeutically effective amount of an antisense compound targeted to a JNK1 nucleic acid. In certain embodiments, the compound is administered in a composition. In certain embodiments the subject is an animal. In certain embodiments the animal is a human. In certain embodiments, the subject to which the antisense compound is administered and in which levels are modulated has one or more of the diseases or disorders listed above. In certain embodiments, the subject to which the antisense compound is administered and in which levels are lowered has obesity, hypercholesterolemia, mixed dyslipidemia, atherosclerosis, coronary heart disease, diabetes, type II diabetes, type II diabetes with dyslipidemia, dyslipidemia, hypertriglyceridemia, hyperlipidemia, hyperfattyacidemia, hepatic steatosis, non-alcoholic steatohepatitis (NASH), or non-alcoholic fatty liver disease (NAFL).

In certain embodiments, the subject to which the antisense compound is administered has elevated glucose levels, triglyceride levels or cholesterol levels or any combination thereof. In certain embodiments, such glucose levels can be blood, plasma and/or serum glucose levels. In certain embodiments, such glucose levels can be fed or fasting glucose levels. In certain embodiments, such glucose levels are fed or fasting blood glucose levels. In certain embodiments, such triglyceride levels are plasma triglyceride levels. In certain embodiments, such triglyceride levels are liver triglyceride levels. In certain embodiments, such cholesterol levels are plasma cholesterol levels. In certain embodiments, the administration thereby reduces glucose levels, triglyceride levels or cholesterol levels. In certain embodiments the subject is an animal. In certain embodiments the animal is a human.

Also provided are methods for reducing serum glucose levels, serum triglyceride levels or plasma cholesterol levels in a subject which include selecting a subject having elevated serum glucose levels, serum triglyceride levels or plasma cholesterol levels, and administering to the individual a therapeutically effective amount of an antisense compound targeted to a JNK1 nucleic acid, and additionally monitoring serum glucose levels, serum triglyceride levels or plasma cholesterol levels. In certain embodiments the individual is an animal. In certain embodiments the individual is a human.

Further provided are methods for treating, preventing and/or ameliorating diabetes, obesity or metabolic syndrome, or another disease or condition associated with glucose and/or lipid metabolism and/or the disregulation thereof, in a subject. Such method includes selecting a subject diagnosed with diabetes, obesity or metabolic syndrome or other disease or condition associated with glucose and/or lipid metabolism, administering to the individual a therapeutically effective amount of an antisense compound targeted to a JNK1 nucleic acid, and monitoring factors related to diabetes, obesity or metabolic syndrome or other related disease or condition.

Further provided are methods of increasing metabolic rate. Also provided are methods for lowering body weight gain. Also provided are methods for lowering epididymal fat pad weight. Also provided are methods for lowering whole body fat content. Such methods include administering to a subject an antisense compound targeted to a nucleic acid encoding JNK1. In certain embodiments, such methods include the administration of a therapeutically effective amount of an antisense compound targeted to a JNK1 nucleic acid. In certain embodiments, the compound is administered in a composition. In certain embodiments the subject is an animal. In certain embodiments the animal is a human. In certain embodiments, the subject to which the antisense compound is administered and in which metabolic rate is increased and/or weight or fat content is lowered has one or more of the diseases or disorders listed above. In certain embodiments, the subject to which the antisense compound is administered and in which metabolic rate is increased and/or weight or fat content is lowered has obesity, diabetes or metabolic syndrome.

It is understood that the terms individual and subject are used interchangeably herein and that any of the methods provided herein can be useful for a subject or a subject and that subject or individual can be an animal and particularly a human.

Any of the methods provided herein can further comprise monitoring serum or plasma glucose levels, serum or plasma triglyceride levels or serum or plasma cholesterol levels.

In any of the aforementioned methods, administration of the antisense compound can comprise parenteral administration. The parenteral administration can further comprise subcutaneous or intravenous administration.

In any of the compounds, compositions or methods provided herein, the antisense compound can have least 80%, at least 90%, or at least 95% complementarity to SEQ ID NO: 87, 89, 90 or 91. Alternatively, the antisense compound can have 100% complementarity to SEQ ID NO: 87, 89, 90 or 91.

The antisense compounds provided herein and employed in any of the described methods can be 8 to 80 subunits in length, 12 to 50 subunits in length, 12 to 30 subunits in length, 15 to 30 subunits in length, 18 to 24 subunits in length, 19 to 22 subunits in length, or 20 subunits in length. Further, the antisense compounds employed in any of the described methods can be antisense oligonucleotides 8 to 80 nucleotides in length, 12 to 50 nucleotides in length, 12 to 30 nucleotides in length 15 to 30 nucleotides in length, 18 to 24 nucleotides in length, 19 to 22 nucleotides in length, or 20 nucleotides in length.

In any of the compounds, compositions and methods provided, the antisense compound can be an antisense oligonucleotide. Moreover, the antisense oligonucleotide can be chimeric. The chimeric antisense oligonucleotide can be a gapmer antisense oligonucleotide. The gapmer antisense oligonucleotide can comprise a gap segment of ten 2'-deoxynucleotides positioned between wing segments of five 2'-MOE nucleotides.

In any of the compounds, compositions and methods provided, the antisense compounds can have at least one modified internucleoside linkage. Additionally, each internucleoside linkage can be a phosphorothioate internucleoside linkage. Each cytosine can be a 5-methyl cytosine.

A compound for treatment of obesity and metabolic syndrome can be an antisense compound 12 to 30 nucleobases targeted to a JNK1 nucleic acid. The compound can have at least 70% to 100% complementarity to any of SEQ ID Nos: 87, 89, 90 or 91. The antisense oligonucleotide can be a gapmer antisense oligonucleotide. The gapmer antisense oligonucleotide can comprise a gap segment often 2'-deoxynucleotides positioned between wing segments of five 2'-MOE nucleotides.

The antisense compounds can have at least one modified internucleoside linkage. Additionally, each internucleoside linkage can be a phosphorothioate internucleoside linkage. Each cytosine can be a 5-methyl cytosine.

Both genetic and dietary mouse models of obesity were treated with JNK1 ASO. JNK1 ASO treatment markedly and specifically reduced the gene expression of JNK1 in both liver and fat tissues, which resulted in a dramatic reduction of JNK1 activity in these tissues. The treatment lowered BW (or body weight gain), fat depot weight and whole body fat content, and increased metabolic rate without causing liver toxicity or other side-effects as compared to controls. The treatment markedly lowered fed and fasting plasma glucose and insulin levels, improved glucose and insulin tolerance, improved liver steatosis and lowered plasma cholesterol levels. These data indicate that specific inhibition of JNK1 expression and activity with ASO in the two major metabolic tissues improved adiposity and related metabolic disorders in these models.

Treatment also resulted in improved feed efficiency. Additionally, an increased metabolic rate in the ASO-treated mice was confirmed by indirect calorimetry. Quantitative RT-PCR analysis found increased gene expression in BAT from these mice of both $AR\beta_3$ and UCP1, two key genes involved in catabolism and fuel combustion in rodents. Increased expression of PPARα, UCP2, and UCP3, and decreased expression of ACC2 were also found in either liver or WAT, leading further support to the finding of an increased metabolic rate. In addition, an extensive and profound decrease in the expression of lipogenic genes and unchanged expression of two key lipolytic genes, HSL and ATGL, were found in WAT, indicating decreased lipogenesis and unchanged lipolysis with reduction of JNK1 expression in this tissue. Marked decrease in expression of ACC1 and FAS, two key genes involved in de novo fatty acid synthesis, in liver was also detected. Furthermore, increased fatty acid oxidation and decreased de novo fatty acid synthesis were directly demonstrated in JNK1 ASO-transfected hepatocytes. Taken together, these data demonstrate that decreased BW or BW gain and lowered adiposity in the ASO-treated mice were attributable to increased fuel combustion/metabolic rate and decreased lipogenesis.

Antisense reduction of JNK1 activity lowers liver TG content and improves hepatic steatosis. Additionally, plasma cholesterol levels are improved. These changes were accompanied by increased expression of hepatic UCP2 and PPARα genes and decreased expression of the key hepatic lipogenic genes including ACL, ACC1 and FAS. Without being bound to any theory, these changes in gene expression indicate an increased shunting of citrate into the TCA cycle and electron transport chain for oxidation and a reduced breakdown of it (by ACL) to produce acetyl-CoA for cholesterol and fatty acid synthesis. Improved hepatic steatosis and plasma cholesterol levels in JNK1 ASO-treated mice can therefore be due to increased hepatic substrate oxidation and decreased hepatic lipogenesis. In vitro studies that showed decreased de novo sterol synthesis and fatty acid synthesis and increased fatty acid oxidation in JNK1 ASO-transfected hepatocytes provide additional support. In addition, decreased expression of hepatic ApoB100 in JNK1 ASO-treated mice was found. Reduction of hepatic ApoB100 expression lowers plasma cholesterol levels in different models of hyperlipidemia due to reduced hepatic cholesterol synthesis and export.

Specific reduction of JNK1 expression with ASO in just liver and fat profoundly improved insulin sensitivity, normalized plasma glucose and insulin levels and reduced glucose excursion during ITT and GTT. The positive effects were found to be accompanied by increased expression of hepatic GK and GS and decreased expression of hepatic G6Pase and PKCε, and reduced expression of RBP4 in WAT. GK is the rate-limiting enzyme for hepatic synthesis of glucose-6-phosphate (which is further used for glycolysis or glycogen synthesis) from glucose that is taken-up from blood, whereas G6Pase is the final "gate" for hepatic glucose output by breaking down glucose-6-phosphate (that is from either gluconeogenesis or glycogenolysis) to release glucose into blood. GS is the rate-limiting enzyme for glycogen synthesis that uses glucose-6-phosphate as the primary substrate. These changes in gene expression indicate that antisense reduction of JNK1 expression improves liver and even whole body insulin sensitivity, promotes blood glucose utilization and/or storage in liver while inhibiting hepatic glucose output, thus, resulting in improved blood glucose and insulin levels. An improved insulin signaling activity in JNK1 ASO treated mice showing decreased phosphorylation of $IRS1^{Ser302/307}$ and increased phosphorylation of $Akt^{Ser473}$ in response to insulin further demonstrates that antisense reduction of JNK1 expression improves insulin sensitivity.

Obesity, which is tightly associated with type 2 diabetes, hyperlipidemia, and fatty liver diseases, has become epidemic worldwide. JNK1 plays an important role in metabolism and energy homeostasis and antisense reduction of its expression in liver and fat increases metabolic rate and improves body weight and adiposity, which is accompanied by improved liver steatosis, hypercholesterolemia and insulin sensitivity in both genetically leptin-deficient and diet-induced obese mice. Therefore, JNK1 is a useful therapeutic target for the treatment of obesity and related metabolic disorders.

The antisense compounds provided herein are therefore useful for treating a number of metabolic conditions, including diabetes, obesity and metabolic syndrome. Such treatments encompass a therapeutic regimen that results in a clinically desirable outcome. The clinically desired outcomes can be tied to glucose metabolism. For example, the antisense compounds and methods provided herein are useful for improving blood glucose control or tolerance and for improving insulin sensitivity in a subject in need thereof. The antisense compounds and methods provided herein are also useful for reducing plasma resisting levels in a subject in need thereof. The antisense compounds and methods provided herein are also useful for reducing glucose levels in a subject in need thereof. The compounds and methods are particularly useful for reducing blood, plasma and/or serum glucose levels. The compounds and methods are useful for reducing both fed and fasting glucose levels. Such clinical outcomes are desirable in disease and disorders related to glucose metabolism and insulin resistance including, for example, diabetes, particularly type II diabetes, obesity and metabolic syndrome. Therefore, the antisense compounds and methods provided herein are useful for the treatment of such diseases and disorders.

The clinically desirable outcomes can also be tied to lipid metabolism. For example, the antisense compounds and methods provided herein are also useful for the reduction of lipids in a subject in need thereof, particularly serum lipids. The reduction in lipids can result from a lowering of lipogenisis and particularly a lowering of lipogenic genes including, but not limited to ACC1, ACC2, FAS, SCD1 and DGAT1. In particular, the antisense compounds and methods are useful for reducing triglyceride and cholesterol levels in a subject in need thereof. The compounds and methods are particularly useful for reducing plasma triglyceride levels and plasma cholesterol levels. The compounds and methods are also particularly useful for reducing liver triglyceride levels. Additionally, the antisense compounds and methods provided herein are also useful for improving liver steatosis. The compounds and methods are also particularly useful for increasing metabolic rate and, in turn, lowering body weight gain. The compounds and methods are also particularly useful for lowering epididymal fat pad weight and whole body fat content. Such clinical outcomes are desirable in diseases and disorders of lipid as well as glucose metabolism and insulin resistance including, for example, diabetes, metabolic syndrome, obesity, hypercholesterolemia, mixed dyslipidemia, atherosclerosis, coronary heart disease, diabetes, type II diabetes, type II diabetes with dyslipidemia, dyslipidemia, hypertriglyceridemia, hyperlipidemia, hyperfattyacidemia, hepatic steatosis, non-alcoholic steatohepatitis (NASH), or non-alcoholic fatty liver disease (NAFLD). NAFLD is a condition characterized by fatty inflammation of the liver that is not due to excessive alcohol use (for example, alcohol consumption of over 20 g/day). In certain embodiments, NAFLD is related to insulin resistance and the metabolic syndrome. NASH is a condition characterized by inflammation and the accumulation of fat and fibrous tissue in the liver that is not due to excessive alcohol use. NASH is an extreme form of NAFLD. Therefore, the antisense compounds and methods provided herein are useful for the treatment of such diseases and disorders.

Elevated levels of blood glucose and triglycerides are recognized as major risk factors for development of diabetes, obesity and metabolic syndrome. Elevated blood glucose levels or elevated triglyceride levels are also considered a risk factor in the development and progression of atherosclerosis. Atherosclerosis can lead to coronary heart disease, stroke, or peripheral vascular disease. Accordingly provided herein are pharmaceutical agents for lowering elevated levels of blood glucose and triglycerides.

Metabolic syndrome is a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497). Accordingly, the compounds and methods provided herein can be used to treat individuals exhibiting one or more risk factors for metabolic syndrome. Particularly, the compounds and methods provided herein can be used to reduce body weight, thereby likely reducing waist circumference, and fasting glucose levels.

As illustrated herein, administration of an antisense oligonucleotide targeted to JNK1 to animals models of diabetes and obesity which exhibit insulin resistance, hyperglycemia and hyperlipidemia, resulted in antisense inhibition of JNK1, a reduction in plasma glucose and triglyceride levels and reduction of liver triglycerides. Reduction in triglycerides was also accompanied by a reduction in lipogenic genes. Particularly, expression of ACC1, ACC2, FAS, SCD1 and DGAT1 were reduced. Thus, it is demonstrated that in an experimental model of hyperglycemia and hyperlipidemia, antisense inhibition of JNK1 results in reduced glucose and triglyceride levels and reduced lipogenesis. Accordingly, provided herein are methods of reducing lipogenesis, blood glucose and triglyceride levels through the administration of an antisense compound targeted to a JNK1 nucleic acid. Blood glucose and triglyceride levels are considered a risk factor for development of diabetes, obesity and metabolic syndrome. Accordingly, also provided herein are methods for the treatment, prevention and/or amelioration of diabetes, obesity and metabolic syndrome, and for the treatment, prevention and/or amelioration of associated disorders. Also provided herein are methods for the treatment of conditions characterized by elevated liver triglycerides, such as hepatic steatosis.

Certain Indications

In certain embodiments, the invention provides methods of treating a subject comprising administering one or more pharmaceutical compositions of the present invention. In certain embodiments, the individual has diabetes, obesity, metabolic syndrome and/or associated disorders including but not limited to hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

Hypercholesterolemia is a condition characterized by elevated serum cholesterol. Hyperlipidemia is a condition characterized by elevated serum lipids. Hypertriglyceridemia is a condition characterized by elevated triglyceride levels. Non-familial hypercholesterolemia is a condition characterized by elevated cholesterol that is not the result of a single gene mutation. Is polygenic hypercholesterolemia is a condition characterized by elevated cholesterol that results from the influence of a variety of genetic factors. In certain embodiments, polygenic hypercholesterolemia can be exacerbated by dietary intake of lipids. Familial hypercholesterolemia (FH) is an autosomal dominant metabolic disorder characterized by a mutation in the LDL-receptor (LDL-R) gene, markedly elevated LDL-C and premature onset of atherosclerosis. A diagnosis of familial hypercholesterolemia is made when a individual meets one or more of the following criteria: genetic testing confirming 2 mutated LDL-receptor genes; genetic testing confirming one mutated LDL-receptor gene; document history of untreated serum LDL-cholesterol greater than 500 mg/dL; tendinous and/or cutaneous xanthoma prior to age 10 years; or, both parents have documented elevated serum LDL-cholesterol prior to lipid-lowering therapy consistent with heterozygous familial hypercholesterolemia. Homozygous familial hypercholesterolemia (HoFH) is a condition characterized by a mutation in both maternal and paternal LDL-R genes. Heterozygous familial hypercholesterolemia (HeFH) is a condition characterized by a mutation in either the maternal or paternal LDL-R gene. Mixed dyslipidemia is a condition characterized by elevated serum cholesterol and elevated serum triglycerides. Diabetic dyslipidemia or Type II diabetes with dyslipidemia is a condition characterized by Type II diabetes, reduced HDL-C, elevated serum triglycerides, and elevated small, dense LDL particles.

In one embodiment are methods for decreasing blood glucose levels or triglyceride levels, or alternatively methods for treating obesity or metabolic syndrome, by administering to a subject suffering from elevated glucose or triglyceride levels a therapeutically effective amount of an antisense compound targeted to a JNK1 nucleic acid. In another embodiment, a method of decreasing blood glucose or triglyceride levels comprises selecting a subject in need of a decrease in blood glucose or triglyceride levels, and administering to the individual a therapeutically effective amount of an antisense compound targeted to a JNK1 nucleic acid. In a further embodiment, a method of reducing risk of development of obesity and metabolic syndrome includes selecting a subject having elevated blood glucose or triglyceride levels and one or more additional indicators risk of development of obesity or metabolic syndrome, and administering to the individual a therapeutically effective amount of an antisense compound targeted to a JNK1 nucleic acid.

In one embodiment, administration of a therapeutically effective amount of an antisense compound targeted a JNK1 nucleic acid is accompanied by monitoring of glucose levels or triglyceride levels in the serum of a subject, to determine a subject's response to administration of the antisense compound. A subject's response to administration of the antisense compound is used by a physician to determine the amount and duration of therapeutic intervention.

Atherosclerosis can lead to coronary heart disease, stroke, or peripheral vascular disease. Elevated blood glucose levels or elevated triglyceride levels are considered a risk factor in the development and progression of atherosclerosis. Accordingly, in one embodiment, a therapeutically effective amount of an antisense compound targeted to a JNK1 nucleic acid is administered to a subject having atherosclerosis. In a further embodiment a therapeutically effective amount of antisense compound targeted to a JNK1 nucleic acid is administered to a subject susceptible to atherosclerosis. Atherosclerosis is assessed directly through routine imaging techniques such as, for example, ultrasound imaging techniques that reveal carotid intimomedial thickness. Accordingly, treatment and/or prevention of atherosclerosis further include monitoring atherosclerosis through routine imaging techniques. In one embodiment, administration of an antisense compound targeted to a JNK1 nucleic acid leads to a lessening of the severity of atherosclerosis, as indicated by, for example, a reduction of carotid intimomedial thickness in arteries.

Measurements of cholesterol, lipoproteins and triglycerides are obtained using serum or plasma collected from a subject. Methods of obtaining serum or plasma samples are routine, as are methods of preparation of the serum samples for analysis of cholesterol, triglycerides, and other serum markers.

A physician can determine the need for therapeutic intervention for individuals in cases where more or less aggressive blood glucose or triglyceride-lowering therapy is needed. The practice of the methods herein can be applied to any altered guidelines provided by the NCEP, or other entities that establish guidelines for physicians used in treating any of the diseases or conditions listed herein, for determining coronary heart disease risk and diagnosing metabolic syndrome.

In one embodiment, administration of an antisense compound targeted a JNK1 nucleic acid is parenteral administration. Parenteral administration can be intravenous or subcutaneous administration. Accordingly, in another embodiment, administration of an antisense compound targeted to a JNK1 nucleic acid is intravenous or subcutaneous administration. Administration can include multiple doses of an antisense compound targeted to a JNK1 nucleic acid.

In certain embodiments a pharmaceutical composition comprising an antisense compound targeted to JNK1 is for use in therapy. In certain embodiments, the therapy is the reduction of blood glucose, serum triglyceride or liver triglyceride in a subject. In certain embodiments, the therapy is the treatment of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease. In additional embodiments, the therapy is the reduction of CHD risk. CHD risk equivalents refers to indicators of clinical atherosclerotic disease that confer a high risk for coronary heart disease, and include clinical coronary heart disease, symptomatic carotid artery disease, peripheral arterial disease, and/or abdominal aortic aneurysm. In certain the therapy is prevention of atherosclerosis. In certain embodiments, the therapy is the prevention of coronary heart disease.

In certain embodiments pharmaceutical composition comprising an antisense compound targeted to JNK1 is used for the preparation of a medicament for reduction of blood glucose, serum triglyceride or liver triglyceride. In certain embodiments pharmaceutical composition comprising an antisense compound targeted to JNK1 is used for the preparation of a medicament for reducing coronary heart disease risk. In certain embodiments an antisense compound targeted to JNK1 is used for the preparation of a medicament for the treatment of hypercholesterolemia, mixed dyslipidemia, atherosclerosis, a risk of developing atherosclerosis, coronary heart disease, a history of coronary heart disease, early onset coronary heart disease, one or more risk factors for coronary heart disease, type II diabetes, type II diabetes with dyslipidemia, dyslipidemia, hypertriglyceridemia, hyperlipidemia, hyperfattyacidemia, hepatic steatosis, non-alcoholic steatohepatitis, or non-alcoholic fatty liver disease.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease or condition as the one or more pharmaceutical compositions of the present invention. In certain embodiments, such one or more other pharmaceutical agents are designed to treat a different disease or condition as the one or more pharmaceutical compositions of the present invention. In certain embodiments, such one or more other pharmaceutical agents are designed to treat an undesired effect of one or more pharmaceutical compositions of the present invention. In certain embodiments, one or more pharmaceutical compositions of the present invention are co-administered with another pharmaceutical agent to treat an undesired effect of that other pharmaceutical agent. In certain embodiments, one or more pharmaceutical compositions of the present invention and one or more other pharmaceutical agents are administered at the same time. In certain embodiments, one or more pharmaceutical compositions of the present invention and one or more other pharmaceutical agents are administered at different times. In certain embodiments, one or more pharmaceutical compositions of the present invention and one or more other pharmaceutical agents are prepared together in a single formulation. In certain embodiments, one or more pharmaceutical compositions of the present invention and one or more other pharmaceutical agents are prepared separately.

In certain embodiments, pharmaceutical agents that can be co-administered with a pharmaceutical composition comprising an antisense compound targeted to a JNK1 nucleic acid include glucose-lowering agents and therapies. In some embodiments, the glucose-lowering agent is a PPAR agonist (gamma, dual, or pan), a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, a meglitinide, a thiazolidinedione, or a sulfonylurea.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain such embodiments, the glucose-lowering agent is administered prior to administration of a pharmaceutical composition of the present invention. In certain such embodiments, the glucose-lowering agent is administered following administration of a pharmaceutical composition of the present invention. In certain such embodiments the glucose-lowering agent is administered at the same the as a pharmaceutical composition of the present invention. In certain such embodiments the dose of a co-administered glucose-lowering agent is the same as the dose that would be administered if the glucose-lowering agent was administered alone. In certain such embodiments the dose of a co-administered glucose-lowering agent is lower than the dose that would be administered if the glucose-lowering agent was administered alone. In certain such embodiments the dose of a co-administered glucose-lowering agent is greater than the dose that would be administered if the glucose-lowering agent was administered alone.

In certain embodiments, pharmaceutical agents that can be co-administered with a pharmaceutical composition comprising an antisense compound targeted to a JNK1 nucleic acid include anti-obesity agents. Such anti-obesity agents therapeutics can be administered as described above for glucose lowering agents.

Further provided is a method of administering an antisense compound targeted to a JNK1 nucleic acid via injection and further including administering a topical steroid at the injection site.

In certain embodiments, pharmaceutical agents that can be co-administered with a pharmaceutical composition of the present invention include lipid-lowering agents. In certain such embodiments, pharmaceutical agents that can be co-administered with a pharmaceutical composition of the present invention include, but are not limited to atorvastatin, simvastatin, rosuvastatin, and ezetimibe. In certain such embodiments, the lipid-lowering agent is administered prior to administration of a pharmaceutical composition of the present invention.

In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, a co-administered pharmaceutical agent is a bile acid sequestrant. In certain such embodiments, the bile acid sequestrant is selected from cholestyramine, colestipol, and colesevelam.

In certain embodiments, a co-administered pharmaceutical agent is a nicotinic acid. In certain such embodiments, the nicotinic acid is selected from immediate release nicotinic acid, extended release nicotinic acid, and sustained release nicotinic acid.

In certain embodiments, a co-administered pharmaceutical agent is a fibric acid. In certain such embodiments, a fibric acid is selected from gemfibrozil, fenofibrate, clofibrate, bezafibrate, and ciprofibrate.

Further examples of pharmaceutical agents that can be co-administered with a pharmaceutical composition of the present invention include, but are not limited to, corticosteroids, including but not limited to prednisone; immunoglobulins, including, but not limited to intravenous immunoglobulin (IVIg); analgesics (e.g., acetaminophen); anti-inflammatory agents, including, but not limited to non-steroidal anti-inflammatory drugs (e.g., ibuprofen, COX-1 inhibitors, and COX-2, inhibitors); salicylates; antibiotics; antivirals; antifungal agents; antidiabetic agents (e.g., biguanides, glucosidase inhibitors, insulins, sulfonylureas, and thiazolidenediones); adrenergic modifiers; diuretics; hormones (e.g., anabolic steroids, androgen, estrogen, calcitonin, progestin, somatostan, and thyroid hormones); immunomodulators; muscle relaxants; antihistamines; osteoporosis agents (e.g., biphosphonates, calcitonin, and estrogens); prostaglandins, antineoplastic agents; psychotherapeutic agents; sedatives; poison oak or poison sumac products; antibodies; and vaccines.

In certain embodiments, the pharmaceutical compositions of the present invention can be administered in conjunction with a lipid-lowering therapy. In certain such embodiments, a lipid-lowering therapy is therapeutic lifestyle change. In certain such embodiments, a lipid-lowering therapy is LDL apheresis.

In certain embodiments obesity is drug induced. In a particular embodiment obesity is induced by treatment with a psychotherapeutic drug or agent. Therapeutic use of certain psychotherapeutic agents, namely atypical antipsychotic agents can increase the risk of metabolic abnormalities and there use is generally associated with weight gain and impaired glucose tolerance. The percentage of patients gaining weight following antipsychotic therapy can reach up to 80% depending on the antipsychotic used, with 30% or more developing obesity. Along with associated medical complications, such metabolic abnormalities increase the percentage of non-compliance patients and results in an increased risk of relapse.

Due to the ability of JNK1 antisense oligonucleotides to increase metabolic rate and insulin sensitivity and reduce adiposity and weight gain, these compounds can be administered to reduce metabolic abnormalities associated with treatment with antipsychotic agents. In certain embodiments the JNK1 antisense oligonucleotide is delivered in a method of reducing metabolic abnormalities associated with the therapeutic use of psychotherapeutic agents. Such weight inducing antipsychotic agents include, but are not limited to clozapine, olanzapine, aripiprazole, risperidone and ziprasidone.

In certain embodiments the JNK1 antisense oligonucleotide is delivered concomitant with delivery of the psychotherapeutic agent. Alternatively, delivery can be in the same formulation or can be administered separately. In a certain embodiment, the JNK1 antisense oligonucleotide is administered after treatment with an obesity inducing drug or agent is ceased. In a particular embodiment administering of the JNK1 antisense compound results in increased metabolic rate or decreasing adiposity or both without affecting the CNS effects of the psychotherapeutic agent.

In certain embodiments, JNK1 antisense oligonucleotides are administered in combination either in the same formulation or separate formulations with other anti-obesity drugs or agents. In certain embodiment, the anti-obesity agents are CNS based such as, but not limited to, sibutramine or GLP-1 based such as, but not limited to, liraglutide.

Antisense Compounds

Provided herein are antisense oligonucleotides that modulate the JNK1, JNK2 and JNK3 proteins. Such modulation is desirable for treating, alleviating or preventing various disorders or diseases, such as obesity and metabolic syndrome. Such inhibition is further desirable for preventing or modulating the development of such diseases or disorders in an animal suspected of being, or known to be, prone to such diseases or disorders.

Methods of modulating the expression of JNK1 proteins comprising contacting animals with oligonucleotides specifically hybridizable with a nucleic acid encoding a JNK1 protein are herein provided. These methods are also useful for the diagnosis of conditions associated with such expression and activation.

Also provided herein are methods that comprise inhibiting JNK1-mediated activity using antisense oligonucleotides. These methods employ the oligonucleotides of the invention and are believed to be useful both therapeutically and as clinical research and diagnostic tools. Provided are methods for inhibiting the expression of JNK1 from a nucleic acid for the treatment, prevention or amelioration of a condition comprising reducing body weight gain, reducing epididymal fat pad weight, reducing whole body fat content, increasing metabolic rate, reducing fed plasma glucose, reducing fasting plasma glucose, reducing fed plasma insulin, reducing fasted plasma insulin, improving glucose tolerance, improving insulin tolerance, improving liver steatosis, reducing plasma cholesterol, reducing plasma transaminase or a combination thereof.

Oligonucleotides are used herein in antisense modulation of the function of DNA or messenger RNA (mRNA) encoding a protein the modulation of which is desired, and ultimately to regulate the amount of such a protein. Hybridization of an antisense oligonucleotide with its mRNA target interferes with the normal role of mRNA and causes a modulation of its function in cells. The functions of mRNA to be interfered with include all vital functions such as translocation of the RNA to the site for protein translation, actual translation of protein from the RNA, splicing of the RNA to yield one or more mRNA species, and possibly even independent catalytic activity which can be engaged in by the RNA. The overall effect of such interference with mRNA function is modulation of the expression of a protein, wherein modulation is either an increase (stimulation) or a decrease (inhibition) in the expression of the protein. In the context of the present invention, inhibition is the preferred form of modulation of gene expression.

It is preferred to target specific genes for antisense attack. Targeting an oligonucleotide to the associated nucleic acid, in the context of this invention, is a multistep process. The process begins with the identification of a nucleic acid sequence whose function is to be modulated. This can be, for example, a cellular gene (or mRNA transcribed from the gene) whose expression is associated with a particular disorder or disease state, or a foreign nucleic acid from an infectious agent. In the present invention, the target is a cellular gene associated with hyperproliferative disorders. The targeting process also includes determination of a site or sites within this gene for the oligonucleotide interaction to occur such that the desired effect, either detection or modulation of expression of the protein, will result. Once the target site or sites have been identified, oligonucleotides are chosen which are sufficiently complementary to the target, i.e., hybridize sufficiently well and with sufficient specificity to give the desired effect. Generally, there are five regions of a gene that can be targeted for antisense modulation: the 5' untranslated region (hereinafter, the "5'-UTR"), the translation initiation codon region (hereinafter, the "tIR"), the open reading frame (hereinafter, the "ORF"), the translation termination codon region (hereinafter, the "tTR") and the 3' untranslated region (hereinafter, the "3'-UTR"). As is known in the art, these regions are arranged in a typical messenger RNA molecule in the following order (left to right, 5' to 3'): 5'-UTR, tIR, ORF, tTR, 3'-UTR. As is known in the art, although some eukaryotic transcripts are directly translated, many ORFs contain one or more sequences, known as "introns," which are excised from a transcript before it is translated; the expressed (unexcised) portions of the ORF are referred to as "exons"

(Alberts et al, *Molecular Biology of the Cell,* 1983, Garland Publishing Inc., New York, pp. 411-415). Furthermore, because many eukaryotic ORFs are a thousand nucleotides or more in length, it is often convenient to subdivide the ORF into, e.g., the 5' ORF region, the central ORF region, and the 3' ORF region. In some instances, an ORF contains one or more sites that can be targeted due to some functional significance in vivo. Examples of the latter types of sites include intragenic stem-loop structures (see, e.g., U.S. Pat. No. 5,512, 438) and, in unprocessed mRNA molecules, intron/exon splice sites.

Within the context of the present invention, one preferred intragenic site is the region encompassing the translation initiation codon of the open reading frame (ORF) of the gene. Because, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Furthermore, 5'-UUU functions as a translation initiation codon in vitro (Brigstock et al., *Growth Factors,* 1990, 4, 45; Gelbert et al., *Somat. Cell. Mol. Genet.,* 1990, 16, 173; Gold and Stormo, in: *Escherichia coli and Salmonella typhimurium: Cellular and Molecular Biology,* Vol. 2, 1987, Neidhardt et al., Eds., American Society for Microbiology, Washington, D.C., p. 1303). Thus, the terms "translation initiation codon" and "start codon" can encompass many codon sequences, even though the initiator amino acid in each instance is typically methionine (in eukaryotes) or formylmethionine (prokaryotes). It is also known in the alt that eukaryotic and prokaryotic genes can have two or more alternative start codons, any one of which can be preferentially utilized for translation initiation in a particular cell type or tissue, or under a particular set of conditions, in order to generate related polypeptides having different amino terminal sequences (Markussen et al., *Development,* 1995, 121, 3723; Gao et al., *Cancer Res.,* 1995, 55, 743; McDermott et al., *Gene,* 1992, 117, 193; Perri et al., *J. Biol. Chem.,* 1991, 266, 12536; French et al., *J. Virol.,* 1989, 63, 3270; Pushpa-Rekha et al. *J. Biol. Chem.,* 1995, 270, 26993; Monaco et al., *J. Biol. Chem.,* 1994, 269, 347; DeVirgilio et al., *Yeast,* 1992, 8, 1043; Kanagasundaram et al., *Biochim. Biophys. Acta,* 1992, 1171, 198; Olsen et al. *Mol. Endocrinol.,* 1991, 5, 1246; Saul et al., *Appl. Environ. Microbiol.,* 1990, 56, 3117; Yaoita et al., *Proc. Natl. Acad. Sci. USA,* 1990, 87, 7090; Rogers et al., *EMBO J.,* 1990, 9, 2273). In the context of the invention, "start codon" and "translation initiation codon" refer to the codon or codons that are used in viva to initiate translation of an mRNA molecule transcribed from a gene encoding a JNK1 protein, regardless of the sequence(s) of such codons. It is also known in the art that a translation termination codon (or "stop codon") of a gene can have one of three sequences, i.e., 5'-UAA, 5'-UAG and 5'-UGA (the corresponding DNA sequences are 5'-TAA, 5'-TAG and 5'-TGA, respectively). The terms "start codon region" and "translation initiation region" refer to a portion of such an mRNA or gene that encompasses from about 25 to about 50 contiguous nucleotides in either direction (i.e., 5' or 3') from a translation initiation codon. Similarly, the terms "stop codon region" and "translation termination region" refer to a portion of such an mRNA or gene that encompasses from about 25 to about 50 contiguous nucleotides in either direction (i.e., 5' or 3') from a translation termination codon.

1. Oligonucleotides of the Invention: The present invention employs oligonucleotides for use in antisense modulation of one or more JNK1 proteins. In the context of this invention, the term oligonucleotide refers to an oligomer or polymer of ribonucleic acid or deoxyribonucleic acid. This term includes oligonucleotides composed of naturally-occurring nucleobases, sugars and covalent intersugar (backbone) linkages as well as oligonucleotides having non-naturally-occurring portions which function similarly. Such modified or substituted oligonucleotides are often preferred over native forms because of desirable properties such as, for example, enhanced cellular uptake, enhanced binding to target and increased stability in the presence of nucleases.

An oligonucleotide is a polymer of a repeating unit generically known as a nucleotide. The oligonucleotides in accordance with this invention preferably comprise from about 8 to about 30 nucleotides. An unmodified (naturally occurring) nucleotide has three components: (1) a nitrogen-containing heterocyclic base linked by one of its nitrogen atoms to (2) a 5-pentofuranosyl sugar and (3) a phosphate esterified to one of the 5' or 3' carbon atoms of the sugar. When incorporated into an oligonucleotide chain, the phosphate of a first nucleotide is also esterified to an adjacent sugar of a second, adjacent nucleotide via a 3'-5' phosphate linkage. The "backbone" of an unmodified oligonucleotide consists of (2) and (3), that is, sugars linked together by phosphodiester linkages between the 5' carbon of the sugar of a first nucleotide and the 3' carbon of a second, adjacent nucleotide. A "nucleoside" is the combination of (1) a nucleobase and (2) a sugar in the absence of (3) a phosphate moiety (Kornberg, A., *DNA Replication,* W.H. Freeman & Co., San Francisco, 1980, pages 4-7). The backbone of an oligonucleotide positions a series of bases in a specific order; the written representation of this series of bases, which is conventionally written in 5' to 3' order, is known as a nucleotide sequence.

Oligonucleotides can comprise nucleotide sequences sufficient in identity and number to effect specific hybridization with a particular nucleic acid. Such oligonucleotides which specifically hybridize to a portion of the sense strand of a gene are commonly described as antisense." In the context of the invention, hybridization means hydrogen bonding, which can be Watson-Crick, Hoogsteen or reversed Hoogsteen hydrogen bonding, between complementary nucleotides. For example, adenine and thymine are complementary nucleobases which pair through the formation of hydrogen bonds. Complementary refers to the capacity for precise pairing between two nucleotides. For example, if a nucleotide at a certain position of an oligonucleotide is capable of hydrogen bonding with a nucleotide at the same position of a DNA or RNA molecule, then the oligonucleotide and the DNA or RNA are considered to be complementary to each other at that position. The oligonucleotide and the DNA or RNA are complementary to each other when a sufficient number of corresponding positions in each molecule are occupied by nucleotides which can hydrogen bond with each other. An oligonucleotide is specifically hybridizable to its target sequence due to the formation of base pairs between specific partner nucleobases in the interior of a nucleic acid duplex. Among the naturally occurring nucleobases, guanine (G) binds to cytosine (C), and adenine (A) binds to thymine (T) or uracil (U). In addition to the equivalency of U (RNA) and T (DNA) as partners for A, other naturally occurring nucleobase equivalents are known, including 5-methylcytosine, 5-hydroxymethylcytosine (HMC), glycosyl HMC and gentiobiosyl HMC (C equivalents), and 5-hydroxymethyluracil (U equivalent). Furthermore, synthetic nucleobases which retain partner specificity are known in the art and include, for example, 7-deaza-Guanine, which retains partner specificity for C. Thus, an oligonucleotide's capacity to specifically hybridize with its target sequence will not be altered by any chemical modification to a nucleobase in the nucleotide sequence of the oligonucleotide which does not significantly effect its specificity for the partner nucleobase in the target oligonucleotide. It is understood in the art that an oligonucleotide need not be 100% complementary to its target DNA sequence to be specifically hybridizable. An oligonucleotide is specifically hybridizable when there is a sufficient degree of complementarity to avoid non-specific binding of the oligonucleotide to non-target sequences under conditions in which specific binding is desired, i.e., under physiological conditions in the case of in vivo assays or therapeutic treatment, and in the case of in vitro assays, under conditions in which the assays are performed.

Antisense oligonucleotides are commonly used as research reagents, diagnostic aids, and therapeutic agents. For example, antisense oligonucleotides, which are able to inhibit gene expression with exquisite specificity, are often used by those of ordinary skill to elucidate the function of particular genes, for example to distinguish between the functions of various members of a biological pathway. This specific inhibitory effect has, therefore, been harnessed by those skilled in the art for research uses. The specificity and sensitivity of oligonucleotides is also harnessed by those of skill in the art for therapeutic uses.

Modified Linkages: Specific examples of some preferred modified oligonucleotides envisioned for this invention include those containing phosphorothioates, phosphotriesters, methyl phosphonates, short chain alkyl or cycloalkyl intersugar linkages or short chain heteroatomic or heterocyclic intersugar linkages. Most preferred are oligonucleotides with phosphorothioates and those with $CH_2$—NH—O—$CH_2$, $CH_2$—N($CH_3$)—O—$CH_2$ [known as a methylene(methylimino) or MMI backbone], $CH_2$—O—N($CH_3$)—$CH_2$, $CH_2$—N($CH_3$)—N($CH_3$)—$CH_2$ and O—N($CH_3$)—$CH_2$—$CH_2$ backbones, wherein the native phosphodiester backbone is represented as O—P—O—$CH_2$). Also preferred are oligonucleotides having morpholino backbone structures (Summerton and Weller, U.S. Pat. No. 5,034,506). Further preferred are oligonucleotides with NR—C(*)—$CH_2$—$CH_2$, $CH_2$—NR—C(*)—$CH_2$, $CH_2$—$CH_2$—NR—C(*), C(*)—NR—$CH_2$—$CH_2$ and $CH_2$—C(*)—NR—$CH_2$ backbones, wherein "*" represents O or S (known as amide backbones; DeMesmaeker et al., WO 92/20823, published Nov. 26, 1992). In other preferred embodiments, such as the peptide nucleic acid (PNA) backbone, the phosphodiester backbone of the oligonucleotide is replaced with a polyamide backbone, the nucleobases being bound directly or indirectly to the aza nitrogen atoms of the polyamide backbone (Nielsen et al., *Science*, 1991, 254, 1497; U.S. Pat. No. 5,539,082).

Modified Nucleobases: The oligonucleotides of the invention can additionally or alternatively include nucleobase modifications or substitutions. As used herein, "unmodified" or "natural" nucleobases include adenine (A), guanine (G), thymine (T), cytosine (C) and uracil (U). Modified nucleobases include nucleobases found only infrequently or transiently in natural nucleic acids, e.g., hypoxanthine, 6-methyladenine, 5-methylcytosine, 5-hydroxymethylcytosine (HMC), glycosyl HMC and gentiobiosyl HMC, as well synthetic nucleobases, e.g., 2-aminoadenine, 2-thiouracil, 2-thiothymine, 5-bromouracil, 5-hydroxymethyluracil, 8-azaguanine, 7-deazaguanine, $N^6$(6-aminohexyl)adenine and 2,6-diaminopurine (Kornberg, A., DNA Replication, W.H. Freeman & Co., San Francisco, 1980, pages 75-77; Gebeyehu, G., et al. *Nucleic Acids Res.*, 1987, 15, 4513).

Sugar Modifications Modified oligonucleotides can also contain one or more substituted sugar moieties. Preferred oligonucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl can be substituted or unsubstituted $C_1$ to $C_{10}$ alkyl or $C_2$ to $C_{10}$ alkenyl and alkynyl. Particularly preferred are $O[(CH_2)_nO]_mCH_3$, $O(CH_2)_nOCH_3$, $O(CH_2)_nNH_2$, $O(CH_2)_nCH_3$, $O(CH_2)_nONH_2$, and $O(CH_2)_nON[(CH_2)_nCH_3)]_2$, where n and m are from 1 to about 10. Other preferred oligonucleotides comprise one of the following at the 2' position: $C_1$ to $C_{10}$ lower alkyl, substituted lower alkyl, alkaryl, aralkyl, O-alkaryl or O-aralkyl, SH, $SCH_3$, OCN, Cl, Br, CN, $CF_3$, $OCF_3$, $SOCH_3$, $SO_2CH_3$, $ONO_2$, $NO_2$, $N_3$, $NH_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes an alkoxyalkoxy group, 2'-methoxyethoxy(2'-O—$CH_2CH_2OCH_3$, also known as 2'-O-(2-methioxyethyl) or 2'-MOE) (Martin et al., *Helv. Chim. Acta*, 1995, 78, 486-504). Further preferred modifications include 2'-dimethylaminooxyethoxy, i.e., a 2'-O$(CH_2)_2$ON$(CH_3)_2$ group, also known as 2'-DMAOE and 2'-dimethylaminoethoxyethoxy, i.e., 2'-O—$CH_2$—O—$CH_2$—N$(CH_3)_2$.

Other preferred modifications include 2'-methoxy(2'-O—$CH_3$), 2'-aminopropoxy(2'-O$CH_2CH_2CH_2NH_2$) and 2'-fluoro (2'-F). Similar modifications can also be made at other positions on the oligonucleotide, particularly the 3' position of the sugar on the 3' terminal nucleotide or in 2'-5' linked oligonucleotides and the 5' position of 5' terminal nucleotide. Oligonucleotides can also have sugar mimetics such as cyclobutyl moieties in place of the pentofuranosyl sugar. Representative United States patents that teach the preparation of such modified sugar structures include, but are not limited to, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference.

Other Modifications: Similar modifications can also be made at other positions on the oligonucleotide, particularly the 3' position of the sugar on the 3' terminal nucleotide and the 5' position of 5' terminal nucleotide. The 5' and 3' termini of an oligonucleotide can also be modified to serve as points of chemical conjugation of, e.g., lipophilic moieties (see immediately subsequent paragraph), intercalating agents (Kuyavin et al., WO 96/32496, published Oct. 17, 1996; Nguyen et al., U.S. Pat. No. 4,835,263, issued Can 30, 1989) or hydroxyalkyl groups (Helene et al., WO 96/34008, published Oct. 31, 1996).

Other positions within an oligonucleotide of the invention can be used to chemically link thereto one or more effector groups to form an oligonucleotide conjugate. An "effector group" is a chemical moiety that is capable of carrying out a particular chemical or biological function. Examples of such effector groups include, but are not limited to, an RNA cleaving group, a reporter group, an intercalator, a group for improving the pharmacokinetic properties of an oligonucleotide, or a group for improving the pharmacodynamic properties of an oligonucleotide and other substituents having similar properties. A variety of chemical linkers can be used to conjugate an effector group to an oligonucleotide of the invention. As an example, U.S. Pat. No. 5,578,718 to Cook et al. discloses methods of attaching an alkylthio linker, which can be further derivatized to include additional groups, to ribofuranosyl positions, nucleosidic base positions, or on internucleoside linkages. Additional methods of conjugating oligonucleotides to various effector groups are known in the art; see, e.g., *Protocols for Oligonucleotide Conjugates* (*Methods in Molecular Biology*, Volume 26) Agrawal, S., ed., Humana Press, Totowa, N.J., 1994.

Another preferred additional or alternative modification of the oligonucleotides of the invention involves chemically linking to the oligonucleotide one or more lipophilic moieties which enhance the cellular uptake of the oligonucleotide. Such lipophilic moieties can be linked to an oligonucleotide at several different positions on the oligonucleotide. Some preferred positions include the 3' position of the sugar of the 3' terminal nucleotide, the 5' position of the sugar of the 5' terminal nucleotide, and the 2' position of the sugar of any nucleotide. The $N^6$ position of a purine nucleobase can also be utilized to link a lipophilic moiety to an oligonucleotide of the invention (Gebeyehu, G., et al., *Nucleic Acids Res.*, 1987, 15, 4513). Such lipophilic moieties include but are not limited to a cholesteryl moiety (Letsinger et al., *Proc. Natl. Acad. Sci. U.S.A.*, 1989, 86, 6553), cholic acid (Manoharan et al., *Bioorg. Med. Chem. Let.*, 1994, 4, 1053), a thioether, e.g., hexyl-S-tritylthiol (Manoharan et al., *Ann. N.Y. Acad. Sci.*, 1992, 660, 306; Manoharan et al., *Bioorg. Med. Chem. Let.*, 1993, 3, 2765), a thiocholesterol (Oberhauser et al., *Nucl. Acids Res.*, 1992, 20, 533), an aliphatic chain, e.g., dodecandiol or undecyl residues (Saison-Behmoaras et al., *EMBO J.*, 1991, 10, 111; Kabanov et al., *FEBS Lett.*, 1990, 259, 327; Svinarchuk et al., *Biochimie*, 1993, 75, 49), a phospholipid, e.g., di-hexadecyl-rac-glycerol or triethylammonium 1,2-di-O-hexadecyl-rac-glycero-3-H-phosphonate (Manoharan et al, *Tetrahedron Lett.*, 1995, 36, 3651; Shea et al, *Nucl. Acids Res.*, 1990, 18, 3777), a polyamine or a polyethylene glycol chain (Manoharan et al., *Nucleosides & Nucleotides*, 1995, 14, 969), or adamantane acetic acid (Manoharan et al., *Tetrahedron Lett.*, 1995, 36, 3651), a palmityl moiety (Mishra et al., *Biochim. Biophys. Acta*, 1995, 1264, 229), or an octadecylamine or hexylamino-carbonyl-oxycholesterol moiety (Crooke et al., *J. Pharmacol. Exp. Ther.*, 1996, 277, 923). Oligonucleotides comprising lipophilic moieties, and methods for preparing such oligonucleotides, are disclosed in U.S. Pat. Nos. 5,138,045, 5,218,105 and 5,459,255.

The present invention also includes oligonucleotides that are substantially chirally pure with regard to particular positions within the oligonucleotides. Examples of substantially chirally pure oligonucleotides include, but are not limited to, those having phosphorothioate linkages that are at least 75% Sp or Rp (Cook et al., U.S. Pat. No. 5,587,361) and those having substantially chirally pure (Sp or Rp) alkylphosphonate, phosphoamidate or phosphotriester linkages (Cook, U.S. Pat. Nos. 5,212,295 and 5,521,302).

Chimeric Oligonucleotides: The present invention also includes oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide can serve as a substrate for enzymes capable of cleaving RNA:DNA or RNA:RNA hybrids. By way of example, RNase H is a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. By way of example, such "chimeras" can be "gapmers," i.e., oligonucleotides in which a central portion (the "gap") of the oligonucleotide serves as a substrate for, e.g., RNase H, and the 5' and 3' portions (the "wings") are modified in such a fashion so as to have greater affinity for the target RNA molecule but are unable to support nuclease activity (e.g., 2'-fluoro- or 2'-methoxyethoxy-substituted). Other chimeras include "wingmers," that is, oligonucleotides in which the 5' portion of the oligonucleotide serves as a substrate for, e.g., RNase H, whereas the 3' portion is modified in such a fashion so as to have greater affinity for the target RNA molecule but is unable to support nuclease activity (e.g., 2'-fluoro- or 2'-methoxyethoxy-substituted), or vice-versa.

Synthesis: The oligonucleotides used in accordance with this invention can be conveniently and routinely made through the well-known technique of solid phase synthesis. Equipment for such synthesis is sold by several vendors including, for example, Applied Biosystems (Foster City, Calif.). Any other means for such synthesis known in the art can additionally or alternatively be employed. It is also known to use similar techniques to prepare other oligonucleotides such as the phosphorothioates and alkylated derivatives.

Teachings regarding the synthesis of particular modified oligonucleotides can be found in the following U.S. patents or pending patent applications, each of which is commonly assigned with this application: U.S. Pat. Nos. 5,138,045 and 5,218,105, drawn to polyamine conjugated oligonucleotides; U.S. Pat. No. 5,212,295, drawn to monomers for the preparation of oligonucleotides having chiral phosphorus linkages; U.S. Pat. Nos. 5,378,825 and 5,541,307, drawn to oligonucleotides having modified backbones; U.S. Pat. No. 5,386,023, drawn to backbone modified oligonucleotides and the preparation thereofthrough reductive coupling; U.S. Pat. No. 5,457,191, drawn to modified nucleobases based on the 3-deazapurine ring system and methods of synthesis thereof; U.S. Pat. No. 5,459,255, drawn to modified nucleobases based on N-2 substituted purines; U.S. Pat. No. 5,521,302, drawn to processes for preparing oligonucleotides having chiral phosphorus linkages; U.S. Pat. No. 5,539,082, drawn to peptide nucleic acids; U.S. Pat. No. 5,554,746, drawn to oligonucleotides having β-lactam backbones; U.S. Pat. No. 5,571,902, drawn to methods and materials for the synthesis of oligonucleotides; U.S. Pat. No. 5,578,718, drawn to nucleosides having alkylthio groups, wherein such groups can be used as linkers to other moieties attached at any of a variety of positions of the nucleoside; U.S. Pat. Nos. 5,587,361 and 5,599,797, drawn to oligonucleotides having phosphorothioate linkages of high chiral purity; U.S. Pat. No. 5,506,351, drawn to processes for the preparation of 2'-O-alkyl guanosine and related compounds, including 2,6-diaminopurine compounds; U.S. Pat. No. 5,587,469, drawn to oligonucleotides having N-2 substituted purines; U.S. Pat. No. 5,587,470, drawn to oligonucleotides having 3-deazapurines; U.S. Pat. No. 5,223,168, issued Jun. 29, 1993, and U.S. Pat. No. 5,608,046, both drawn to conjugated 4'-desmethyl nucleoside analogs; U.S. Pat. Nos. 5,602,240, and 5,610,289, drawn to backbone modified oligonucleotide analogs; and U.S. patent application Ser. No. 08/383,666, filed Feb. 3, 1995, and U.S. Pat. No. 5,459,255, drawn to, inter alia, methods of synthesizing 2'-fluoro-oligonucleotides.

5-methyl-cytosine: In 2'-methoxyethoxy-modified oligonucleotides, 5-methyl-2'-methoxyethoxy-cytosine residues are used and are prepared as follows. 2,2'-Anhydro[1-(β-D- arabinofuranosyl)-5-methyluridine]: 5-Methyluridine (ribosylthymine, commercially available through Yamasa, Choshi, Japan) (72.0 g, 0.279 M), diphenylcarbonate (90.0 g, 0.420 M) and sodium bicarbonate (2.0 g, 0.024 M) were added to DMF (300 mL). The mixture was heated to reflux, with stirring, allowing the evolved carbon dioxide gas to be released in a controlled manner. After 1 hour, the slightly darkened solution was concentrated under reduced pressure. The resulting syrup was poured into diethylether (2.5 L), with stirring. The product formed a gum. The ether was decanted and the residue was dissolved in a minimum amount of methanol (ca. 400 mL). The solution was poured into fresh ether (2.5 L) to yield a stiff gum. The ether was decanted and the gum was dried in a vacuum oven (60?C at 1 mm Hg for 24 h) to give a solid which was crushed to a light tan powder (57 g, 85% crude yield). The material was used as is for further reactions. 2'-O-Methoxyethyl-5-methyluridine: 2,2'-Anhydro-5-methyluridine (195 g, 0.81 M), tris(2-methoxyethyl)borate (231 g, 0.98 M) and 2-methoxyethanol (1.2 L) were added to a 2 L stainless steel pressure vessel and placed in a pre-heated oil bath at 160?C. After heating for 48 hours at 155-160?C, the vessel was opened and the solution evaporated to dryness and triturated with MeOH (200 mL). The residue was suspended in hot acetone (1 L). The insoluble salts were filtered, washed with acetone (150 mL) and the filtrate evaporated. The residue (280 g) was dissolved in $CH_3CN$ (600 mL) and evaporated. A silica gel column (3 kg) was packed in $CH_2Cl_2$/acetone/MeOH (20:5:3) containing 0.5% $Et_3NH$. The residue was dissolved in $CH_2Cl_2$ (250 mL) and adsorbed onto silica (50 g) prior to loading onto the column. The product was eluted with the packing solvent to give 160 g (63%) of product. 2'-O-Methoxyethyl-5'-O-dimethoxytrityl-5-methyluridine: 2'-O-Methoxyethyl-5-methyluridine (160 g, 0.506 M) was co-evaporated with pyridine (250 mL) and the dried residue dissolved in pyridine (1.3 L). A first aliquot of dimethoxytrityl chloride (94.3 g, 0.278 M) was added and the mixture stirred at room temperature for one hour. A second aliquot of dimethoxytrityl chloride (94.3 g, 0.278 M) was added and the reaction stirred for an additional one hour. Methanol (170 mL) was then added to stop the reaction. HPLC showed the presence of approximately 70% product. The solvent was evaporated and triturated with $CH_3CN$ (200 mL). The residue was dissolved in $CHCl_3$ (1.5 L) and extracted with 2×500 mL of saturated $NaHCO_3$ and 2×500 mL of saturated NaCl. The organic phase was dried over $Na_2SO_4$, filtered and evaporated. 275 g of residue was obtained. The residue was purified on a 3.5 kg silica gel column, packed and eluted with EtOAc/Hexane/Acetone (5:5:1) containing 0.5% $Et_3NH$. The pure fractions were evaporated to give 164 g of product. Approximately 20 g additional was obtained from the impure fractions to give a total yield of 183 g (57%). 3'-O-Acetyl-2'-O-methoxyethyl-5'-O-dimethoxytrityl-5-methyluridine: 2'-O-Methoxyethyl-5'-O-dimethoxytrityl-5-methyluridine (106 g, 0.167 M), DMF/pyridine (750 mL of a 3:1 mixture prepared from 562 mL of DMF and 188 mL of pyridine) and acetic anhydride (24.38 mL, 0.258 M) were combined and stirred at room temperature for 24 hours. The reaction was monitored by tlc by first quenching the tlc sample with the addition of MeOH. Upon completion of the reaction, as judged by tlc, MeOH (50 mL) was added and the mixture evaporated at 35?C. The residue was dissolved in $CHCl_3$ (800 mL) and extracted with 2×200 mL of saturated sodium bicarbonate and 2×200 mL of saturated NaCl. The water layers were back extracted with 200 mL of $CHCl_3$. The combined organics were dried with sodium sulfate and evaporated to give 122 g of residue (approximately 90% product). The residue was purified on a 3.5 kg silica gel column and eluted using EtOAc/Hexane (4:1). Pure product fractions were evaporated to yield 96 g (84%). 3'-O-Acetyl-2'-O-methoxyethyl-5'-O-dimethoxytrityl-5-methyl-4-triazoleuridine: A first solution was prepared by dissolving 3'-O-acetyl-2'-O-methoxyethyl-5'-O-dimethoxytrityl-5-methyluridine (96 g, 0.144 M) in $CH_3CN$ (700 mL) and set aside. Triethylamine (189 mL, 1.44 M) was added to a solution of triazole (90 g, 1.3 M) in $CH_3CN$ (1 L), cooled to −5?C and stirred for 0.5 h using an overhead stirrer. $POCl_3$ was added dropwise, over a 30 minute period, to the stirred solution maintained at 0-10?C, and the resulting mixture stirred for an additional 2 hours. The first solution was added dropwise, over a 45 minute period, to the later solution. The resulting reaction mixture was stored overnight in a cold room. Salts were filtered from the reaction mixture and the solution was evaporated. The residue was dissolved in EtOAc (1 L) and the insoluble solids were removed by filtration. The filtrate was washed with 1×300 mL of $NaHCO_3$ and 2×300 mL of saturated NaCl, dried over sodium sulfate and evaporated. The residue was triturated with EtOAc to give the title compound. 2'-O-Methoxyethyl-5'-O-dimethoxytrityl-5-methylcytidine: A solution of 3'-O-acetyl-2'-O-methoxyethyl-5'-O-dimethoxytrityl-5-methyl-4-triazoleuridine (103 g, 0.141 M) in dioxane (500 mL) and $NH_4OH$ (30 mL) was stirred at room temperature for 2 hours. The dioxane solution was evaporated and the residue azeotroped with MeOH (2×200 mL). The residue was dissolved in MeOH (300 mL) and transferred to a 2 liter stainless steel pressure vessel. Methanol (400 mL) saturated with $NH_3$ gas was added and the vessel heated to 100?C for 2 hours (thin layer chromatography, tlc, showed complete conversion). The vessel contents were evaporated to dryness and the residue was dissolved in EtOAc (500 mL) and washed once with saturated NaCl (200 mL). The organics were dried over sodium sulfate and the solvent was evaporated to give 85 g (95%) of the title compound. $N^4$-Benzoyl-2'-O-methoxyethyl-5'-O-dimethoxytrityl-5-methylcytidine: 2'-O-Methoxyethyl-5'-O-dimethoxytrityl-5-methylcytidine (85 g, 0.134 M) was dissolved in DMF (800 mL) and benzoic anhydride (37.2 g, 0.165 M) was added with stirring. After stirring for 3 hours, tlc showed the reaction to be approximately 95% complete. The solvent was evaporated and the residue azeotroped with MeOH (200 mL). The residue was dissolved in $CHCl_3$ (700 mL) and extracted with saturated $NaHCO_3$ (2×300 mL) and saturated NaCl (2×300 mL), dried over $MgSO_4$ and evaporated to give a residue (96 g). The residue was chromatographed on a 1.5 kg silica column using EtOAc/Hexane (1:1) containing 0.5% $Et_3NH$ as the eluting solvent. The pure product fractions were evaporated to give 90 g (90%) of the title compound. $N^4$-Benzoyl-2'-O-methoxyethyl-5'-O-dimethoxytrityl-5-methylcytidine-3'-amidite: $N^4$-Benzoyl-2'-O-methoxyethyl-5'-O-dimethoxytrityl-5-methylcytidine (74 g, 0.10 M) was dissolved in $CH_2Cl_2$ (1 L). Tetrazole diisopropylamine (7.1 g) and 2-cyanoethoxy-tetra(isopropyl)-phosphite (40.5 mL, 0.123 M) were added with stirring, under a nitrogen atmosphere. The resulting mixture was stirred for 20 hours at room temperature (tlc showed the reaction to be 95% complete). The reaction mixture was extracted with saturated $NaHCO_3$ (1×300 mL) and saturated NaCl (3×300 mL). The aqueous washes were back-extracted with $CH_2Cl_2$ (300 mL), and the extracts were combined, dried over $MgSO_4$ and concentrated. The residue obtained was chromatographed on a 1.5 kg silica column using EtOAc\Hexane (3:1) as the eluting solvent. The pure fractions were combined to give 90.6 g (87%) of the title compound. 2'-O-(Aminooxyethyl) nucleoside amidites and 2'-O-(dimethylaminooxyethyl) nucleoside amidites 2'-(Dimethylaminooxyethoxy) nucleoside amidites 2'-(Dimethylaminooxyethoxy) nucleoside amidites [also known in the art as 2'-O-(dimethylaminooxyethyl) nucleoside amidites] are prepared as described in the following paragraphs. Adenosine, cytidine and guanosine nucleoside amidites are prepared similarly to the thymidine (5-methyluridine) except the exocyclic amines are protected with a benzoyl moiety in the case of adenosine and cytidine and with isobutyryl in the case of guanosine. 5'-O-tert-Butyldiphenylsilyl-$O^2$-2'-anhydro-5-methyluridine $O^2$-2'-anhydro-5-methyluridine (Pro. Bio. Sint., Varese, Italy, 100.0 g, 0.416 mmol), dimethylaminopyridine (0.66 g, 0.013 eq, 0.0054 mmol) were dissolved in dry pyridine (500 ml) at ambient temperature under an argon atmosphere and with mechanical stirring. tert-Butyldiphenylchlorosilane (125.8 g, 119.0 mL, 1.1 eq, 0.458 mmol) was added in one portion. The reaction was stirred for 16 h at ambient temperature. TLC(Rf 0.22, ethyl acetate) indicated a complete reaction. The solution was concentrated under reduced pressure to a thick oil. This was partitioned between dichloromethane (1 L) and saturated sodium bicarbonate (2×1 L) and brine (1 L). The organic layer was dried over sodium sulfate and concentrated under reduced pressure to a thick oil. The oil was dissolved in a 1:1 mixture of ethyl acetate and ethyl ether (600 mL) and the solution was cooled to −10° C. The resulting crystalline product was collected by filtration, washed with ethyl ether (3×200 mL) and dried (40° C., 1 mm Hg, 24 h) to 149 g (74.8%) of white solid. TLC and NMR were consistent with pure product. 5'-O-tert-Butyldiphenylsilyl-2'-O-(2-hydroxyethyl)-5-methyluridine In a 2 L stainless steel, unstirred pressure reactor was added borane in tetrahydrofuran (1.0 M, 2.0 eq, 622 mL). In the fume hood and with manual stirring, ethylene glycol (350 mL, excess) was added cautiously at first until the evolution of hydrogen gas subsided. 5'-O-tert-Butyldiphenysilyl-$O^2$-2'-anhydro-5-methyluridine (149 g, 0.311 mol) and sodium bicarbonate (0.074 g, 0.003 eq) were added with manual stirring. The reactor was sealed and heated in an oil bath until an internal temperature of 160° C. was reached and then maintained for 16 h (pressure<100 psig). The reaction vessel was cooled to ambient and opened. TLC(Rf 0.67 for desired product and Rf 0.82 for ara-T side product, ethyl acetate) indicated about 70% conversion to the product. In order to avoid additional side product formation, the reaction was stopped, concentrated under reduced pressure (10 to 1 mm Hg) in a warm water bath (40-100° C.) with the more extreme conditions used to remove the ethylene glycol. [Alternatively, once the low boiling solvent is gone, the remaining solution can be partitioned between ethyl acetate and water. The product will be in the organic phase.] The residue was purified by column chromatography (2 kg silica gel, ethyl acetate-hexanes gradient 1:1 to 4:1). The appropriate fractions were combined, stripped and dried to product as a white crisp foam (84 g, 50%), contaminated starting material (17.4 g) and pure reusable starting material 20 g. The yield based on starting material less pure recovered starting material was 58%. TLC and NMR were consistent with 99% pure product.

2'-O-([2-phthalimidoxy)ethyl]-5'-t-butyldiphenylsilyl-5-methyluridine

5'-O-tert-Butyldiphenylsilyl-2'-O-(2-hydroxyethyl)-5-methyluridine (20 g, 36.98 mmol) was mixed with triphenylphosphine (11.63 g, 44.36 mmol) and N-hydroxyphthalimide (7.24 g, 44.36 mmol). It was then dried over $P_2O_5$ under high vacuum for two days at 40?C. The reaction mixture was flushed with argon and dry THF (369.8 mL, Aldrich, sure seal bottle) was added to get a clear solution. Diethyl-azodicarboxylate (6.98 mL, 44.36 mmol) was added dropwise to the reaction mixture. The rate of addition is maintained such that resulting deep red coloration is just discharged before adding the next drop. After the addition was complete, the reaction was stirred for 4 hrs. By that time TLC showed the completion of the reaction (ethylacetate:hexane, 60:40). The solvent was evaporated in vacuum. Residue obtained was placed on a flash column and eluted with ethyl acetate:hexane (60:40), to get 2'-O-([2-phthalimidoxy)ethyl]-5'-t-butyldiphenylsilyl-5-methyluridine as white foam (21.819 g, 86%).

5'-O-tert-butyldiphenylsilyl-2'-O-[(2-formadoximinooxy)ethyl]-5-methyluridine

2'-O-([2-phthalimidoxy)ethyl]-5'-t-butyldiphenylsilyl-5-methyluridine (3.1 g, 4.5 mmol) was dissolved in dry $CH_2Cl_2$ (4.5 mL) and methylhydrazine (300 mL, 4.64 mmol) was added dropwise at −10?C to 0?C. After 1 h the mixture was filtered, the filtrate was washed with ice cold $CH_2Cl_2$ and the combined organic phase was washed with water, brine and dried over anhydrous $Na_2SO_4$. The solution was concentrated to get 2'-O-(aminooxyethyl) thymidine, which was then dissolved in MeOH (67.5 mL). To this formaldehyde (20% aqueous Solution, w/w, 1.1 eq.) was added and the resulting mixture was stirred for 1 h. Solvent was removed under vacuum; residue chromatographed to get 5'-O-tert-butyldiphenylsilyl-2'-O-[(2-formadoximinooxy)ethyl]-5-methyluridine as white foam (1.95 g, 78%).

5'-O-tert-Butyldiphenylsilyl-2'-O—[N,N-dimethylaminooxyethyl]-5-methyluridine

5'-O-tert-butyldiphenylsilyl-2'-O-[(2-formadoximinooxy)ethyl]-5-methyluridine (1.77 g, 3.12 mmol) was dissolved in a solution of 1M pyridinium p-toluenesulfonate (PPTS) in dry MeOH (30.6 mL). Sodium cyanoborohydride (0.39 g, 6.13 mmol) was added to this solution at 10?C under inert atmosphere. The reaction mixture was stirred for 10 minutes at 10?C. After that the reaction vessel was removed from the ice bath and stirred at room temperature for 2 h, the reaction monitored by TLC (5% MeOH in $CH_2Cl_2$). Aqueous $NaHCO_3$ solution (5%, 10 mL) was added and extracted with ethyl acetate (2×20 mL). Ethyl acetate phase was dried over anhydrous $Na_2SO_4$, evaporated to dryness. Residue was dissolved in a solution of 1 M PPTS in MeOH (30.6 mL). Formaldehyde (20% w/w, 30 mL, 3.37 mmol) was added and the reaction mixture was stirred at room temperature for 10 minutes. Reaction mixture cooled to 10?C in an ice bath, sodium cyanoborohydride (0.39 g, 6.13 mmol) was added and reaction mixture stirred at 10?C for 10 minutes. After 10 minutes, the reaction mixture was removed from the ice bath and stirred at room temperature for 2 hrs. To the reaction mixture 5% $NaHCO_3$ (25 mL) solution was added and extracted with ethyl acetate (2×25 mL). Ethyl acetate layer was dried over anhydrous $Na_2SO_4$ and evaporated to dryness. The residue obtained was purified by flash column chromatography and eluted with 5% MeOH in $CH_2Cl_2$ to get 5'-O-tert-butyldiphenylsilyl-2'-O—[N,N-dimethylaminooxyethyl]-5-methyluridine as a white foam (14.6 g, 80%).

2'-O-(dimethylaminooxyethyl)-5-methyluridine

Triethylamine trihydrofluoride (3.91 mL, 24.0 mmol) was dissolved in dry THF and triethylamine (1.67 mL, 12 mmol, dry, kept over KOH). This mixture of triethylamine-2HF was then added to 5'-O-tert-butyldiphenylsilyl-2'-O—[N,N-dimethylaminooxyethyl]-5-methyluridine (1.40 g, 2.4 mmol) and stirred at room temperature for 24 hrs. Reaction was monitored by TLC (5% MeOH in $CH_2Cl_2$). Solvent was removed under vacuum and the residue placed on a flash column and eluted with 10% MeOH in $CH_2Cl_2$ to get 2'-O-(dimethylaminooxyethyl)-5-methyluridine (766 mg, 92.5%).

5'-O-DMT-2'-O-(dimethylaminooxyethyl)-5-methyluridine

2'-O-(dimethylaminooxyethyl)-5-methyluridine (750 mg, 2.17 mmol) was dried over $P_2O_5$ under high vacuum overnight at 40?C. It was then co-evaporated with anhydrous pyridine (20 mL). The residue obtained was dissolved in pyridine (1 mL) under argon atmosphere. 4-dimethylaminopyridine (26.5 mg, 2.60 mmol), 4,4'-dimethoxytrityl chloride (880 mg, 2.60 mmol) was added to the mixture and the reaction mixture was stirred at room temperature until all of the starting material disappeared. Pyridine was removed under vacuum and the residue chromatographed and eluted with 10% MeOH in $CH_2Cl_2$ (containing a few drops of pyridine) to get 5'-O-DMT-2'-O-(dimethylaimino-oxyethyl)-5-methyluridine (1.13 g, 80%).

5'-O-DMT-2'-O-(2-N,N-dimethylaminooxyethyl)-5-methyluridine-3'-[(2-cyanoethyl)-N,N-diisopropylphosphoramidite]

5'-O-DMT-2'-O-(dimethylaminooxyethyl)-5-methyluridine (1.08 g, 1.67 mmol) was co-evaporated with toluene (20 mL). To the residue N,N-diisopropylamine tetrazonide (0.29 g, 1.67 mmol) was added and dried over $P_2O_5$ under high vacuum overnight at 40?C. Then the reaction mixture was dissolved in anhydrous acetonitrile (8.4 mL) and 2-cyanoethyl-N,N,N$^1$,N$^1$-tetraisopropylphosphoramidite (2.12 mL, 6.08 mmol) was added. The reaction mixture was stirred at ambient temperature for 4 hrs under inert atmosphere. The progress of the reaction was monitored by TLC (hexane:ethyl acetate 1:1). The solvent was evaporated, then the residue was dissolved in ethyl acetate (70 mL) and washed with 5% aqueous $NaHCO_3$ (40 mL). Ethyl acetate layer was dried over anhydrous $Na_2SO_4$ and concentrated. Residue obtained was chromatographed (ethyl acetate as eluent) to get 5'-O-DMT-2'-O-(2-N,N-dimethylaminooxyethyl)-5-methyluridine-3'-[(2-cyanoethyl)-N,N-diisopropylphosphoramidite] as a foam (1.04 g, 74.9%).

2'-(Aminooxyethoxy) nucleoside amidites

2'-(Aminooxyethoxy) nucleoside amidites [also known in the art as 2'-O-(aminooxyethyl) nucleoside amidites] are prepared as described in the following paragraphs. Adenosine, cytidine and thymidine nucleoside amidites are prepared similarly.

N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite]

The 2'-O-aminooxyethyl guanosine analog can be obtained by selective 2'-O-alkylation of diaminopurine riboside. Multigram quantities of diaminopurine riboside can be purchased from Schering AG (Berlin) to provide 2'-O-(2-ethylacetyl) diaminopurine riboside along with a minor amount of the 3'-O-isomer. 2'-O-(2-ethylacetyl) diaminopurine riboside can be resolved and converted to 2'-O-(2-ethylacetyl)guanosine by treatment with adenosine deaminase. (McGee, D. P. C., Cook, P. D., Guinosso, C. J., WO 94/02501 A1940203.) Standard protection procedures should afford 2'-O-(2-ethylacetyl)-5'-O-(4,4'-dimethoxytrityl)guanosine and 2-N-isobutyry-6-O-diphenylcarbamoyl-2'-O-(2-ethylacetyl)-5'-O-(4,4'-dimethoxytrityl)guanosine which can be reduced to provide 2-N-isobutyryl-6-O-diphenylcarbamoyl-2'-O-(2-ethylacetyl)-5'-O-(4,4'-dimethoxytrityl)guanosine. As before the hydroxyl group can be displaced by N-hydroxyphthalimide via a Mitsunobu reaction, and the protected nucleoside can phosphitylated as usual to yield 2-N-isobutyryl-6-O-diphenylcarbamoyl-2'-O-(2-ethylacetyl)-5'-O-(4, 4'-dimethoxytrityl)guanosine-3'-[(2-cyanoethyl)-N,N-diisopropylphosphoramidite].

Bioequivalents: The compounds of the invention encompass any pharmaceutically acceptable salts, esters, or salts of such esters, or any other compound which, upon administration to an animal including a human, is capable of providing (directly or indirectly) the biologically active metabolite or residue thereof. Accordingly, for example, the disclosure is also drawn to "prodrugs" and "pharmaceutically acceptable salts" of the oligonucleotides of the invention, pharmaceutically acceptable salts of such prodrugs, and other bioequivalents.

Oligonucleotide Prodrugs: The oligonucleotides of the invention can additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides of the invention are prepared as SATE [(S-acetyl-2-thioethyl)phosphate] derivatives according to the methods disclosed in WO 93/24510 to Gosselin et al., published Dec. 9, 1993.

Pharmaceutically Acceptable Salts: The term Apharmaceutically acceptable salts" refers to physiologically and pharmaceutically acceptable salts of the oligonucleotides of the invention: i.e., salts that retain the desired biological activity of the parent compound and do not impart undesired toxicological effects thereto.

Pharmaceutically acceptable base addition salts are formed with metals or amines, such as alkali and alkaline earth metals or organic amines. Examples of metals used as cations are sodium, potassium, magnesium, calcium, and the like. Examples of suitable amines are N,N'-dibenzylethylenediamine, chloroprocaine, choline, diethanolamine, dicyclohexylamine, ethylenediamine, N-methylglucamine, and procaine (see, for example, Berge et al., "Pharmaceutical Salts," *J. of Pharma Sci.*, 1977, 66, 1). The base addition salts of said acidic compounds are prepared by contacting the free acid form with a sufficient amount of the desired base to produce the salt in the conventional manner. The free acid form can be regenerated by contacting the salt form with an acid and isolating the free acid in the conventional manner. The free acid forms differ from their respective salt forms somewhat in certain physical properties such as solubility in polar solvents, but otherwise the salts are equivalent to their respective free acid for purposes of the present invention. As used herein, a "pharmaceutical addition salt" includes a pharmaceutically acceptable salt of an acid form of one of the components of the compositions of the invention. These include organic or inorganic acid salts of the amines. Preferred acid salts are the hydrochlorides, acetates, salicylates, nitrates and phosphates. Other suitable pharmaceutically acceptable salts are well known to those skilled in the art and include basic salts of a variety of inorganic and organic acids, such as, for example, with inorganic acids, such as for example hydrochloric acid, hydrobromic acid, sulfuric acid or phosphoric acid; with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, lactic acid, oxalic acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid; and with amino acids, such as the alpha-amino acids involved in the synthesis of proteins in nature, for example glutamic acid or aspartic acid, and also with phenylacetic acid, methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, naphthalene-1,5-disulfonic acid, 2- or 3-phosphoglycerate, glucose-6-phosphate, N-cyclohexylsulfamic acid (with the formation of cyclamates), or with other acid organic compounds, such as ascorbic acid. Pharmaceutically acceptable salts of compounds can also be prepared with a pharmaceutically acceptable cation. Suitable pharmaceutically acceptable cations are well known to those skilled in the art and include alkaline, alkaline earth, ammonium and quaternary ammonium cations. Carbonates or hydrogen carbonates are also possible.

For oligonucleotides, preferred examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Exemplary Utilities of the Invention: The oligonucleotides of the present invention specifically hybridize to nucleic acids (e.g., mRNAs) encoding a JNK1 protein. The oligonucleotides of the present invention can be utilized as therapeutic compounds, as diagnostic tools or research reagents that can be incorporated into kits, and in purifications and cellular product preparations, as well as other methodologies, which are appreciated by persons of ordinary skill in the art.

Assays and Diagnostic Applications: The oligonucleotides of the present invention can be used to detect the presence of JNK1 protein-specific nucleic acids in a cell or tissue sample. For example, radiolabeled oligonucleotides can be prepared by $^{32}$P labeling at the 5' end with polynucleotide kinase. (Sambrook et al., *Molecular Cloning. A Laboratory Manual*, Cold Spring Harbor Laboratory Press, 1989, Volume 2, pg. 10.59.) Radiolabeled oligonucleotides are then contacted with cell or tissue samples suspected of containing JNK1 protein message RNAs (and thus JNK1 proteins), and the samples are washed to remove unbound oligonucleotide. Radioactivity remaining in the sample indicates the presence of bound oligonucleotide, which in turn indicates the presence of nucleic acids complementary to the oligonucleotide, and can be quantitated using a scintillation counter or other routine means. Expression of nucleic acids encoding these proteins is thus detected.

Radiolabeled oligonucleotides of the present invention can also be used to perform autoradiography of tissues to determine the localization, distribution and quantitation of JNK1 proteins for research, diagnostic or therapeutic purposes. In such studies, tissue sections are treated with radiolabeled oligonucleotide and washed as described above, then exposed to photographic emulsion according to routine autoradiography procedures. The emulsion, when developed, yields an image of silver grains over the regions expressing a JNK1 protein gene. Quantitation of the silver grains permits detection of the expression of mRNA molecules encoding these proteins and permits targeting of oligonucleotides to these areas.

Analogous assays for fluorescent detection of expression of JNK1 protein nucleic acids can be developed using oligonucleotides of the present invention which are conjugated with fluorescein or other fluorescent tags instead of radiolabeling. Such conjugations are routinely accomplished during solid phase synthesis using fluorescently-labeled amidites or controlled pore glass (CPG) columns. Fluorescein-labeled amidites and CPG are available from, e.g., Glen Research, Sterling Va. Other means of labeling oligonucleotides are known in the art (see, e.g., Ruth, Chapter 6 *In: Methods in Molecular Biology*, Vol. 26: *Protocols for Oligonucleotide Conjugates*, Agrawal, ed., Humana Press Inc., Totowa, N.J., 1994, pages 167-185).

Kits for detecting the presence or absence of expression of a JNK1 protein can also be prepared. Such kits include an oligonucleotide targeted to an appropriate gene, i.e., a gene encoding a JNK1 protein. Appropriate kit and assay formats, such as, e.g., "sandwich" assays, are known in the art and can easily be adapted for use with the oligonucleotides of the invention. Hybridization of the oligonucleotides of the invention with a nucleic acid encoding a JNK1 protein can be detected by means known in the art. Such means can include conjugation of an enzyme to the oligonucleotide, radiolabelling of the oligonucleotide or any other suitable detection systems.

Protein Purifications: The oligonucleotides of the invention are also useful for the purification of specific Jun kinase proteins from cells that normally express a set of JNK proteins which are similar to each other in terms of their polypeptide sequences and biochemical properties. As an example, the purification of a JNK1 protein from cells that expresses JNK1, JNK2 and JNK3 proteins can be enhanced by first treating such cells with oligonucleotides that inhibit the expression of JNK2 and JNK3 and/or with oligonucleotides that increase the expression of JNK, because such treatments will increase the relative ratio of JNK1 relative to JNK2 and JNK3. As a result, the yield of JNK1 from subsequent purification steps will be improved as the amount of the biochemically similar (and thus likely to contaminate) JNK2 and JNK3 proteins in extracts prepared from cells so treated will be diminished.

Biologically Active Oligonucleotides: The invention is also drawn to the administration of oligonucleotides having biological activity to cultured cells, isolated tissues and organs and animals. By "having biological activity," it is meant that the oligonucleotide functions to modulate the expression of one or more genes in cultured cells, isolated tissues or organs and/or animals. Such modulation can be achieved by an antisense oligonucleotide by a variety of mechanisms known in the art, including but not limited to transcriptional arrest; effects on RNA processing (capping, polyadenylation and splicing) and transportation; enhancement of cellular degradation of the target nucleic acid; and translational arrest (Crooke et al., *Exp. Opin. Ther. Patents,* 1996 6, 855).

In an animal other than a human, the compositions and methods of the invention can be used to study the function of one or more genes in the animal. For example, antisense oligonucleotides have been systemically administered to rats in order to Study the role of the N-methyl-D-aspartate receptor in neuronal death, to mice in order to investigate the biological role of protein kinase C-a, and to rats in order to examine the role of the neuropeptide Y1 receptor in anxiety (Wahlestedt et al., *Nature,* 1993, 363, 260; Dean et al., *Proc. Natl. Acad. Sci. U.S.A.,* 1994, 91, 11762; and Wahlestedt et al., *Science,* 1993, 259, 528, respectively). In instances where complex families of related proteins are being investigated, "antisense knockouts" (i.e., inhibition of a gene by systemic administration of antisense oligonucleotides) can represent the most accurate means for examining a specific member of the family (see, generally, Albert et al., *Trends Pharmacol. Sci.,* 1994, 15, 250).

The compositions and methods of the invention also have therapeutic uses in an animal, including a human, having (i.e., suffering from), or known to be or suspected of being prone to having, a disease or disorder that is treatable in whole or in part with one or more nucleic acids. The term "therapeutic uses" is intended to encompass prophylactic, palliative and curative uses wherein the oligonucleotides of the invention are contacted with animal cells either in vivo or ex vivo. When contacted with animal cells ex vivo, a therapeutic use includes incorporating such cells into an animal after treatment with one or more oligonucleotides of the invention.

For therapeutic uses, an animal suspected of having a disease or disorder which can be treated or prevented by modulating the expression or activity of a JNK1 protein is, for example, treated by administering oligonucleotides in accordance with this invention. The oligonucleotides of the invention can be utilized in pharmaceutical compositions by adding an effective amount of an oligonucleotide to a suitable pharmaceutically acceptable carrier such as, e.g., a diluent. Workers in the field have identified antisense, triplex and other oligonucleotide compositions which are capable of modulating expression of genes implicated in viral, fungal and metabolic diseases. Antisense oligonucleotides have been safely administered to humans and several clinical trials are presently underway. It is thus established that oligonucleotides can be useful therapeutic instrumentalities that can be configured to be useful in treatment regimes for treatment of cells, tissues and animals, especially humans. The following U.S. patents demonstrate palliative, therapeutic and other methods utilizing antisense oligonucleotides. U.S. Pat. No. 5,135,917 provides antisense oligonucleotides that inhibit human interleukin-1 receptor expression. U.S. Pat. No. 5,098, 890 is directed to antisense oligonucleotides complementary to the c-myb oncogene and antisense oligonucleotide therapies for certain cancerous conditions. U.S. Pat. No. 5,087,617 provides methods for treating cancer patients with antisense oligonucleotides. U.S. Pat. No. 5,166,195 provides oligonucleotide inhibitors of Human Immunodeficiency Virus (HIV). U.S. Pat. No. 5,004,810 provides oligomers capable of hybridizing to herpes simplex virus Vmw65 mRNA and inhibiting replication. U.S. Pat. No. 5,194,428 provides antisense oligonucleotides having antiviral activity against influenza virus. U.S. Pat. No. 5,004,810 provides antisense oligonucleotides and methods using them to inhibit HTLV-III replication. U.S. Pat. No. 5,286,717 provides oligonucleotides having a complementary base sequence to a portion of an oncogene. U.S. Pat. No. 5,276,019 and U.S. Pat. No. 5,264,423 are directed to phosphorothioate oligonucleotide analogs used to prevent replication of foreign nucleic acids in cells. U.S. Pat. No. 4,689,320 is directed to antisense oligonucleotides as antiviral agents specific to cytomegalovirus (CMV). U.S. Pat. No. 5,098,890 provides oligonucleotides complementary to at least a portion of the mRNA transcript of the human c-myb gene. U.S. Pat. No. 5,242,906 provides antisense oligonucleotides useful in the treatment of latent Epstein-Barr virus (EBV) infections.

As used herein, the term "disease, condition or disorder" includes any abnormal condition of an organism or part that impairs normal physiological functioning; such as obesity and metabolic syndrome. As used herein, the term "prevention" means to delay or forestall onset or development of a condition or disease for a period of time from hours to days, preferably weeks to months. As used herein, the term "amelioration" means a lessening of at least one indicator of the severity of a condition or disease. The severity of indicators can be determined by subjective or objective measures which are known to those skilled in the art. As used herein, "treatment" means to administer a composition of the invention to effect an alteration or improvement of the disease or condition. Prevention, amelioration, and/or treatment can require administration of multiple doses at regular intervals, or prior to exposure to an agent (e.g., an allergen) to alter the course of the condition or disease. Moreover, a single agent can be used in a single individual for each prevention, amelioration, and treatment of a condition or disease sequentially, or concurrently. The term "a disease or disorder that is treatable in whole or in part with one or more nucleic acids" refers to a disease or disorder, as herein defined, the management, modulation or treatment thereof, and/or therapeutic, curative, palliative and/or prophylactic relief therefrom, can be provided via the administration of an antisense oligonucleotide.

Pharmaceutical Compositions: The formulation of pharmaceutical compositions comprising the oligonucleotides of the invention, and their subsequent administration, are believed to be within the skill of those in the art.

Therapeutic Considerations In general, for therapeutic applications, a patient (i.e., an animal, including a human, having or predisposed to a disease or disorder) is administered one or more oligonucleotides, in accordance with the invention in a pharmaceutically acceptable carrier in doses ranging from 0.01 ]g to 100 g per kg of body weight depending on the age of the patient and the severity of the disorder or disease state being treated. Further, the treatment regimen can last for a period of time which will vary depending upon the nature of the particular disease or disorder, its severity and the overall condition of the patient, and can extend from once daily to once every 20 years. In the context of the invention, the term "treatment regimen" is meant to encompass therapeutic, palliative and prophylactic modalities. Following treatment, the patient is monitored for changes in his/her condition and for alleviation of the symptoms of the disorder or disease state. The dosage of the nucleic acid can either be increased in the event the patient does not respond significantly to current dosage levels, or the dose can be decreased if an alleviation of the symptoms of the disorder or disease state is observed, or if the disorder or disease state has been ablated.

Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages can vary depending on the relative potency of individual oligonucleotides, and can generally be estimated based on $EC_{50}$s found to be effective in in vitro and in vivo animal models. In general, dosage is from 0.01 μg to 100 g per kg of body weight, and can be given once or more daily, weekly, monthly or yearly, or even once every 2 to 20 years. An optimal dosing schedule is used to deliver a therapeutically effective amount of the oligonucleotide being administered via a particular mode of administration.

The term "therapeutically effective amount," for the purposes of the invention, refers to the amount of oligonucleotide-containing pharmaceutical composition which is effective to achieve an intended purpose without undesirable side effects (such as toxicity, irritation or allergic response). Although individual needs can vary, determination of optimal ranges for effective amounts of pharmaceutical compositions is within the skill of the art. Human doses can be extrapolated from animal studies (Katocs et al., Chapter 27 In: Remington's Pharmaceutical Sciences, 18th Ed., Gennaro, ed., Mack Publishing Co., Easton, Pa., 1990). Generally, the dosage required to provide an effective amount of a pharmaceutical composition, which can be adjusted by one skilled in the art, will vary depending on the age, health, physical condition, weight, type and extent of the disease or disorder of the recipient, frequency of treatment, the nature of concurrent therapy (if any) and the nature and scope of the desired effect(s) (Nies et al., Chapter 3 In: Goodman & Gilman's The Pharmacological Basis of Therapeutics, 9th Ed., Hardman et al., Eds., McGraw-Hill, New York, N.Y., 1996).

As used herein, the term "high risk individual" is meant to refer to a subject for whom it has been determined, via, e.g., individual or family history or genetic testing, has a significantly higher than normal probability of being susceptible to the onset or recurrence of a disease or disorder. As art of treatment regimen for a high risk individual, the individual can be prophylactically treated to prevent the onset or recurrence of the disease or disorder. The term "prophylactically effective amount" is meant to refer to an amount of a pharmaceutical composition which produces an effect observed as the prevention of the onset or recurrence of a disease or disorder. Prophylactically effective amounts of a pharmaceutical composition are typically determined by the effect they have compared to the effect observed when a second pharmaceutical composition lacking the active agent is administered to a similarly situated individual.

Following successful treatment, it can be desirable to have the patient undergo maintenance therapy to prevent the recurrence of the disease state, wherein the nucleic acid is administered in maintenance doses, ranging from 0.01 μg to 100 g per kg of body weight, once or more daily, to once every 20 years. For example, in the case of in individual known or suspected of being prone to an autoimmune or inflammatory condition, prophylactic effects can be achieved by administration of preventative doses, ranging from 0.01 μg to 100 g per kg of body weight, once or more daily, to once every 20 years. In like fashion, a subject can be made less susceptible to an inflammatory condition that is expected to occur as a result of some medical treatment, e.g., graft versus host disease resulting from the transplantation of cells, tissue or an organ into the individual.

In some cases it can be more effective to treat a patient with an oligonucleotide of the invention in conjunction with other traditional therapeutic modalities in order to increase the efficacy of a treatment regimen. A treatment regimen encompasses therapeutic, palliative and prophylactic modalities. For example, a patient can be treated with conventional chemotherapeutic agents, particularly those used for tumor and cancer treatment. Examples of such chemotherapeutic agents include but are not limited to daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, vincristine, vinblastine, etoposide, trimetrexate, teniposide, cisplatin and diethylstilbestrol (DES). See, generally, *The Merck Manual of Diagnosis and Therapy*, 15th Ed., pp. 1206-1228, Berkow et al., Eds., Rahay, N.J., 1987). When used with the compounds of the invention, such chemotherapeutic agents can be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

In another preferred embodiment of the invention, a first antisense oligonucleotide targeted to a first JNK1 protein is used in combination with a second antisense oligonucleotide targeted to a second JNK protein in order to such JNK proteins to a more extensive degree than can be achieved when either oligonucleotide is used individually. In various embodiments of the invention, the first and second JNK proteins which are targeted by such oligonucleotides are identical, are different JNK proteins or are different isoforms of the same JNK protein.

Pharmaceutical Compositions: Pharmaceutical compositions for the non-parenteral administration of oligonucleotides can include sterile aqueous solutions which can also contain buffers, diluents and other suitable additives. Pharmaceutically acceptable organic or inorganic carrier substances suitable for non-parenteral administration which do not deleteriously react with oligonucleotides can be used. Suitable pharmaceutically acceptable carriers include, but are not limited to, water, salt solutions, alcohol, polyethylene glycols, gelatin, lactose, amylose, magnesium stearate, talc, silicic acid, viscous paraffin, hydroxymethylcellulose, polyvinylpyrrolidone and the like. The pharmaceutical compositions can be sterilized and, if desired, mixed with auxiliary agents, e.g., lubricants, preservatives, stabilizers, wetting agents, emulsifiers, salts for influencing osmotic pressure, buffers, colorings flavorings and/or aromatic substances and the like which do not deleteriously react with the oligonucleotide(s) of the pharmaceutical composition. Pharmaceutical compositions in the form of aqueous suspensions can contain substances which increase the viscosity of the suspension including, for example, sodium carboxymethylcellulose, sorbitol and/or dextran. Optionally, such suspensions can also contain stabilizers.

In one embodiment of the invention, an oligonucleotide is administered via the rectal mode. In particular, pharmaceutical compositions for rectal administration include foams, solutions (enemas) and suppositories. Rectal suppositories for adults are usually tapered at one or both ends and typically weigh about 2 g each, with infant rectal suppositories typically weighing about one-half as much, when the usual base, cocoa butter, is used (Block, Chapter 87 In: Remington's Pharmaceutical Sciences, 18th Ed., Gennaro, ed., Mack Publishing Co., Easton, Pa., 1990).

In a preferred embodiment of the invention, one or more oligonucleotides are administered via oral delivery. Pharmaceutical compositions for oral administration include powders or granules, suspensions or solutions in water or non-aqueous media, capsules, sachets, troches, tablets or SECs (soft elastic capsules or "caplets"). Thickeners, flavoring agents, diluents, emulsifiers, dispersing aids, carrier substances or binders can be desirably added to such pharmaceutical compositions. The use of such pharmaceutical compositions has the effect of delivering the oligonucleotide to the alimentary canal for exposure to the mucosa thereof. Accordingly, the pharmaceutical composition can comprise material effective in protecting the oligonucleotide from pH extremes of the stomach, or in releasing the oligonucleotide over time, to optimize the delivery thereof to a particular mucosal site. Enteric coatings for acid-resistant tablets, capsules and caplets are known in the art and typically include acetate phthalate, propylene glycol and sorbitan monoleate.

Various methods for producing pharmaceutical compositions for alimentary delivery are well known in the art. See, generally, Nairn, Chapter 83; Block, Chapter 87; Rudnic et al., Chapter 89; Porter, Chapter 90; and Longer et al., Chapter 91 In: Remington's Pharmaceutical Sciences, 18th Ed., Gennaro, ed., Mack Publishing Co., Easton, Pa., 1990. The oligonucleotides of the invention can be incorporated in a known manner into customary pharmaceutical compositions, such as tablets, coated tablets, pills, granules, aerosols, syrups, emulsions, suspensions and solutions, using inert, nontoxic, pharmaceutically acceptable carriers (excipients). The therapeutically active compound should in each case be present here in a concentration of about 0.5% to about 95% by weight of the total mixture, i.e., in amounts which are sufficient to achieve the stated dosage range. The pharmaceutical compositions are prepared, for example, by diluting the active compounds with pharmaceutically acceptable carriers, if appropriate using emulsifying agents and/or dispersing agents, and, for example, in the case where water is used as the diluent, organic solvents can be used as auxiliary solvents if appropriate. Pharmaceutical compositions can be formulated in a conventional manner using additional pharmaceutically acceptable carriers as appropriate. Thus, the compositions can be prepared by conventional means with additional excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrates (e.g., starch or sodium starch glycolate); or wetting agents (e.g., sodium lauryl sulfate). Tablets can be coated by methods well known in the art. The preparations can also contain flavoring, coloring and/or sweetening agents as appropriate.

The pharmaceutical compositions, which can conveniently be presented in unit dosage form, can be prepared according to conventional techniques well known in the pharmaceutical industry. Such techniques include the step of bringing into association the active ingredient(s) with the pharmaceutically acceptable carrier(s). In general the pharmaceutical compositions are prepared by uniformly and intimately bringing into association the active ingredient(s) with liquid excipients or finely divided solid excipients or both, and then, if necessary, shaping the product.

Pharmaceutical compositions of the present invention suitable for oral administration can be presented as discrete units such as capsules, cachets or tablets each containing predetermined amounts of the active ingredients; as powders or granules; as solutions or suspensions in an aqueous liquid or a non-aqueous liquid; or as oil-in-water emulsions or water-in-oil liquid emulsions. A tablet can be made by compression or molding, optionally with one or more accessory ingredients. Compressed tablets can be prepared by compressing in a suitable machine, the active ingredients in a free-flowing form such as a powder or granules, optionally mixed with a binder, lubricant, inert diluent, preservative, surface active or dispersing agent. Molded tablets can be made by molding in a suitable machine a mixture of the powdered compound moistened with an inert liquid diluent. The tablets can optionally be coated or scored and can be formulated so as to provide slow or controlled release of the active ingredients therein. Pharmaceutical compositions for parenteral, intrathecal or intraventricular administration, or colloidal dispersion systems, can include sterile aqueous solutions which can also contain buffers, diluents and other suitable additives.

Penetration Enhancers Pharmaceutical compositions comprising the oligonucleotides of the present invention can also include penetration enhancers in order to enhance the alimentary delivery of the oligonucleotides. Penetration enhancers can be classified as belonging to one of five broad categories, i.e., fatty acids, bile salts, chelating agents, surfactants and non-surfactants (Lee et al., *Critical Reviews in Therapeutic Drug Carrier Systems*, 1991, 8, 91-192; Muranishi, *Critical Reviews in Therapeutic Drug Carrier Systems*, 1990, 7:1).

Fatty Acids: Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a.k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7, 1; El-Hariri et al., *J. Pharm. Pharmacol.*, 1992, 44, 651).

Bile Salts: The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., Eds., McGraw-Hill, New York, N.Y., 1996, pages 934-935). Various natural bile salts, and their synthetic derivatives, act as penetration enhancers. Thus, bile salts include any of the naturally occurring components of bile as well as any of their synthetic derivatives.

Chelating Agents: Chelating agents have the added advantage of also serving as DNase inhibitors and include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., *Critical Reviews in Therapeutic Drug Carrier Systems*, 1991, page 92; Muranishi, *Critical Reviews in Therapeutic Drug Carrier Systems*, 1990, 7, 1. Buur et al., *J Control Rel.*, 1990, 14, 43).

Surfactants: Surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorochemical emulsions, such as FC-43 (Takahashi et al., *J. Pharm. Phamacol.*, 1988, 40, 252).

Non-Surfactants: Non-surfactants include, for example, unsaturated cyclic ureas, 1-alkyl- and 1-alkenylazacyclo-alkanone derivatives (Lee et al., *Critical Reviews in Therapeutic Drug Carrier Systems*, 1991, page 92); and non-steroidal anti-inflammatory agents such as diclofenac sodium, indomethacin and phenylbutazone (Yamashita et al., *J. Pharm. Pharmacol.*, 1987, 39, 621).

Carrier Compounds: As used herein, "carrier compound" refers to a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioated oligonucleotide in hepatic tissue is reduced when it is coadministered with polyinosinic acid, dextran sulfate, polycytidic acid or 4-acetamido-4'-isothiocyano-stilbene-2,2'-disulfonic acid (Miyao et al., *Antisense Res. Dev.*, 1995, 5, 115; Takakura et al., *Antisense & Nucl. Acid Drug Dev.*, 1996, 6, 177).

Pharmaceutically Acceptable Carriers: In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier can be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.). Sustained release oral delivery systems and/or enteric coatings for orally administered dosage forms are described in U.S. Pat. Nos. 4,704,295; 4,556,552; 4,309,406; and 4,309,404.

Miscellaneous Additional Components: The compositions of the present invention can additionally contain other adjunct components conventionally found in pharmaceutical compositions, at their art-established usage levels. Thus, for example, the compositions can contain additional compatible pharmaceutically-active materials such as, e.g., antipruritics, astringents, local anesthetics or anti-inflammatory agents, or can contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the invention.

Colloidal Dispersion Systems: Regardless of the method by which the oligonucleotides of the invention are introduced into a patient, colloidal dispersion systems can be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles and liposomes. A preferred colloidal dispersion system is a plurality of liposomes, artificial membrane vesicles which can be used as cellular delivery vehicles for bioactive agents in vitro and in vivo (Mannino et al., Biotechniques, 1988, 6, 682; Blume and Cevc, *Biochem. et Biophys. Acta*, 1990, 1029, 91; Lappalainen et al., *Antiviral Res.*, 1994, 23, 119; Chonn and Cullis, *Current Op. Biotech.*, 1995, 6, 698). It has been shown that large unilamellar vesicles (LUV), which range in size from 0.2-0.4 µm, can encapsulate a substantial percentage of an aqueous buffer containing large macromolecules. RNA, DNA and intact virions can be encapsulated within the aqueous interior and delivered to brain cells in a biologically active form (Fraley et al., *Trends Biochem. Sci.*, 1981, 6, 77). The composition of the liposome is usually a combination of lipids, particularly phospholipids, in particular, high phase transition temperature phospholipids, usually in combination with one or more steroids, particularly cholesterol. Examples of lipids useful in liposome production include phosphatidyl compounds, such as phosphatidylglycerol, phosphatidylcholine, phosphatidylserine, sphingolipids, phosphatidylethanolamine, cerebrosides and gangliosides. Particularly useful are diacyl phosphatidylglycerols, where the lipid moiety contains from 14-18 carbon atoms, particularly from 16-18 carbon atoms, and is saturated (lacking double bonds within the 14-18 carbon atom chain). Illustrative phospholipids include phosphatidylcholine, dipalmitoylphosphatidylcholine and distearoylphosphatidylcholine.

The targeting of colloidal dispersion systems, including liposomes, can be either passive or active. Passive targeting utilizes the natural tendency of liposomes to distribute to cells of the reticuloendothelial system in organs that contain sinusoidal capillaries. Active targeting, by contrast, involves modification of the liposome by coupling thereto a specific ligand such as a viral protein coat (Morishita et al., *Proc. Natl. Acad. Sci. (U.S.A.)*, 1993, 90, 8474), monoclonal antibody (or a suitable binding portion thereof), sugar, glycolipid or protein (or a suitable oligopeptide fragment thereof), or by changing the composition and/or size of the liposome in order to achieve distribution to organs and cell types other than the naturally occurring sites of localization. The surface of the targeted colloidal dispersion system can be modified in a variety of ways. In the case of a liposomal targeted delivery system, lipid groups can be incorporated into the lipid bilayer of the liposome in order to maintain the targeting ligand in close association with the lipid bilayer. Various linking groups can be used for joining the lipid chains to the targeting ligand. The targeting ligand, which binds a specific cell surface molecule found predominantly on cells to which delivery of the oligonucleotides of the invention is desired, can be, for example, (1) a hormone, growth factor or a suitable oligopeptide fragment thereof which is bound by a specific cellular receptor predominantly expressed by cells to which delivery is desired or (2) a polyclonal or monoclonal antibody, or a suitable fragment thereof (e.g., Fab; F(ab')$_2$) which specifically binds an antigenic epitope found predominantly on targeted cells. Two or more bioactive agents (e.g., an oligonucleotide and a conventional drug; two oligonucleotides) can be combined within, and delivered by, a single liposome. It is also possible to add agents to colloidal dispersion systems which enhance the intercellular stability and/or targeting of the contents thereof.

Means of Administration: The present invention provides compositions comprising oligonucleotides intended for administration to an animal.

Parenteral Delivery The administration of an oligonucleotide of the invention to an animal in a manner other than through the digestive canal. Means of preparing and administering parenteral pharmaceutical compositions are known in the art (see, e.g., Avis, Chapter 84 *In: Remington's Pharmaceutical Sciences,* 18th Ed., Gennaro, ed., Mack Publishing Co., Easton, Pa., 1990, pages 1545-1569). Parenteral means of delivery include, but are not limited to, the following illustrative examples.

Intravitreal injection, for the direct delivery of drug to the vitreous humor of a mammalian eye, is described in U.S. Pat. No. 5,591,720, the contents of which are hereby incorporated by reference. Means of preparing and administering ophthalmic preparations are known in the art (see, e.g., Mullins et al., Chapter 86 *In: Remington's Pharmaceutical Sciences,* 18th Ed., Gennaro, ed., Mack Publishing Co., Easton, Pa., 1990, pages 1581-1595).

Intravenous administration of antisense oligonucleotides to various non-human mammals has been described by Iversen (Chapter 26 *In: Antisense Research and Applications,* Crooke et al., Eds., CBC Press, Boca Raton, Fla., 1993, pages 461-469). Systemic delivery of oligonucleotides to non-human mammals via intraperitoneal means has also been described (Dean et al., *Proc. Natl. Acad. Sci.* (*U.S.A.*), 1994, 91, 11766).

Intraluminal drug administration, for the direct delivery of drug to an isolated portion of a tubular organ or tissue (e.g., such as an artery, vein, ureter or urethra), can be desired for the treatment of patients with diseases or conditions afflicting the lumen of such organs or tissues. To effect this mode of oligonucleotide administration, a catheter or cannula is surgically introduced by appropriate means. For example, for treatment of the left common carotid artery, a cannula is inserted thereinto via the external carotid artery. After isolation of a portion of the tubular organ or tissue for which treatment is sought, a composition comprising the oligonucleotides of the invention is infused through the cannula or catheter into the isolated segment. After incubation for from about 1 to about 120 minutes, during which the oligonucleotide is taken up by cells of the interior lumen of the vessel, the infusion cannula or catheter is removed and flow within the tubular organ or tissue is restored by removal of the ligatures which effected the isolation of a segment thereof (Morishita et al., *Proc. Natl. Acad. Sci. U.S.A.,* 1993, 90, 8474). Antisense oligonucleotides can also be combined with a biocompatible matrix, such as a hydrogel material, and applied directly to vascular tissue in vivo (Rosenberg et al., U.S. Pat. No. 5,593,974, issued Jan. 14, 1997).

Intraventricular drug administration, for the direct delivery of drug to the brain of a patient, can be desired for the treatment of patients with diseases or conditions afflicting the brain. To effect this mode of oligonucleotide administration, a silicon catheter is surgically introduced into a ventricle of the brain of a human patient, and is connected to a subcutaneous infusion pump (Medtronic Inc., Minneapolis, Minn.) that has been surgically implanted in the abdominal region (Zimm et al., *Cancer Research,* 1984, 44, 1698; Shaw, *Cancer,* 1993, 72(11 *Suppl.*), 3416). The pump is used to inject the oligonucleotides and allows precise dosage adjustments and variation in dosage schedules with the aid of an external programming device. The reservoir capacity of the pump is 18-20 mL and infusion rates can range from 0.1 mL/h to 1 mL/h. Depending on the frequency of administration, ranging from daily to monthly, and the dose of drug to be administered, ranging from 0.01 µg to 100 g per kg of body weight, the pump reservoir can be refilled at 3-10 week intervals. Refilling of the pump is accomplished by percutaneous puncture of the self-sealing septum of the pump.

Intrathecal drug administration, for the introduction of a drug into the spinal column of a patient can be desired for the treatment of patients with diseases of the central nervous system. To effect this route of oligonucleotide administration, a silicon catheter is surgically implanted into the L3-4 lumbar spinal interspace of a human patient, and is connected to a subcutaneous infusion pump which has been surgically implanted in the upper abdominal region (Luer and Hatton, *The Annals of Pharmacotherapy,* 1993, 27, 912; Ettinger et al., *Cancer,* 1978, 41, 1270; Yaida et al., *Regul. Pept.,* 1995, 59, 193). The pump is used to inject the oligonucleotides and allows precise dosage adjustments and variations in dose schedules with the aid of an external programming device. The reservoir capacity of the pump is 18-20 mL, and infusion rates can vary from 0.1 mL/h to 1 mL/h. Depending on the frequency of drug administration, ranging from daily to monthly, and dosage of drug to be administered, ranging from 0.01 µg to 100 g per kg of body weight, the pump reservoir can be refilled at 3-10 week intervals. Refilling of the pump is accomplished by a single percutaneous puncture to the self-sealing septum of the pump. The distribution, stability and pharmacokinetics of oligonucleotides within the central nervous system can be followed according to known methods (Whitesell et al., *Proc. Natl. Acad. Sci.* (*USA*), 1993, 90, 4665).

To effect delivery of oligonucleotides to areas other than the brain or spinal column via this method, the silicon catheter is configured to connect the subcutaneous infusion pump to, e.g., the hepatic artery, for delivery to the liver (Kemeny et al., *Cancer,* 1993, 71, 1964). Infusion pumps can also be used to effect systemic delivery of oligonucleotides (Ewel et al., *Cancer Research,* 1992, 52, 3005; Rubenstein et al., *J. Surg. Oncol.,* 1996, 62, 194).

Epidermal and Transdermal Delivery, in which pharmaceutical compositions containing drugs are applied topically, can be used to administer drugs to be absorbed by the local dermis or for further penetration and absorption by underlying tissues, respectively. Means of preparing and administering medications topically are known in the art (see, e.g., Block, Chapter 87 *In: Remington's Pharmaceutical Sciences,* 18th Ed., Gennaro, ed., Mack Publishing Co., Easton, Pa., 1990, pages 1596-1609).

Vaginal Delivery provides local treatment and avoids first pass metabolism, degradation by digestive enzymes, and potential systemic side-effects. This mode of administration can be preferred for antisense oligonucleotides targeted to pathogenic organisms for which the vagina is the usual habitat, e.g., *Trichomonas vaginalis.* In another embodiment, antisense oligonucleotides to genes encoding sperm-specific antibodies can be delivered by this mode of administration in order to increase the probability of conception and subsequent pregnancy. Vaginal suppositories (Block, Chapter 87 *In: Remington's Pharmaceutical Sciences,* 18th Ed., Gennaro, ed., Mack Publishing Co., Easton, Pa., 1990, pages 1609-1614) or topical ointments can be used to effect this mode of delivery.

Intravesical Delivery provides local treatment and avoids first pass metabolism, degradation by digestive enzymes, and potential systemic side-effects. However, the method requires urethral catheterization of the patient and a skilled staff. Nevertheless, this mode of administration can be preferred for antisense oligonucleotides targeted to pathogenic organisms, such as *T. vaginalis,* which can invade the urogenital tract.

Alimentary Delivery: The administration, directly or otherwise, to a portion of the alimentary canal of an animal. The term "alimentary canal" refers to the tubular passage in an animal that functions in the digestion and absorption of food and the elimination of food residue, which runs from the mouth to the anus, and any and all of its portions or segments, e.g., the oral cavity, the esophagus, the stomach, the small and large intestines and the colon, as well as compound portions thereof such as, e.g., the gastro-intestinal tract. Thus, the term "alimentary delivery" encompasses several routes of administration including, but not limited to, oral, rectal, endoscopic and sublingual/buccal administration. A common requirement for these modes of administration is absorption over some portion or all of the alimentary tract and a need for efficient mucosal penetration of the nucleic acid(s) so administered.

Buccal/Sublingual Administration: Delivery of a drug via the oral mucosa has several desirable features, including, in many instances, a more rapid rise in plasma concentration of the drug than via oral delivery (Harvey, Chapter 35 *In: Remington's Pharmaceutical Sciences*, 18th Ed., Gennaro, ed., Mack Publishing Co., Easton, Pa., 1990, page 711). Furthermore, because venous drainage from the mouth is to the superior vena cava, this route also bypasses rapid first-pass metabolism by the liver. Both of these features contribute to the sublingual route being the mode of choice for nitroglycerin (Benet et al., Chapter 1 *In: Goodman & Gilman's The Pharmacological Basis of Therapeutics*, 9th Ed., Hardman et al., Eds., McGraw-Hill, New York, N.Y., 1996, page 7).

Endoscopic Administration: Endoscopy can be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho*, 1992, 19(10 Suppl.), 1591). However, the procedure is unpleasant for the patient, and requires a highly skilled staff.

Rectal Administration: Drugs administered by the oral route can often be alternatively administered by the lower enteral route, i.e., through the anal portal into the rectum or lower intestine. Rectal suppositories, retention enemas or rectal catheters can be used for this purpose and can be preferred when patient compliance might otherwise be difficult to achieve (e.g., in pediatric and geriatric applications, or when the patient is vomiting or unconscious). Rectal administration can result in more prompt and higher blood levels than the oral route, but the converse can be true as well (Harvey, Chapter 35 *In: Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 *In: Goodman & Gilman's The Pharmacological Basis of Therapeutics*, 9th Ed., Hardman et al., Eds., McGraw-Hill, New York, N.Y., 1996).

Oral Administration: The preferred method of administration is oral delivery, which is typically the most convenient route for access to the systemic circulation. Absorption from the alimentary canal is governed by factors that are generally applicable, e.g., surface area for absorption, blood flow to the site of absorption, the physical state of the drug and its concentration at the site of absorption (Benet et al., Chapter 1 *In: Goodman & Gilman's The Pharmacological Basis of Therapeutics*, 9th Ed., Hardman et al., Eds., McGraw-Hill, New York, N.Y., 1996, pages 5-7). A significant factor which can limit the oral bioavailability of a drug is the degree of "first pass effects." For example, some substances have such a rapid hepatic uptake that only a fraction of the material absorbed enters the peripheral blood (Van Berge-Henegouwen et al., *Gastroenterology*, 1977, 73, 300). The compositions and methods of the invention circumvent, at least partially, such first pass effects by providing improved uptake of nucleic acids and thereby, e.g., causing the hepatic uptake system to become saturated and allowing a significant portion of the nucleic acid so administered to reach the peripheral circulation. Additionally or alternatively, the hepatic uptake system is saturated with one or more inactive carrier compounds prior to administration of the active nucleic acid.

The following examples illustrate the invention and are not intended to limit the same. Those skilled in the art will recognize, or be able to ascertain through routine experimentation, numerous equivalents to the specific substances and procedures described herein. Such equivalents are considered to be within the scope of the present invention.

EXAMPLES

Example 1

Synthesis of Oligonucleotides

General Synthetic Techniques: Oligonucleotides were synthesized on an automated DNA synthesizer using standard phosphoramidite chemistry with oxidation using iodine. β-Cyanoethyldiisopropyl phosphoramidites were purchased from Applied Biosystems (Foster City, Calif.). For phosphorothioate oligonucleotides, the standard oxidation bottle was replaced by a 0.2 M solution of 3H-1,2-benzodithiole-3-one-1,1-dioxide in acetonitrile for the stepwise thiation of the phosphite linkages.

The synthesis of 2'-O-methyl- (a.k.a. 2'-methoxy-) phosphorothioate oligonucleotides is according to the procedures set forth above substituting 2'-O-methyl β-cyanoethyldiisopropyl phosphoramidites (Chemgenes, Needham, Mass.) for standard phosphoramidites and increasing the wait cycle after the pulse delivery of tetrazole and base to 360 seconds.

Similarly, 2'-O-propyl- (a.k.a 2'-propoxy-) phosphorothioate oligonucleotides are prepared by slight modifications of this procedure and essentially according to procedures disclosed in U.S. patent application Ser. No. 08/383,666, filed Feb. 3, 1995, which is assigned to the same assignee as the instant application.

The 2'-fluoro-phosphorothioate oligonucleotides of the invention are synthesized using 5'-dimethoxytrityl-3'-phosphoramidites and prepared as disclosed in U.S. patent application Ser. No. 08/383,666, filed Feb. 3, 1995, and U.S. Pat. No. 5,459,255, which issued Oct. 8, 1996, both of which are assigned to the same assignee as the instant application. The 2'-fluoro-oligonucleotides were prepared using phosphoramidite chemistry and a slight modification of the standard DNA synthesis protocol (i.e., deprotection was effected using methanolic ammonia at room temperature).

The 2'-methoxyethoxy oligonucleotides were synthesized essentially according to the methods of Martin et al. (*Helv. Chim. Acta*, 1995, 78, 486). For ease of synthesis, the 3' nucleotide of the 2'-methoxyethoxy oligonucleotides was a deoxynucleotide, and 2'-O—$CH_2CH_2OCH_3$-cytosines were 5-methyl cytosines, which were synthesized according to the procedures described below.

PNA antisense analogs are prepared essentially as described in U.S. Pat. Nos. 5,539,082 and 5,539,083, both of which (1) issued Jul. 23, 1996, and (2) are assigned to the same assignee as the instant application.

Purification: After cleavage from the controlled pore glass column (Applied Biosystems) and deblocking in concentrated ammonium hydroxide at 55?C for 18 hours, the oligonucleotides were purified by precipitation twice out of 0.5 M NaCl with 2.5 volumes ethanol. Analytical gel electrophoresis was accomplished in 20% acrylamide, 8 M urea, 45 mM Tris-borate buffer, pH 7.0. Oligodeoxynucleotides and their phosphorothioate analogs were judged from electrophoresis to be greater than 80% full length material.

Example 2

Assays for Oligonucleotide-Mediated Inhibition of JNK mRNA Expression in Human Tumor Cells In order to evaluate the activity of potential JNK-modulating oligonucleotides, human lung carcinoma cell line A549 (American Type Culture Collection, Rockville, Md. No. ATCC CCL-185) cells or other cell lines as indicated in the Examples, were grown and treated with oligonucleotides or control solutions as detailed below.

After harvesting, cellular extracts were prepared and examined for specific JNK in RNA levels or JNK protein levels (i.e., Northern or Western assays, respectively). In all cases, "% expression" refers to the amount of JNK-specific signal in an oligonucleotide-treated cell relative to an untreated cell (or a cell treated with a control solution that lacks oligonucleotide).

Northern Assays: The mRNA expression of each JNK protein was determined by using a nucleic acid probe specifically hybridizable thereto. Nucleic acid probes specific for JNK1, JNK2 and JNK3 are described in Examples 3, 4 and 5, respectively. The probes were radiolabelled by means well known in the art (see, e.g., *Short Protocols in Molecular Biology*, 2nd Ed., Ausubel et al., Eds., John Wiley & Sons, New York, 1992, pages 3-11 to 2-3-44 and 4-17 to 4-18; Ruth, Chapter 6 *In: Methods in Molecular Biology*, Vol. 26: *Protocols for Oligonucleotide Conjugates*, Agrawal, ed., Humana Press Inc., Totowa, N.J., 1994, pages 167-185; and Chapter 10 *In: Molecular Cloning: A Laboratory Manual*, 2nd Ed., Sambrook et al., Eds., pages 10.1-10.70). The blots were stripped and reprobed with a $^{32}$P-labeled glyceraldehyde 3-phosphate dehydrogenase (G3PDH) probe (Clontech Laboratories, Inc., Palo Alto, Calif.) in order to confirm equal loading of RNA and to allow the levels of JNK transcripts to be normalized with regard to the G3PDH signals.

A549 cells were grown in T-75 flasks until 80-90% confluent. At this time, the cells were washed twice with 10 mL of media (DMEM), followed by the addition of 5 mL of DMEM containing 20 µg/mL of LIPOFECTIN™ (i.e., 1:1 (w/w) DOTMA/DOPE, Life Technologies, Gaithersburg, Md.; DOTMA=N-[1-(2,3-dioleyoxy)propyl]-N,N,N-trimethylammonium chloride; DOPE=dioleoyl phosphatidylethanolamine). The oligonucleotides were added from a 10 mM stock solution to a final concentration of 400 nM, and the two solutions were mixed by swirling the flasks. As a control, cells were treated with LIPOFECTIN™ without oligonucleotide under the same conditions and for the same times as the oligonucleotide-treated samples. After 4 hours at 37° C., the medium was replaced with fresh DMEM containing 10% serum. The cells were allowed to recover for 18 hours. Total cellular RNA was then extracted in guanidinium, subject to gel electrophoresis and transferred to a filter according to techniques known in the art (see, e.g., Chapter 7 *In: Molecular Cloning: A Laboratory Manual*, 2nd Ed., Sambrook et al., Eds., pages 7.1-7.87, and *Short Protocols in Molecular Biology*, 2nd Ed., Ausubel et al., Eds., John Wiley & Sons, New York, 1992, pages 2-24 to 2-30 and 4-14 to 4-29). Filters were typically hybridized overnight to a probe specific for the particular JNK gene of interest in hybridization buffer (25 mM KPO$_4$, pH 7.4; 5×SSC; 5×Denhardt's solution, 100 µg/ml Salmon sperm DNA and 50% formamide) (Alahari et al, *Nucl. Acids Res.*, 1993, 21, 4079). This was followed by two washes with 1×SSC, 0.1% SDS and two washes with 0.25×SSC, 0.1% SDS. Hybridizing bands were visualized by exposure to X-OMAT AR film and quantitated using a PHOSPHORIMAGER™ essentially according to the manufacturer's instructions (Molecular Dynamics, Sunnyvale, Calif.).

Western Assays: A549 cells were grown and treated with oligonucleotides as described above. Cells were lysed, and protein extracts were electrophoresed (SDS-PAGE) and transferred to nitrocellulose filters by means known in the art (see, e.g., Chapter 18 *In: Molecular Cloning. A Laboratory Manual*, 2nd Ed., Sambrook et al., Eds., pages 18.34, 18.47-18.54 and 18.60-18.75)). The amount of each JNK protein was determined by using a primary antibody that specifically recognizes the appropriate JNK protein. The primary antibodies specific for each JNK protein are described in the appropriate Examples. The primary antibodies were detected by means well known in the art (see, e.g., *Short Protocols in Molecular Biology*, 2nd Ed., Ausubel et al., Eds., John Wiley & Sons, New York, 1992, pages 10-33 to 10-35; and Chapter 18 *In: Molecular Cloning: A Laboratory Manual*, 2nd Ed., Sambrook et al., Eds., pages 18.1-18.75 and 18.86-18.88) and quantitated using a PHOSPHORIMAGER™ essentially according to the manufacturer's instructions (Molecular Dynamics, Sunnyvale, Calif.).

Levels of JNK proteins can also be quantitated by measuring the level of their corresponding kinase activity. Such kinase assays can be done in gels in situ (Hibi et al., *Genes & Dev.*, 1993, 7, 2135) or after immunoprecipitation from cellular extracts (Derijard et al., *Cell*, 1994, 76, 1025). Substrates and/or kits for such assays are commercially available from, for example, Upstate Biotechnology, Inc. (Lake Placid, N.Y.), New England Biolabs, Inc., (Beverly, Mass.) and Calbiochem-Novabiochem Biosciences, Inc., (La Jolla, Calif.).

Example 3

Oligonucleotide-Mediated Inhibition of JNK1 Expression

JNK1 oligonucleotide sequences: Table 1 lists the nucleotide sequences of a set of oligonucleotides designed to specifically hybridize to JNK1 mRNAs and their corresponding ISIS and SEQ ID numbers. The nucleotide co-ordinates of the target gene, JNK1, and gene target regions are also included. The nucleotide co-ordinates are derived from GenBank accession No. L26318 (SEQ ID NO: 87), locus name "HUMJNK1" (see also FIG. 1(A) of Derijard et al., *Cell*, 1994, 76, 1025). The abbreviations for gene target regions are as follows: 5'-UTR, 5' untranslated region; tIR, translation initiation region; ORF, open reading frame; 3'-UTR, 3' untranslated region. The nucleotides of the oligonucleotides whose sequences are presented in Table 1 are connected by phosphorothioate linkages and are unmodified at the 2' position (i.e., 2'-deoxy). It should be noted that the oligonucleotide target co-ordinate positions and gene target regions can vary within mRNAs encoding related isoforms of JNK1 (see subsection G, below).

In addition to hybridizing to human JNK1 mRNAs, the full oligonucleotide sequences of ISIS Nos. 12548 (SEQ ID NO: 17) and 12551 (SEQ ID NO: 20) hybridize to the 5' ends of mRNAs from *Rattus norvegicus* that encode a stress-activated protein kinase named "p54?" (Kyriakis et al., Nature, 1994, 369, 156). Specifically, ISIS 12548 (SEQ ID NO: 17) hybridizes to bases 498-517 of GenBank accession No. L27129 (SEQ ID NO: 88), locus name "RATSAPKD," and ISIS 12551 (SEQ ID NO: 20) hybridizes to bases 803-822 of the same sequence.

JNK1-specific probes: In initial screenings of a set of oligonucleotides derived from the JNK1 sequence (Table 2) for biological activity, a cDNA clone of JNK1 (Derijard et al., *Cell*, 1994, 76, 1025) was radiolabeled and used as a JNK1-specific probe in Northern blots. Alternatively, however, one or more of the oligonucleotides of Table 1 is detectably labeled and used as a JNK1-specific probe.

TABLE 1

Nucleotide Sequences of JNK1 Oligonucleotides

| ISIS NO. | NUCLEOTIDE SEQUENCE (5'→3') | SEQ ID NO: | TARGET GENE NUCLEOTIDE CO-ORDINATES | GENE TARGET REGION |
|---|---|---|---|---|
| 11978 | ATT-CTT-TCC-ACT-CTT-CTA-TT | 1 | 1062-1081 | ORF |
| 11979 | CTC-CTC-CAA-GTC-CAT-AAC-TT | 2 | 1094-1113 | ORF |
| 11980 | CCC-GTA-TAA-CTC-CAT-TCT-TG | 3 | 1119-1138 | ORF |
| 11981 | CTG-TGC-TAA-AGG-AGA-GGG-CT | 4 | 1142-1161 | ORF |
| 11982 | ATG-ATG-GAT-GCT-GAG-AGC-CA | 5 | 1178-1197 | 3'-UTR |
| 11983 | GTT-GAC-ATT-GAA-GAC-ACA-TC | 6 | 1215-1234 | 3'-UTR |
| 11984 | CTG-TAT-CAG-AGG-CCA-AAG-TC | 7 | 1241-1260 | 3'-UTR |
| 11985 | TGC-TGC-TTC-TAG-ACT-GCT-GT | 8 | 1261-1280 | 3'-UTR |
| 11986 | AGT-CAT-CTA-CAG-CAG-CCC-AG | 9 | 1290-1309 | 3'-UTR |
| 11987 | CCA-TCC-CTC-CCA-CCC-CCC-GA | 10 | 1320-1339 | 3'-UTR |
| 11988 | ATC-AAT-GAC-TAA-CCG-ACT-CC | 11 | 1340-1359 | 3'-UTR |
| 11989 | CAA-AAA-TAA-GAC-CAC-TGA-AT | 12 | 1378-1397 | 3'-UTR |
| 12463 | CAC-GCT-TGC-TTC-TGC-TCA-TG | 13 | 0018-0037 | tIR |
| 12464 | CGG-CTT-AGC-TTC-TTG-ATT-GC | 14 | 0175-0194 | ORF |
| 12538 | CCC-GCT-TGG-CAT-GAG-TCT-GA | 15 | 0207-0226 | ORF |
| 12539 | CTC-TCT-GTA-GGC-CCG-CTT-GG | 16 | 0218-0237 | ORF |
| 12548 | ATT-TGC-ATC-CAT-GAG-CTC-CA | 17 | 0341-0360 | ORF |
| 12549 | CGT-TCC-TGC-AGT-CCT-GGC-CA | 18 | 0533-0552 | ORF |
| 12550 | GGA-TGA-CCT-CGG-GTG-CTC-TG | 19 | 0591-0610 | ORF |
| 12551 | CCC-ATA-ATG-CAC-CCC-ACA-GA | 20 | 0646-0665 | ORF |
| 12552 | CGG-GTG-TTG-GAG-AGC-TTC-AT | 21 | 0956-0975 | ORF |
| 12553 | TTT-GGT-GGT-GGA-GCT-TCT-GC | 22 | 1006-1025 | ORF |
| 12554 | GGC-TGC-CCC-CGT-ATA-ACT-CC | 23 | 1126-1145 | ORF |
| 12555 | TGC-TAA-AGG-AGA-GGG-CTG-CC | 24 | 1139-1158 | ORF |
| 12556 | AGG-CCA-AAG-TCG-GAT-CTG-TT | 25 | 1232-1251 | 3'-UTR |
| 12557 | CCA-CCC-CCC-GAT-GGC-CCA-AG | 26 | 1311-1330 | 3'-UTR |

Activities of JNK1 oligonucleotides: The data from screening a set of JNK1-specific phosphorothioate oligonucleotides (Table 2) indicate the following results. Oligonucleotides showing activity in this assay, as reflected by levels of inhibition of JNK1 mRNA levels of at least 50%, include ISIS Nos. 11982, 11983, 11985, 11987, 12463, 12464, 12538, 12539, 12548, 12549, 12550, 12552, 12553, 12554, 12555, 12556 and 12557 (SEQ ID NOS: 5, 6, 8, 10, 13, 14, 15, 16, 17, 18, 19, 21, 22, 23, 24, 25 and 26, respectively). These oligonucleotides are thus preferred embodiments of the invention for modulating JNK1 expression. Oligonucleotides showing levels of inhibition of JNK1 mRNAs of at least 80% in this assay, include ISIS Nos. 11982, 12539, 12464, 12548, 12554 and 12464 (SEQ ID NOS: 5, 14, 16, 17 and 23, respectively). These oligonucleotides are thus more preferred embodiments of the invention for modulating JNK1 expression.

The time course of inhibition of JNK1 in RNA expression by ISIS 12539 (SEQ ID NO: 16) is shown in Table 3. Following the 4 hour treatment with ISIS 12539, the level of inhibition of JNK1 was greater than about 85% (t=0 h), rose to about 95% inhibition at t=4 h, and subsequently remained at greater than or equal to about 80% (t=12 and 48 h) or 60% (t=72 h).

TABLE 2

Activities of JNK1 Oligonucleotides

| ISIS No: | SEQ ID NO: | GENE TARGET REGION | % EXPRESSION: | % INHIBITION: |
|---|---|---|---|---|
| 11978 | 1 | ORF | 85% | 15% |
| 11979 | 2 | ORF | 90% | 10% |
| 11980 | 3 | ORF | 85% | 15% |
| 11981 | 4 | ORF | 62% | 28% |
| 11982 | 5 | 3'-UTR | 13% | 87% |
| 11983 | 6 | 3'-UTR | 40% | 60% |
| 11984 | 7 | 3'-UTR | 53% | 47% |
| 11985 | 8 | 3'-UTR | 47% | 53% |
| 11986 | 9 | 3'-UTR | 90% | 10% |
| 11987 | 10 | 3'-UTR | 47% | 53% |
| 11988 | 11 | 3'-UTR | 78% | 22% |
| 11989 | 12 | 3'-UTR | 60% | 40% |
| 12463 | 13 | tIR | 23% | 77% |
| 12464 | 14 | ORF | 18% | 82% |
| 12538 | 15 | ORF | 33% | 67% |
| 12539 | 16 | ORF | 9% | 91% |
| 12548 | 17 | ORF | 5% | 95% |
| 12549 | 18 | ORF | 28% | 72% |
| 12550 | 19 | ORF | 40% | 60% |
| 12551 | 20 | ORF | 52% | 48% |
| 12552 | 21 | ORF | 34% | 66% |
| 12553 | 22 | ORF | 25% | 75% |
| 12554 | 23 | ORF | 11% | 89% |
| 12555 | 24 | ORF | 27% | 73% |
| 12556 | 25 | 3'-UTR | 41% | 59% |
| 12557 | 26 | 3'-UTR | 29% | 71% |

TABLE 3

Time Course of Response to JNK1 Antisense Oligonucleotides (ASOs)

| ISIS # | SEQ ID NO: | ASO Description | Time | Normalized % Control | % Inhibition |
|---|---|---|---|---|---|
| control | — | (LIPOFECTIN ™ only) | 0 h | 100.0 | 0.0 |
| control | — | (LIPOFECTIN ™ only) | 4 h | 100.0 | 0.0 |
| control | — | (LIPOFECTIN ™ only) | 12 h | 100.0 | 0.0 |
| control | — | (LIPOFECTIN ™ only) | 48 h | 100.0 | 0.0 |
| control | — | (LIPOFECTIN ™ only) | 72 h | 100.0 | 0.0 |
| 12539 | 16 | JNK1 active | 0 h | 14.1 | 85.9 |
| 12539 | 16 | " | 4 h | 5.9 | 94.1 |
| 12539 | 16 | " | 12 h | 11.6 | 88.4 |
| 12539 | 16 | " | 48 h | 21.0 | 79.0 |
| 12539 | 16 | " | 272 h | 41.5 | 58.5 |

Additional JNK1 oligonucleotides: The results for JNK1-specific oligonucleotides (Table 2) indicate that one of the most active phosphorothioate oligonucleotides for modulating JNK1 expression is ISIS 12539 (SEQ ID NO: 16). As detailed in Table 4, additional oligonucleotides based on this oligonucleotide were designed to confirm and extend the findings described above.

Oligonucleotides ISIS Nos. 14320 (SEQ ID NO: 27) and 14321 (SEQ ID NO: 28) are 2'-deoxy-phosphorothioate sense strand and scrambled controls for ISIS 12539 (SEQ ID NO: 16), respectively. ISIS Nos. 15346 and 15347 are "gapmers" corresponding to ISIS 12539; both have 2'-methoxyethoxy "wings" (having phosphorothioate linkages in the case of ISIS 15346 and phosphodiester linkages in the case of ISIS 15347) and a central 2'-deoxy "gap" designed to support RNaseH activity on the target mRNA molecule. Similarly, ISIS Nos. 15348 to 15350 are "wingmers" corresponding to ISIS 12539 and have a 5' or 3'2'-methoxyethoxy RNaseH-refractory "wing" and a 3' or 5' (respectively) 2'-deoxy "wing" designed to support RNaseH activity on the target JNK1 mRNA.

The chemically modified derivatives of ISIS 12539 (SEQ ID NO: 16) were tested in the Northern assay described herein at concentrations of 100 and 400 nM, and the data (Table 5) indicate the following results. At 400 nM, relative to the 2'-unmodified oligonucleotide ISIS 12539, both "gapmers" (ISIS Nos. 15346 and 15347) effected inhibition of JNK1 mRNA expression up to at least about 88% inhibition. Similarly, the four "wingmers" (ISIS Nos. 15348 to 15351) effected inhibition of JNK1 expression of up to at least about 60 to 70% inhibition.

TABLE 4

Chemically Modified JNK1 Oligonucleotides

| ISIS NO. | NUCLEOTIDE SEQUENCE (5'→3') AND CHEMICAL MODIFICATIONS* | SEQID NO: | COMMENTS |
|---|---|---|---|
| 112539 | $C^S T^S C^S T^S C^S T^S G^S T^S A^S G^S G^S C^S C^S C^S G^S C^S T^S T^S G^S G$ | 16 | active |
| 14320 | $C^S C^S A^S A^S G^S C^S G^S G^S G^S C^S C^S T^S A^S C^S A^S G^S A^S G$ | 27 | 12539 sense control |
| 14321 | $C^S T^S T^S T^S C^S C^S G^S T^S T^S G^S G^S A^S C^S C^S C^S T^S G^S G$ | 28 | scrambled control |

TABLE 4-continued

Chemically Modified JNK1 Oligonucleotides

| ISIS NO. | NUCLEOTIDE SEQUENCE (5'→3') AND CHEMICAL MODIFICATIONS* | SEQ ID NO: | COMMENTS |
|---|---|---|---|
| 15345 | $C^S T^S C^S T^S C^S T^S G^S T^S A^S G^S G^S C^S C^S C^S G^S C^S T^S T^S G^S G$ | 16 | fully 2'-methoxyethoxy |
| 15346 | $C^S T^S C^S T^S C^S T^S G^S T^S A^S G^S G^S C^S C^S C^S G^S C^S T^S T^S G^S G$ | 16 | "gapmer" |
| 15347 | $C^O T^O C^O T^O C^S T^S G^S T^S A^S G^S G^S C^S C^S C^S G^O C^O T^O T^O G^O G$ | 16 | "gapmer" |
| 15348 | $C^S T^S C^S T^S C^S T^S G^S T^S A^S G^S G^S C^S C^S C^S G^S C^S T^S T^S G^S G$ | 16 | "wingmer" |
| 15349 | $C^S T^S C^S T^S C^S T^S G^S T^S A^S G^S G^S C^S C^S C^S G^S C^S T^S T^S G^S G$ | 16 | "wingmer" |
| 15351 | $C^O T^O C^O T^O C^O T^O G^O T^O A^O G^O G^S C^S C^S C^S G^S C^S T^S T^S G^S G$ | 16 | "wingmer" |
| 15350 | $C^S T^S C^S T^S C^S T^S G^S T^S A^S G^O G^O C^O C^O C^O G^O C^O T^O T^O G^O G$ | 16 | "wingmer" |
| 20571 | $C^S T^S C^S T^S C^S T^S G^S T^S A^S G^S G^S \underline{C}^S \underline{C}^S \underline{C}^S G^S C^S T^S T^S G^S G$ | 1 | fully 5-methyl-cytosine version of ISIS 15346 |

*Emboldened residues, 2'-methoxyethoxy-residues (others are 2'-deoxy-) including "C" residues, 5-methyl-cytosines; "$^O$", phosphodiester linkage; "$^S$", phosphorothioate linkage.
---"<u>C</u>" residues, 2'-deoxy 5-methylcytosine residues;---

TABLE 5

Activity of Chemically Modified JNK1 Antisense Oligonucleotides

| ISIS # | SEQ ID NO: | OligonucleotideDescription* | Dose | Normalized % Control |
|---|---|---|---|---|
| control | — | No oligonucleotide (LIPOFECTIN ™ only) | — | 100.0 |
| 12539 | 16 | JNK1 active, fully P=S & | 100 nM | 56.4 |
| 12539 | 16 | fully 2'-deoxy | 400 nM | 26.7 |
| 15345 | 16 | fully P=S & fully 2'-MOE | 100 nM | 95.4 |
| 15345 | 16 |  | 400 nM | 89.1 |
| 15346 | 16 | gapmer: P=S, 2'-MOE wings; | 100 nM | 22.6 |
| 15346 | 16 | P=S, 2'-deoxy core | 400 nM | 11.0 |
| 15347 | 16 | gapmer: P=O, 2'-MOE wings; | 100 nM | 27.1 |
| 15347 | 16 | P=S, 2-deoxy core | 400 nM | 11.7 |
| 15348 | 16 | wingmer: fully P=S; | 100 nM | 30.4 |
| 15348 | 16 | 5' 2'-MOE; 3' 2-deoxy | 400 nM | 32.9 |
| 15349 | 16 | wingmer: fully P=S; | 100 nM | 42.5 |
| 15349 | 16 | 5' 2-deoxy; 3' 2'-MOE | 400 nM | 35.5 |
| 15351 | 16 | wingmer: 5' P=O & 2'-MOE; | 100 nM | 45.1 |
| 15351 | 16 | 3' P=S & 2-deoxy | 400 nM | 39.8 |
| 15350 | 16 | wingmer: 5' P=S & 2'- | 100 nM | 71.1 |
| 15350 | 16 | deoxy; 3' P=O & 2'-MOE | 400 nM | 41.3 |

*Abbreviations: P=O, phosphodiester linkage; P=S, hosphorothioate linkage; MOE, methoxyethoxy-.

Dose- and sequence-dependent response to JNK1 oligonucleotides: In order to demonstrate a dose-dependent response to ISIS 12539 (SEQ ID NO: 16), different concentrations (i.e., 50, 100, 200 and 400 nM) of ISIS 12539 were tested for their effect on JNK1 mRNA levels in A549 cells (Table 6). In addition, two control oligonucleotides (ISIS 14320, SEQ ID NO: 27, sense control, and ISIS 14321, SEQ ID NO: 28, scrambled control; see also Table 4) were also applied to A549 cells in order to demonstrate the specificity of ISIS 12539. The results (Table 6) demonstrate that the response of A549 cells to ISIS 12539 is dependent on dose in an approximately linear fashion. In contrast, neither of the control oligonucleotides effect any consistent response on JNK1 mRNA levels.

Western Assays: In order to assess the effect of oligonucleotides targeted to JNK1 mRNAs on JNK1 protein levels, Western assays were performed essentially as described above in Example 2, with the following exception(s) and/or modification(s). A primary antibody that specifically binds to JNK1 (catalog No. sc-474-G) was purchased from Santa Cruz Biotechnology, Inc. (Santa Cruz, Calif.; other JNK1-specific antibodies are available from StressGen Biotechnologies, Inc., Victoria, BC, Canada; and Research Diagnostics, Inc., Flanders, N.J.). In this experiment, cells were grown and treated with oligonucleotide at 300 nM for the initial 20 hours and then at 200 nM for 4 hours. At t=48 h, aliquots were removed for Northern and Western analyses, and fresh media was added to the cells. Aliquots for analysis were also taken at t=72 h. The samples from t=48 h and t=72 h were analyzed using the Northern and Western assays described above.

TABLE 6

Dose-Dependent Responses to JNK1 Antisense Oligonucleotides

| ISIS # | SEQ ID NO: | OligonucleotideDescription | Dose | Normalized % Control |
|---|---|---|---|---|
| control | — | No oligonucleotide (LIPOFECTIN ™ only) | — | 100.0 |
| 12539 | 16 | JNK1 active | 50 nM | 70.3 |
| 12539 | 16 | " | 100 nM | 51.6 |
| 12539 | 16 | " | 200 nM | 22.4 |
| 12539 | 16 | " | 400 nM | 11.1 |
| 14320 | 27 | 12539 sense control | 50 nM | 103.6 |
| 14320 | 27 | " | 100 nM | 76.3 |
| 14320 | 27 | " | 200 nM | 98.9 |
| 14320 | 27 | " | 400 nM | 97.1 |
| 14321 | 28 | 12539 scrambled control | 50 nM | 91.8 |
| 14321 | 28 | " | 100 nM | 94.1 |
| 14321 | 28 | " | 200 nM | 100.2 |
| 14321 | 28 | " | 400 nM | 79.2 |

The data (Table 7) indicate the following results. In this assay, at t=48 h, oligonucleotides showing a level of mRNA % inhibition from > about 70% to about 100% include ISIS Nos. 12539 (phosphorothioate linkages), 15346 and 15347 ("gapmers"), and 15348 and 15351 (5' "wingmers") (SEQ ID NO: 16). Oligonucleotides showing levels of mRNA inhibition of from ≧ about 90% to about 100% of JNK1 mRNAs in this assay include ISIS Nos. 12539, 15345 AND 15346 (SEQ ID NO: 16). The oligonucleotides tested showed approximately parallel levels of JNK1 protein inhibition; ISIS Nos. 12539, 15346-15348 and 15351 effected levels of protein inhibition ≧ about 40%, and ISIS Nos. 12539, 15346 and 15347 effected levels of protein inhibition ≧ about 55%.

At t=72 h, oligonucleotides showing a level of mRNA % inhibition from > about 70% to about 100% include ISIS Nos. 12539 (phosphorothioate linkages), 15346 and 15347 ("gapmers"), and 15348 (5'"wingmers") (SEQ ID NO: 16). Oligonucleotides showing levels of mRNA inhibition of from ≧ about 90% to about 100% of JNK1 mRNAs at this point in the assay include ISIS Nos. 12539 and 155346 (SEQ ID NO: 16). Overall, the oligonucleotides tested showed higher levels of JNK1 protein inhibition at this point in the assay. With the exception of the fully 2'-methoxyethoxy-modified ISIS 15345, all of the oligonucleotides in Table 7 effect ≧ about 40% protein inhibition. ISIS Nos. 12539, 15346-15348 and 15351 effected levels of protein inhibition ≧ about 60%, and ISIS Nos. 12539, 15346 and 15347 effected levels of protein inhibition ≧ about 70%.

TABLE 7

Modulation of JNK1 mRNA and JNK1 Protein Levels by Modified JNK1 Antisense Oligonucleotides

| ISIS # | SEQ ID NO: | RNA % Control | RNA % Inhibition | Protein % Control | Protein % Inhibition |
|---|---|---|---|---|---|
| t = 48 h | | | | | |
| control | — | 100.0 | 0.0 | 100.0 | 0.0 |
| 12539 | 16 | 6.7 | 93.3 | 44.3 | 55.7 |
| 15345 | 16 | 70.3 | 29.7 | 105.0 | (0.0) |
| 15346 | 16 | 4.3 | 95.7 | 42.7 | 57.3 |
| 15347 | 16 | 7.9 | 92.1 | 38.8 | 61.2 |
| 15348 | 16 | 24.3 | 75.7 | 58.3 | 41.7 |
| 15349 | 16 | 63.1 | 36.9 | 69.5 | 30.5 |
| 15350 | 16 | 49.2 | 50.8 | 71.7 | 28.3 |
| 15351 | 16 | 26.9 | 73.1 | 52.4 | 47.6 |
| t = 72 h | | | | | |
| control | 16 | 100.0 | 0.0 | 100.0 | 0.0 |
| 12539 | 16 | 11.7 | 88.3 | 29.2 | 70.8 |
| 15345 | 16 | 187.4 | (0.0) | 87.8 | 12.2 |
| 15346 | 16 | 10.6 | 89.4 | 25.7 | 74.3 |
| 15347 | 16 | 8.2 | 81.8 | 28.4 | 71.6 |
| 15348 | 16 | 28.0 | 72.0 | 41.7 | 58.3 |
| 15349 | 16 | 52.0 | 48.0 | 56.5 | 43.5 |
| 15350 | 16 | 54.4 | 45.6 | 58.4 | 41.6 |
| 15351 | 16 | 46.1 | 53.9 | 37.0 | 63.0 |

Oligonucleotides specific for JNK1 isoforms: Subsequent to the initial descriptions of JNK1 (Derijard et al., *Cell*, 1994, 76, 1025), cDNAs encoding related isoforms of JNK1 were cloned and their nucleotide sequences determined (Gupta et al., *EMBO Journal*, 1996, 15, 2760). In addition to JNK1-a1 (GenBank accession No. L26318 (SEQ ID NO: 87), locus name "HUMJNK1"), which encodes a polypeptide having an amino acid sequence identical to that of JNK1, the additional isoforms include JNK1-a2 (GenBank accession No. U34822 (SEQ ID NO: 89), locus name "U34822"), JNK1-β1 (GenBank accession No. U35004 (SEQ ID NO: 90), locus name "HSU35004") and JNK1-132 (GenBank accession No. U35005 (SEQ ID NO: 91), locus name "HSU35005"). The four isoforms of JNK1, which probably arise from alternative mRNA splicing, can each interact with different transcription factors or sets of transcription factors (Gupta et al., *EMBO Journal*, 1996, 15, 2760). As detailed below, the oligonucleotides of the invention are specific for certain members or sets of these isoforms of JNK1.

In the ORFs of mRNAs encoding JNK1/JNK1-a1 and JNK1-a2, nucleotides (nt) 631-665 of JNK1/JNK1-a1 (Genbank accession No. L26318 (SEQ ID NO: 87)) and nt 625-659 of JNK1-a2 (Genbank accession No. U34822 (SEQ ID NO: 89)) have the sequence shown below as SEQ ID NO: 63, whereas, in the ORFs of mRNAs encoding JNK1-β1 and JNK1-β2, nt 631-665 of JNK1-β3 (GenBank accession No. U35004 (SEQ ID NO: 90)) and nt 626-660 of JNK1-132 (GenBank accession No. U35005 (SEQ ID NO: 91)) have the sequence shown below as SEQ ID NO: 64. For purposes of illustration, SEQ ID NOS: 63 and 64 are shown aligned with each other (vertical marks, "|," indicate bases that are identical in both sequences):

```
5'-AACGTGGATTTATGGTCTGTGGGGTGCATTATGGG  SEQ ID
   ||||| ||  | |||||| ||  |||||||||| |||||  NO: 63
5'-AACGTTGACATTTGGTCAGTTGGGTGCATCATGGG  SEQ ID
                                          NO: 64
```

Due to this divergence between the a and b JNK1 isoforms, antisense oligonucleotides derived from the reverse complement of SEQ ID NO: 63 (i.e., SEQ ID NO: 65, see below) can be used to modulate the expression of JNK1/JNK1-a1 and JNK1-a2 without significantly effecting the expression of JNK1-β1 and JNK1-β2. In like fashion, antisense oligonucleotides derived from the reverse complement of SEQ ID NO: 64 (i.e., SEQ ID NO: 66, see below) can be selected and used to modulate the expression of JNK1-β1 and JNK1-β2 without significantly effecting the expression of JNK1/JNK1-a1 and JNK1-a2. As an example, an oligonucleotide having a sequence derived from SEQ ID NO: 65 but not to SEQ ID NO: 66 is specifically hybridizable to mRNAs encoding JNK1/JNK1-a1 and JNK1-a2 but not to those encoding JNK1-β1 and JNK1-β2:

```
5'-CCCATAATGCACCCCACAGACCATAAATCCACGTT  SEQ ID
   ||||| ||||||||| ||  |||| |  | || |||||  NO: 65
5'-CCCATGATGCACCCAACTGACCAAATGTCAACGTT  SEQ ID
                                          NO: 66
```

As a further example, in the ORFs of mRNAs encoding JNK1/JNK1-a1 and JNK1-a2, nt 668-711 of JNK1/JNK1-a1 (Genbank accession No. L26318 (SEQ ID NO: 87)) and nt 662-705 of JNK1-a2 (Genbank accession No. U34822 (SEQ ID NO: 89)) have the sequence shown below as SEQ ID NO: 67, whereas, in the ORFs of mRNAs encoding JNK-⊕1 and JNK1-β2, nt 668-711 of JNK1-β1 (GenBank accession No. U35004 (SEQ ID NO: 90)) and nt 663-706 of JNK1-132 (GenBank accession No. U35005 (SEQ ID NO: 91)) have the sequence shown below as SEQ ID NO: 68. For purposes of illustration, SEQ ID NOS: 67 and 68 are shown aligned with each other as follows:

```
5'-AAATGGTTTGCCACAAAATCCTCTTTCCAGGAAGGGACTATATT  SEQ ID NO: 67
   ||||| |              |  || ||||||   ||   |||||
5'-AAATGATCAAAGGTGGTGTTTTGTTCCCAGGTACAGATCATATT  SEQ ID NO: 68
```

Due to this divergence between the a and b JNK1 isoforms, antisense oligonucleotides derived from the reverse complement of SEQ ID NO: 67 (i.e., SEQ ID NO: 69, see below) are specifically hybridizable to in RNAs encoding, and can be selected and used to modulate the expression of, JNK1/JNK1-a1 and JNK1-a2 without significantly effecting the expression of JNK1-β1 and JNK1-β2. In like fashion, antisense oligonucleotides derived from the reverse complement of SEQ ID NO: 68 (i.e., SEQ ID NO: 70, see below) are specifically hybridizable to mRNAs encoding, and can be selected and used to modulate the expression of, can be selected and used to modulate the expression of JNK1-β1 and JNK1-β2 without significantly effecting the expression of JNK1/JNK1-a1 and JNK1-a2:

```
5'-AATATAGTCCCTTCCTGGAAAGAGGATTTTGTGGCAAACCATTT SEQ ID NO: 69
   |||||  ||  |  ||||||  ||  |  |        |  |||||
5'-AATATGATCTGTACCTGGGAACAAAACACCACCTTTGATCATTT SEQ ID NO: 70
```

In the case of the carboxyl terminal portion of the JNK1 isoforms, JNK1/JNK 1-a1 shares identity with JNK1-β1; similarly, JNK1-a2 and JNK1-β2 have identical carboxyterminal portions. The substantial differences in the amino acid sequences of these isoforms (5 amino acids in JNK1/JNK1-a1 and JNK1-β1 are replaced with 48 amino acids in JNK1-a2 and JNK1-β2) result from a slight difference in nucleotide sequence that shifts the reading frame. Specifically, in the ORFs of mRNAs encoding JNK1/JNK1-a1 and JNK1-131, nt 1144-1175 of JNK1/JNK1-a1 (Genbank accession No. L26318 (SEQ ID NO: 87)) and JNK1-β1 (Genbank accession No. U35004 (SEQ ID NO: 90)) have the sequence shown below as SEQ ID NO: 71, whereas, in the ORFs of mRNAs encoding JNK1-a2 and JNK1-β2, nt 1138-1164 of JNK1-a2 (GenBank accession No. U34822 (SEQ ID NO: 89)) and nt 1139-1165 of JNK1-132 (GenBank accession No. U35005 (SEQ ID NO: 91)) have the sequence shown below as SEQ ID NO: 72. For purposes of illustration, SEQ ID NOS: 71 and 72 are shown aligned with each other (dashes, A-," indicate bases that are absent in the indicated sequence, and emboldened bases indicate the stop codon for the JNK1/JNK1-a1 and JNK1-β1 ORFs):

```
5'-CCCTCTCCTTTAGCACAGGTGCAGCAGTGATC SEQ ID NO: 71
   ||||||||||||||     ||||||||||||||
5'-CCCTCTCCTTTAG-----GTGCAGCAGTGATC SEQ ID NO: 72
```

Due to this divergence between the JNK1 isoforms, antisense oligonucleotides derived from the reverse complement of SEQ ID NO: 71 (i.e., SEQ ID NO: 73, see below) are specifically hybridizable to mRNAs encoding, and can be selected and used to modulate the expression of, JNK1/JNK1-a1 and JNK1-β1 without significantly effecting the expression of JNK1-a2 and JNK1-β2. In like fashion, antisense oligonucleotides derived from the reverse complement of SEQ ID NO: 72 (i.e., SEQ ID NO: 74, see below) are specifically hybridizable to mRNAs encoding, and can be selected and used to modulate the expression of, JNK1-a2 and JNK1-β2 without significantly effecting the expression of JNK1/JNK1-a1 and JNK1-β1:

```
5'-GATCACTGCTGCACCTGTGCTAAAGGAGAGGG SEQ ID NO: 73
   ||||||||||||||     |||||||||||||
5'-GATCACTGCTGCAC-----CTAAAGGAGAGGG SEQ ID NO: 74
```

In preferred embodiments, such isoform-specific oligonucleotides such as are described above are methoxyethoxy "gapmers" or "wingmers" in which the RNase H-sensitive "gap" or "wing" is positioned so as to overlap a region of nonidentity in the above antisense sequences, i.e., SEQ ID NOS: 65, 66, 69, 70, 73 and 74.

Example 4

Oligonucleotide-Mediated Inhibition of JNK2 Expression

JNK2 oligonucleotide sequences: Table 8 lists the nucleotide sequences of oligonucleotides designed to specifically hybridize to JNK2 mRNAs and the corresponding ISIS and SEQ ID numbers thereof. The target gene nucleotide co-ordinates and gene target region are also included. The nucleotide co-ordinates are derived from GenBank accession No. L31951 (SEQ ID NO: 92), locus name "HUMJNK2" (see also FIG. 1(A) of Sluss et al., *Mol. Cel. Biol.,* 1994, 14, 8376, and Kallunki et al., *Genes & Development,* 1994, 8, 2996). The abbreviations for gene target regions are as follows: 5'-UTR, 5' untranslated region; tIR, translation initiation region; ORF, open reading frame; 3'-UTR, 3' untranslated region. The nucleotides of the oligonucleotides whose sequences are presented in Table 8 are connected by phosphorothioate linkages and are unmodified at the 2' position (i.e., 2-deoxy). It should be noted that the oligonucleotide target co-ordinate positions and gene target regions can vary within mRNAs encoding related isoforms of JNK2 (see subsection G, below).

In addition to hybridizing to human JNK2 mRNAs, the full oligonucleotide sequence of ISIS No. 12562 (SEQ ID NO: 33) hybridizes to the ORF of mRNAs from *Rattus norvegicus* that encode a stress-activated protein kinase named "p54a2" (Kyriakis et al., Nature, 1994, 369, 156). Specifically, ISIS 12562 (SEQ ID NO: 33) hybridizes to bases 649-668 of GenBank accession No. L27112 (SEQ ID NO: 93), locus name "RATSAPKB." This oligonucleotide is thus a preferred embodiment of the invention for investigating the role of the p54a2 protein kinase in rat in vitro, i.e., in cultured cells or tissues derived from whole animals, or in vivo.

JNK2-specific probes: In initial screenings of a set of oligonucleotides derived from the JNK2 sequence (Table 9) for biological activity, a cDNA clone of JNK2 (Kallunki et al., *Genes & Development,* 1994, 8, 2996) was radiolabeled and used as a JNK2-specific probe in Northern blots. Alternatively, however, one or more of the oligonucleotides of Table 8 is detectably labeled and used as a JNK2-specific probe.

Activities of JNK2 oligonucleotides: The data from screening a set of JNK2-specific phosphorothioate oligonucleotides (Table 9) indicate the following results. Oligonucleotides showing activity in this assay, as reflected by levels of inhibition of JNK2 mRNA levels of at least 50%, include ISIS Nos. 12558, 12559, 12560, 12563, 12564, 12565, 12566, 12567, 12568, 12569 and 12570 (SEQ ID NOS: 29, 30, 31, 34, 35, 36, 37, 38, 39, 40 and 41, respectively). These oligonucleotides are thus preferred embodiments of the invention for modulating JNK2 expression. Oligonucleotides showing levels of JNK2 mRNAs of at least 80% in this assay, include ISIS Nos. 12558, 12560, 12565, 12567, 12568 and 12569 (SEQ ID NOS: 29, 31, 36, 38, 39 and 40, respectively). These oligonucleotides are thus more preferred embodiments of the invention for modulating JNK2 expression.

The time course of inhibition of JNK2 mRNA expression by ISIS 12560 (SEQ ID NO: 31) is shown in Table 10. Following the 4 hour treatment with ISIS 12560, the level of inhibition of JNK2 was greater than or equal to about 80% for at least about 12 hours and greater than or equal to about 60% up to at least about t=48 h.

TABLE 10

Time Course of Response to JNK2 Antisense Oligonucleotides (ASOs)

| ISIS # | SEQ ID NO: | ASO Description | Time | Normalized % Control | % Inhibition |
|---|---|---|---|---|---|
| control | — | (LIPOFECTIN ™ only) | 0 h | 100.0 | 0.0 |
| control | — | (LIPOFECTIN ™ only) | 4 h | 100.0 | 0.0 |
| control | — | (LIPOFECTIN ™ only) | 12 h | 100.0 | 0.0 |
| control | — | (LIPOFECTIN ™ only) | 48 h | 100.0 | 0.0 |
| control | — | (LIPOFECTIN ™ only) | 72 h | 100.0 | 0.0 |
| 12560 | 31 | JNK2 active | 0 h | 20.2 | 79.8 |

TABLE 8

Nucleotide Sequences of JNK2 Oligonucleotides

| ISISNO. | NUCLEOTIDE SEQUENCE (5'→3') | SEQID NO: | TARGET GENE NUCLEOTIDE CO-ORDINATES | GENE TARGET REGION |
|---|---|---|---|---|
| 12558 | GTT-TCA-GAT-CCC-TCG-CCC-GC | 29 | 0003-0022 | 5'-UTR |
| 12559 | TGC-AGC-ACA-AAC-AAT-CCC-TT | 30 | 0168-0187 | ORF |
| 12560 | GTC-CGG-GCC-AGG-CCA-AAG-TC | 31 | 0563-0582 | ORF |
| 12561 | CAG-GAT-GAC-TTC-GGG-CGC-CC | 32 | 0633-0652 | ORF |
| 12562 | GCT-CTC-CCA-TGA-TGC-AAC-CC | 33 | 0691-0710 | ORF |
| 12563 | ATG-GGT-GAC-GCA-GAG-CTT-CG | 34 | 0997-1016 | ORF |
| 12564 | CTG-CTG-CAT-CTG-AAG-GCT-GA | 35 | 1180-1199 | ORF |
| 12565 | TGA-GAA-GGA-GTG-GCG-TTG-CT | 36 | 1205-1224 | ORF |
| 12566 | TGC-TGT-CTG-TGT-CTG-AGG-CC | 37 | 1273-1292 | ORF |
| 12567 | GGT-CCC-GTC-GAG-GCA-TCA-AG | 38 | 1295-1314 | ORF |
| 12568 | CAT-TTC-AGG-CCC-ACG-GAG-GT | 39 | 1376-1395 | 3'-UTR |
| 12569 | GGT-CTG-AAT-AGG-GCA-AGG-CA | 40 | 1547-1566 | 3'-UTR |
| 12570 | GGG-CAA-GTC-CAA-GCA-AGC-AT | 41 | 1669-1688 | 3'-UTR |

TABLE 9

Activities of JNK2 Oligonucleotides

| ISIS NO. | SEQ ID NO: | GENE TARGET REGION | % EXPRESSION | % INHIBITION |
|---|---|---|---|---|
| 12558 | 29 | 5'-UTR | 15% | 85% |
| 12559 | 30 | ORF | 28% | 72% |
| 12560 | 31 | ORF | 11% | 89% |
| 12561 | 32 | ORF | 60% | 40% |
| 12562 | 33 | ORF | 89% | 11% |
| 12563 | 34 | ORF | 22% | 78% |
| 12564 | 35 | ORF | 28% | 72% |
| 12565 | 36 | ORF | 19% | 81% |
| 12566 | 37 | ORF | 42% | 58% |
| 12567 | 38 | ORF | 18% | 82% |
| 12568 | 39 | 3'-UTR | 20% | 80% |
| 12569 | 40 | 3'-UTR | 13% | 87% |
| 12570 | 41 | 3'-UTR | 24% | 76% |

TABLE 10-continued

Time Course of Response to JNK2 Antisense Oligonucleotides (ASOs)

| ISIS # | SEQ ID NO: | ASO Description | Time | Normalized % Control | % Inhibition |
|---|---|---|---|---|---|
| 12560 | 31 | " | 4 h | 11.1 | 88.9 |
| 12560 | 31 | " | 12 h | 21.8 | 78.2 |
| 12560 | 31 | " | 48 h | 42.7 | 57.3 |
| 12560 | 31 | " | 72 h | 116.8 | (0.0) |

Additional JNK2 oligonucleotides: The results for JNK2-specific oligonucleotides (Table 9) indicate that one of the most active phosphorothioate oligonucleotides for modulating JNK2 expression is ISIS 12560 (SEQ ID NO: 31). As detailed in Table 11, additional oligonucleotides based on this oligonucleotide were designed to confirm and extend the findings described above.

Oligonucleotides ISIS Nos. 14318 (SEQ ID NO: 42) and 14319 (SEQ ID NO: 43) are 2'-deoxy-phosphorothioate sense strand and scrambled controls for ISIS 12560 (SEQ ID NO: 31), respectively. ISIS Nos. 15353 and 15354 are "gapmers" corresponding to ISIS 12560; both have 2'-methoxyethoxy "wings" (having phosphorothioate linkages in the case of ISIS 15353 and phosphodiester linkages in the case of ISIS 15354) and a central 2'-deoxy "gap" designed to support RNaseH activity on the target mRNA molecule. Similarly, ISIS Nos. 15355 to 15358 are "wingmers" corresponding to ISIS 12560 and have a 5' or 3' 2'-methoxyethoxy RNaseH-refractory "wing" and a 3' or 5' (respectively) 2-deoxy "wing" designed to support RNaseH activity on the target JNK2 mRNA.

The chemically modified derivatives of ISIS 12560 (SEQ ID NO: 31) were tested in the Northern assay described herein at concentrations of 100 and 400 nM, and the data (Table 12) indicate the following results. At 400 nM, relative to the 2'-unmodified oligonucleotide ISIS 12560, both "gapmers" (ISIS Nos. 15353 and 15354) effected approximately 80% inhibition of JNK2 mRNA expression. Similarly, the four "wingmers" (ISIS Nos. 155355 to 15358) effected 70-90% inhibition of JNK2 expression.

Dose- and sequence-dependent response to JNK2 oligonucleotides: In order to demonstrate a dose-dependent response to ISIS 12560 (SEQ ID NO: 31), different concentrations (i.e., 50, 100, 200 and 400 nM) of ISIS 12560 were tested for their effect on JNK2 mRNA levels in A549 cells (Table 13). In addition, two control oligonucleotides (ISIS 14318, SEQ ID NO: 42, sense control, and ISIS 14319, SEQ ID NO: 43, scrambled control; see also Table 11) were also applied to A549 cells in order to demonstrate the specificity of ISIS 12560. The results (Table 12) demonstrate that the response of A549 cells to ISIS 12539 is dependent on dose in an approximately linear fashion. In contrast, neither of the control oligonucleotides effect any consistent response on JNK2 mRNA levels.

TABLE 12

Activity of Chemically Modified JNK2 Antisense Oligonucleotides

| ISIS # | SEQ ID NO: | Oligonucleotide Description | Dose | Normalized % Control |
|---|---|---|---|---|
| control | — | No oligonucleotide (LIPOFECTIN ™ only) | — | 100.0 |
| 12560 | 31 | JNK2 active, fully P=S & | 100 nM | 62.1 |
| 12560 | 31 | fully 2-deoxy | 400 nM | 31.4 |
| 15352 | 31 | fully P=S & fully 2'-MOE | 100 nM | 132.4 |
| 15352 | 31 | | 400 nM | 158.4 |
| 15353 | 31 | gapmer: P=S, 2'-MOE wings; | 100 nM | 56.7 |
| 15353 | 31 | P=S, 2-deoxy core | 400 nM | 21.2 |
| 15354 | 31 | gapmer: P=O, 2'-MOE wings; | 100 nM | 38.3 |
| 15354 | 31 | P=S, 2-deoxy core | 400 nM | 17.1 |
| 15355 | 31 | wingmer: fully P=S; | 100 nM | 61.3 |
| 15355 | 31 | 5' 2'-MOE; 3' 2-deoxy | 400 nM | 29.1 |
| 15356 | 31 | wingmer: fully P=S; | 100 nM | 38.6 |
| 15356 | 31 | 5' 2-deoxy; 3' 2'-MOE | 400 nM | 11.0 |
| 15358 | 31 | wingmer: 5' P=O & 2'-MOE; | 100 nM | 47.4 |
| 15358 | 31 | 3' P=S & 2-deoxy | 400 nM | 29.4 |
| 15357 | 31 | wingmer: 5' P=S & 2'- | 100 nM | 42.8 |
| 15357 | 31 | deoxy; 3' P=O & 2'-MOE | 400 nM | 13.7 |

TABLE 13

Dose-Dependent Responses to JNK2 Antisense Oligonucleotides

| ISIS # | SEQ ID NO: | Oligonucleotide Description | Dose | Normalized % Control |
|---|---|---|---|---|
| control | — | No oligonucleotide (LIPOFECTIN ™ only) | — | 100.0 |
| 12560 | 31 | JNK2 active | 50 nM | 68.1 |
| 12560 | 31 | " | 100 nM | 50.0 |
| 12560 | 31 | " | 200 nM | 25.1 |

TABLE 11

Chemically Modified JNK2 Oligonucleotides

| ISISNO. | NUCLEOTIDE SEQUENCE (5'→3') AND CHEMICAL MODIFICATIONS* | SEQ ID NO: | COMMENTS |
|---|---|---|---|
| 12560 | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | active |
| 14318 | G$^S$A$^S$C$^S$T$^S$T$^S$T$^S$G$^S$G$^S$C$^S$C$^S$T$^S$G$^S$G$^S$C$^S$C$^S$C$^S$G$^S$G$^S$A$^S$C | 42 | 12560 sense control |
| 14319 | G$^S$T$^S$G$^S$C$^S$G$^S$C$^S$G$^S$C$^S$G$^S$A$^S$G$^S$C$^S$C$^S$C$^S$G$^S$A$^S$A$^S$A$^S$T$^S$C | 43 | scrambled control |
| | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | fully 2'-methoxyethoxy |
| | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | "gapmer" |
| | G$^O$T$^O$C$^O$C$^O$G$^S$G$^S$G$^S$C$^S$C$^S$A$^S$G$^S$G$^S$C$^S$C$^S$A$^O$A$^O$A$^O$G$^O$T$^O$C | 31 | "gapmer" |
| | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | "wingmer" |
| | G$^S$T$^S$C$^S$C$^S$G$^S$G$^S$G$^S$C$^S$C$^S$A$^S$G$^S$G$^S$C$^S$C$^S$A$^S$A$^S$A$^S$G$^S$T$^S$C | 31 | "wingmer" |
| 15358 | G$^O$T$^O$C$^O$C$^O$G$^O$G$^O$G$^O$C$^O$C$^O$A$^O$G$^O$G$^S$C$^S$C$^S$A$^S$A$^S$A$^S$G$^S$T$^S$C | 31 | "wingmer" |
| 15357 | G$^S$T$^S$C$^S$C$^S$G$^S$G$^S$G$^S$C$^S$C$^S$A$^O$G$^O$G$^O$C$^O$C$^O$A$^O$A$^O$A$^O$G$^O$T$^O$C | 31 | "wingmer" |
| 20572 | G$^S$T$^S$C$^S$C$^S$G$^S$G$^S$G$^S$<u>C</u>$^S$<u>C</u>$^S$A$^S$G$^S$G$^S$<u>C</u>$^S$<u>C</u>$^S$A$^S$A$^S$A$^S$G$^S$T$^S$C | 31 | fully 5-methyl-cytosine version of ISIS 15353 |

*Emboldened residues, 2'-methoxyethoxy-residues (others are 2'-deoxy-) including "C" residues, 5-methyl-cytosines; "$^O$", phosphodiester linkage; "$^S$", phosphorothioate linkage.
--- "<u>C</u>" residues, 2'-deoxy 5-methylcytosine residues; ---

TABLE 13-continued

Dose-Dependent Responses to JNK2 Antisense Oligonucleotides

| ISIS # | SEQ ID NO: | Oligonucleotide Description | Dose | Normalized % Control |
|---|---|---|---|---|
| 12560 | 31 | " | 400 nM | 14.2 |
| 14318 | 42 | 12560 sense control | 50 nM | 87.1 |
| 14318 | 42 | " | 100 nM | 89.8 |
| 14318 | 42 | " | 200 nM | 92.1 |
| 14318 | 42 | " | 400 nM | 99.6 |
| 14319 | 43 | 12560 scrambled control | 50 nM | 90.4 |
| 14319 | 43 | " | 100 nM | 93.7 |
| 14319 | 43 | " | 200 nM | 110.2 |
| 14319 | 43 | " | 400 nM | 100.0 |

Western Assays In order to assess the effect of oligonucleotides targeted to JNK2 mRNAs on JNK2 protein levels, Western assays are performed essentially as described above in Examples 2 and 3. A primary antibody that specifically binds to JNK2 is purchased from, for example, Santa Cruz Biotechnology, Inc., Santa Cruz, Calif.; Upstate Biotechnology, Inc., Lake Placid, N.Y.; StressGen Biotechnologies, Inc., Victoria, BC, Canada; or Research Diagnostics, Inc., Flanders, N.J.

Oligonucleotides specific for JNK2 isoforms: Subsequent to the initial descriptions of JNK2 (Sluss et al., *Mol. Cel. Biol.*, 1994, 14, 8376; Kallunki et al., *Genes & Development*, 1994, 8, 2996; GenBank accession No. HSU09759 (SEQ ID NO: 94), locus name "U09759 (SEQ ID NO: 94)"), cDNAs encoding related isoforms of JNK2 were cloned and their nucleotide sequences determined (Gupta et al., *EMBO Journal*, 1996, 15, 2760). In addition to JNK2-a2 (GenBank accession No. L31951 (SEQ ID NO: 92), locus name "HUMJNK2"), which encodes a polypeptide having an amino acid sequence identical to that of JNK2, the additional isoforms include JNK2-a1 (GenBank accession No. U34821 (SEQ ID NO: 95), locus name "HSU34821"), JNK2-β1 (GenBank accession No. U35002 (SEQ ID NO: 96), locus name "HSU35002") and JNK2-132 (GenBank accession No. U35003 (SEQ ID NO: 97), locus name "HSU35003"). The four isoforms of JNK2, which probably arise from alternative mRNA splicing, can each interact with different transcription factors or sets of transcription factors (Gupta et al., *EMBO Journal*, 1996, 15, 2760). As detailed below, the oligonucleotides of the invention are specific for certain members or sets of these isoforms of JNK2.

In the ORFs of mRNAs encoding JNK2/JNK2-a2 and JNK2-a1, nucleotides (nt) 689-748 of JNK2/JNK2-a2 (GenBank accession No. L31951 (SEQ ID NO: 92)) and nt 675-734 of JNK2-a1 (GenBank accession No. U34821 (SEQ ID NO: 95)) have the sequence shown below as SEQ ID NO: 75, whereas, in the ORFs of mRNAs encoding JNK2-β1 and JNK2-β2, nt 653-712 of JNK2-β1 (GenBank accession No. U35002 (SEQ ID NO: 96)) and nt 665-724 of JNK2-132 (GenBank accession No. U35003 (SEQ ID NO: 97)) have the sequence shown below as SEQ ID NO: 76. For purposes of illustration, SEQ ID NOS: 75 and 76 are shown aligned with each other (vertical marks, "|," indicate bases that are identical in both sequences):

```
5'-GTGGGTTGCATCATGGGAGAGCTGGTGAAAGGTTGTGTGATATTCCAAGGCACTGACCAT   SEQ ID NO: 75
   || ||  ||||||||||| |||  ||||      |   ||   | ||||  || |   ||| ||
5'-GTCGGGTGCATCATGGCAGAAATGGTCCTCCATAAAGTCCTGTTCCCGGGAAGAGACTAT   SEQ ID NO: 76
```

Due to this divergence between the a and b JNK2 isoforms, antisense oligonucleotides derived from the reverse complement of SEQ ID NO: 75 (i.e., SEQ ID NO: 77, see below) are specifically hybridizable to, and can be selected and used to modulate the expression of, JNK2/JNK2-a2 and JNK2-a1 without significantly effecting the expression of JNK1-β1 and JNK1-β2. In like fashion, antisense oligonucleotides derived from the reverse complement of SEQ ID NO: 76 (i.e., SEQ ID NO: 78, see below) are specifically hybridizable to, and can be selected and used to modulate the expression of, JNK2-β1 and JNK2-β2 without significantly effecting the expression of JNK2/JNK2-a2 and JNK2-a1. As an example, an oligonucleotide having a sequence derived from SEQ ID NO: 77 but not from SEQ ID NO: 78 is specifically hybridizable to, mRNAs encoding JNK1/JNK1-a1 and JNK1-a2 but not to those encoding JNK2-β1 and JNK2-β2:

```
                                                              SEQ ID NO:77
5'-ATGGTCAGTGCCTTGGAATATCACACAACCTTTCACCAGCTCTCCCATGATGCAACCCAC
   || |||   || ||  |||| |  ||    |     ||||   ||| |||||||||| || ||
5'-ATAGTCTCTTCCCGGGAACAGGACTTTATGGAGGACCATTTCTGCCATGATGCACCCGAC
                                                              SEQ ID NO:78
```

In the case of the carboxyl terminal portion of the JNK2 isoforms, JNK2/JNK2-a2 shares identity with JNK1-β2; similarly, JNK2-a1 and JNK2-β1 have identical carboxy terminal portions. The substantial differences in the amino acid sequences of these isoforms (5 amino acids in JNK2-a2 and JNK2-β2 are replaced with 47 amino acids in JNK2/JNK2-a2 and JNK2-β2) result from a slight difference in nucleotide sequence that shifts the reading frame. Specifically, in the ORFs of mRNAs encoding JNK2-a1 and JNK1-β1, nt 1164-1198 of JNK2-a1 (GenBank accession No. U34821 (SEQ ID NO: 95)) and nt 1142-1176 of JNK2-β1 (GenBank accession No. U35002 (SEQ ID NO: 96)) have the sequence shown below as SEQ ID NO: 79, whereas, in the ORFs of mRNAs encoding JNK2/JNK2-a2 and JNK2-β2, nt 1178-1207 of JNK2/JNK2-a2 (GenBank accession No. L31951 (SEQ ID NO: 92)) and nt 1154-1183 of JNK2-β2 (GenBank accession No. U35003 (SEQ ID NO: 97)) have the sequence shown below as SEQ ID NO: 80. For purposes of illustration, SEQ ID NOS: 79 and 80 are shown aligned with each other (dashes, "-," indicate bases that are absent in the indicated sequence, and emboldened bases indicate the stop codon for the JNK2-a1 and JNK2-β1 ORFs):

```
5'-GATCAGCCTTCAGCACAGATGCAGCAGTAAGTAGC          SEQ ID NO: 79
   |||||||||||||       ||||||||||||||||
5'-GATCAGCCTTCAG-----ATGCAGCAGTAAGTAGC          SEQ ID NO: 80
```

Due to this divergence between the JNK2 isoforms, antisense oligonucleotides derived from the reverse complement of SEQ ID NO: 79 (i.e., SEQ ID NO: 81, see below) are specifically hybridizable to, and can be selected and used to modulate the expression of, mRNAs encoding JNK2-a1 and JNK2-β1 without significantly effecting the expression of JNK2/JNK2-a2 and JNK2-β2. In like fashion, antisense oligonucleotides derived from the reverse complement of SEQ ID NO: 80 (i.e., SEQ ID NO: 82, see below) are specifically hybridizable to, and can be selected and used to modulate the expression of, mRNAs encoding JNK2/JNK2-a2 and JNK2-132 without significantly effecting the expression of JNK2-a1 and JNK2-β1. As an example, ISIS 12564 (SEQ ID NO: 35) corresponds to SEQ ID NO: 82 but not to SEQ ID NO: 81, and is thus specifically hybridizable to, and can be used to modulate the expression of, mRNAs encoding JNK2/JNK2-a2 and JNK2-β2 but not those encoding JNK2-a1 and JNK2-a1:

```
5'-GCTACTTACTGCTGCATCTGTGCTGAAGGCTGATC          SEQ ID NO: 81
   |||||||||||||||||      |||||||||||||
5'-GCTACTTACTGCTGCAT-----CTGAAGGCTGATC          SEQ ID NO: 82
         |||||||||||       ||||||||||||
      5'-CTGCTGCAT-----CTGAAGGCTGA              SEQ ID NO: 35
```

In preferred embodiments, such isoform-specific oligonucleotides such as are described above are methoxyethoxy "gapmers" or "wingmers" in which the RNase H-sensitive "gap" or "wing" is positioned so as to overlap a region of nonidentity in the above antisense sequences, i.e., SEQ ID NOS: 77, 78, 81 and 82.

Example 5

Oligonucleotide-Mediated Inhibition of JNK3 Expression

A. JNK3 oligonucleotide sequences: Table 14 lists the nucleotide sequences of oligonucleotides designed to specifically hybridize to JNK3 mRNAs and the corresponding ISIS and SEQ ID numbers thereof. The target gene nucleotide co-ordinates and gene target region are also included. The nucleotide co-ordinates are derived from GenBank accession No. U07620 (SEQ ID NO: 98), locus name "HSU07620" see also FIG. 4(A) of Mohit et al., Neuron, 1994, 14, 67). The abbreviations for gene target regions are as follows: 5'-UTR, 5' untranslated region; tIR, translation initiation region; ORF, open reading frame; 3'-UTR, 3' untranslated region. It should be noted that the oligonucleotide target co-ordinate positions and gene target regions can vary within mRNAs encoding related isoforms of JNK3 (see subsection D, below).

The nucleotides of the oligonucleotides whose sequences are presented in Table 14 are connected by phosphorothioate linkages and are "gapmers." Specifically, the six nucleotides of the 3' and 5' termini are 2'-methoxyethoxy-modified and are shown emboldened in Table 14, whereas the central eight nucleotides are unmodified at the 2' position (i.e., 2-deoxy).

In addition to hybridizing to human JNK3 mRNAs, the full oligonucleotide sequences of ISIS Nos. 16692, 16693, 16703, 16704, 16705, 16707, and 16708 (SEQ ID NOS: 46, 47, 56, 57, 58, 60 and 61, respectively) specifically hybridize to mRNAs from *Rattus norvegicus* that encode a stress-activated protein kinase named "p54β" (Kyriakis et al., Nature, 1994, 369, 156; GenBank accession No. L27128 (SEQ ID NO: 99), locus name "RATSAPKC." Furthermore, the full oligonucleotide sequences of 16692, 16693, 16695, 16703, 16704, 16705, 16707 and 16708 (SEQ ID NOS: 46, 47, 49, 56, 57, 58, 60 and 61, respectively) specifically hybridize to mRNAs from *Mus musculus* that encode a mitogen activated protein (MAP) kinase stress activated protein named the "p459$^{3F12}$ SAP kinase" (Martin et al., *Brain Res. Mol. Brain. Res.*, 1996, 35, 47; GenBank accession No. L35236 (SEQ ID NO: 100), locus name "MUSMAPK"). These oligonucleotides are thus preferred embodiments of the invention for investigating the role of the p54β and p459$^{3F12}$ SAP protein kinases in rat or mouse, respectively, in vitro, i.e., in cultured cells or tissues derived from whole animals or in vivo. The target gene nucleotide co-ordinates and gene target regions for these oligonucleotides, as defined for these GenBank entries, are detailed in Table 15.

JNK3-specific probes: In initial screenings of a set of oligonucleotides derived from the JNK3 sequence for biological activity, a cDNA clone of JNK3 (Derijard et al., *Cell*, 1994, 76, 1025) was radiolabeled and used as a JNK3-specific probe in Northern blots. Alternatively, however, one or more of the oligonucleotides of Table 14 is detectably labeled and used as a JNK3-specific probe.

Western Assays: In order to assess the effect of oligonucleotides targeted to JNK3 mRNAs on JNK3 protein levels, Western assays are performed essentially as described above in Examples 2 through 4. A primary antibody that specifically binds to JNK3 is purchased from, for example, Upstate Biotechnology, Inc. (Lake Placid, N.Y.), StressGen Biotechnologies Corp. (Victoria, BC, Canada), or New England Biolabs, Inc. (Beverly, Mass.).

TABLE 14

Nucleotide Sequences of JNK3 Oligonucleotides

| ISISNO. | NUCLEOTIDE SEQUENCE[1] (5'→3') | SEQ ID NO: | TARGET GENE NUCLEOTIDE CO-ORDINATES | GENE TARGET REGION |
|---|---|---|---|---|
| 16690 | TTC-AAC-AGT-TTC-TTG-CAT-AA | 44 | 0157-0176 | 5'-UTR |
| 16691 | CTC-ATC-TAT-AGG-AAA-CGG-GT | 45 | 0182-0200 | 5'-UTR |
| 16692 | TGG-AGG-CTC-ATA-AAT-ACC-AC | 46 | 0215-0234 | tIR |
| 16693 | TAT-AAG-AAA-TGG-AGG-CTC-AT | 47 | 0224-0243 | tIR |
| 16694 | TCA-CAT-CCA-ATG-TTG-GTT-CA | 48 | 0253-0272 | ORF |
| 16695 | TTA-TCG-AAT-CCC-TGA-CAA-AA | 49 | 0281-0300 | ORF |
| 16696 | GTT-TGG-CAA-TAT-ATG-ACA-CA | 50 | 0310-0329 | ORF |
| 16697 | CTG-TCA-AGG-ACA-GCA-TCA-TA | 51 | 0467-0486 | ORF |
| 16698 | AAT-CAC-TTG-ACA-TAA-GTT-GG | 52 | 0675-0694 | ORF |
| 16699 | TAA-ATC-CCT-GTG-AAT-AAT-TC | 53 | 0774-0793 | ORF |
| 16700 | GCA-TCC-CAC-AGA-CCA-TAT-AT | 54 | 0957-0976 | ORF |
| 16702 | TGT-TCT-CTT-TCA-TCC-AAC-TG | 55 | 1358-1377 | ORF |
| 16703 | TCT-CAC-TGC-TGT-TCA-CTG-CT | 56 | 1485-1504 | tIR |
| 16704 | GGG-TCT-GGT-CGG-TGG-ACA-TG | 57 | 1542-1561 | 3'-UTR |
| 16705 | AGG-CTG-CTG-TCA-GTG-TCA-GA | 58 | 1567-1586 | 3'-UTR |
| 16706 | TCA-CCT-GCA-ACA-ACC-CAG-GG | 59 | 1604-1623 | 3'-UTR |
| 16707 | GCG-GCT-AGT-CAC-CTG-CAA-CA | 60 | 1612-1631 | 3'-UTR |
| 16708 | CGC-TGG-GTT-TCG-CAG-GCA-GG | 61 | 1631-1650 | 3'-UTR |
| 16709 | ATC-ATC-TCC-TGA-AGA-ACG-CT | 62 | 1647-1666 | 3'-UTR |

[1]Emboldened residues are 2'-methoxyethoxy-modified.

TABLE 15

Rat and Mouse Gene Target Locations of JNK3 Oligonucleotides

| ISIS NO. | SEQ ID NO: | Rat NUCLEOTIDE CO-ORDINATES[1] | GENE TARGET REGION | Mouse NUCLEOTIDE CO-ORDINATES[2] | GENE TARGET REGION |
|---|---|---|---|---|---|
| 16692 | 46 | 0213-0232 | 5'-UTR | 0301-0320 | tIR |
| 16693 | 47 | 0222-0241 | 5'-UTR | 0310-0329 | tIR |
| 16695 | 49 | — | — | 0367-0386 | ORF |
| 16703 | 56 | 1506-1525 | ORF | 1571-1590 | tIR |
| 16704 | 57 | 1563-1582 | ORF | 1628-1647 | 3'-UTR |
| 16705 | 58 | 1588-1607 | ORF | 1653-1672 | 3'-UTR |
| 16707 | 60 | 1633-1652 | tTR | 1698-1717 | 3'-UTR |
| 16708 | 61 | 1652-1671 | 3'-UTR | 1717-1736 | 3'-UTR |

[1]Co-ordinates from GenBank Accession No. L27128 (SEQ ID NO: 99), locus name "RAT-SAPKC."
[2]Co-ordinates from GenBank Accession No. L35236 (SEQ ID NO: 100), locus name "MUSMAPK."

Oligonucleotides specific for JNK3 isoforms: Two isoforms of JNK3 have been described. JNK3-a1 was initially cloned and named "p49$^{3F12}$ kinase" by (Mohit et al. Neuron, 1995, 14, 67). Subsequently, two cDNAs encoding related isoforms of JNK3 were cloned and their nucleotide sequences determined (Gupta et al., *EMBO Journal*, 1996, 15, 2760). The isoforms are named JNK3-a1 (GenBank accession No. U34820 (SEQ ID NO: 101), locus name "HSU34820") and JNK3-a2 (GenBank accession No. U34819 (SEQ ID NO: 102), locus name "HSU34819") herein. The two isoforms of JNK3, which probably arise from alternative in RNA splicing, can each interact with different transcription factors or sets of transcription factors (Gupta et al., *EMBO Journal*, 1996, 15, 2760). As detailed below, certain oligonucleotides of the invention are specific for each of these isoforms of JNK3.

JNK3-a1 and JNK-a2 differ at their carboxyl terminal portions. The substantial differences in the amino acid sequences of these isoforms (5 amino acids in JNK3-a1 are replaced with 47 amino acids in JNK3-a2) result from a slight difference in nucleotide sequence that shifts the reading frame. Specifically, in the ORF of mRNAs encoding JNK3-a1, nucleotides (nt) 1325-1362 of JNK3-a1 (GenBank accession No. U34820 (SEQ ID NO: 101)) have the sequence shown below as SEQ ID NO: 83, whereas, in the ORF of mRNAs encoding JNK3-a2, nt 1301-1333 of JNK3-a2 (GenBank accession No. U34819 (SEQ ID NO: 102)) have the sequence shown below as SEQ ID NO: 84. For purposes of illustration, SEQ ID NOS: 83 and 202 are shown aligned with each other (vertical marks, "|," indicate bases that are identical in both sequences; dashes, "-," indicate bases that are absent in the indicated sequence; and emboldened bases indicate the stop codon for the JNK3-a1 ORF):

```
5'-GGACAGCCTTCTCCTTCAGCACAGGTGCAGCAGTGAAC        SEQ ID NO: 83
   |||||||||||||||||||    ||||||||||||||||
5'-GGACAGCCTTCTCCTTCAG-----GTGCAGCAGTGAAC        SEQ ID NO: 84
```

Due to this divergence between the JNK3 isoforms, antisense oligonucleotides derived from the reverse complement of SEQ ID NO: 83 (i.e., SEQ ID NO: 85, see below) are specifically hybridizable to mRNAs encoding JNK3-a1, and can be selected and used to modulate the expression of JNK3-a1 without significantly effecting the expression of JNK3-a2. In like fashion, antisense oligonucleotides derived from the reverse complement of SEQ ID NO: 84 (i.e., SEQ ID NO: 86, see below) are specifically hybridizable to mRNAs encoding JNK3-a2, and can be selected and used to modulate the expression of JNK3-a2 without significantly effecting the expression of JNK3-a1:

```
5'-GTTCACTGCTGCACCTGTGCTGAAGGAGAAGGCTGTCC        SEQ ID NO: 85
   ||||||||||||||    |||||||||||||||||||
5'-GTTCACTGCTGCAC-----CTGAAGGAGAAGGCTGTCC        SEQ ID NO: 86
```

In preferred embodiments, such isoform-specific oligonucleotides such as are described above are methoxyethoxy "gapmers" or "wingmers" in which the RNase H-sensitive "gap" or "wing" is positioned so as to overlap a region of nonidentity in the above antisense sequences, i.e., SEQ ID NOS: 85 and 86.

Activities of JNK3 oligonucleotides: The JNK3-specific phosphorothioate, 2'-methoxyethoxy "gapmer" oligonucleotides (Table 14) were screened for their ability to affect JNK3 mRNA levels in SH-SY5Y cells (Biedler et al., *Cancer Res.*, 1973, 33, 2643). SH-SY5Y cells express a variety of mitogen-activated protein kinases (MAPKs; see, e.g., Cheng et al., *J. Biol. Chem.*, 1998, 273, 14560). Cells were grown in DMEM essentially as previously described (e.g., Singleton et al., *J. Biol. Chem.*, 1996, 271, 31791; Jalava et al., *Cancer Res.*, 1990, 50, 3422) and treated with oligonucleotides at a concentration of 200 nM as described in Example 2. Control cultures were treated with an aliquot of LIPOFECTIN™ that contained no oligonucleotide.

The results are shown in Table 16. Oligonucleotides showing levels of inhibition of JNK3 mRNA levels of at least 45% include ISIS Nos. 16692, 16693, 16694, 16695, 16696, 16697, 16702, 16703, 16704, 16705 and 16706 (SEQ ID NOS: 46, 47, 48, 49, 50, 51, 55, 56, 57, 58 and 59, respectively). These oligonucleotides are preferred embodiments of the invention for modulating JNK3 expression. Oligonucleotides inhibiting JNK3 mRNAs by at least 60% in this assay include ISIS Nos. 16693, 16702, 16703 and 16704 (SEQ ID NOS: 47, 55, 56 and 57, respectively). These oligonucleotides are thus more preferred embodiments of the invention for modulating JNK3 expression.

TABLE 16

Activities of JNK3 Oligonucleotides

| ISISNo: | SEQ ID NO: | GENE TARGET REGION | % EXPRESSION: | % INHIBITION: |
|---|---|---|---|---|
| control[1] | — | — | 100% | 0% |
| 16690 | 44 | 5'-UTR | 60% | 40% |
| 16691 | 45 | 5'-UTR | 66% | 34% |

TABLE 16-continued

Activities of JNK3 Oligonucleotides

| ISISNo: | SEQ ID NO: | GENE TARGET REGION | % EXPRESSION: | % INHIBITION: |
|---|---|---|---|---|
| 16692 | 46 | tIR | 47% | 53% |
| 16693 | 47 | tIR | 40% | 60% |
| 16694 | 48 | ORF | 42% | 58% |
| 16695 | 49 | ORF | 44% | 56% |
| 16696 | 50 | ORF | 55% | 45% |

TABLE 16-continued

Activities of JNK3 Oligonucleotides

| ISISNo: | SEQ ID NO: | GENE TARGET REGION | % EXPRESSION: | % INHIBITION: |
|---|---|---|---|---|
| 16697 | 51 | ORF | 54% | 46% |
| 16698 | 52 | ORF | 63% | 37% |
| 16699 | 53 | ORF | 61% | 39% |
| 16700 | 54 | ORF | N.D.[2] | N.D. |
| 16702 | 55 | ORF | 39% | 61% |
| 16703 | 56 | tTR | 30% | 70% |
| 16704 | 57 | 3'-UTR | 36% | 64% |
| 16705 | 58 | 3'-UTR | 42% | 58% |
| 16706 | 59 | 3'-UTR | 45% | 55% |
| 16707 | 60 | 3'-UTR | 73% | 27% |
| 16708 | 61 | 3'-UTR | 68% | 32% |
| 16709 | 62 | 3'-UTR | 66% | 34% |

[1]Cells treated with LIPOFECTIN ™ only (no oligonucleotide).
[2]N.D., not determined.

Example 6

Oligonucleotides Targeted to Genes Encoding Rat JNK Proteins

In order to study the role of JNK proteins in animal models, oligonucleotides targeted to the genes encoding JNK1, JNK2 and JNK3 of *Rattus norvegicus* were prepared. These oligonucleotides are 2'-methoxyethoxy, phosphodiester/2'-hydroxyl, phosphorothioate/2'-methoxyethoxy, phosphodiester "gapmers" in which every cytosine residue is 5-methylcytosine (m5c). These antisense compounds were synthesized according to the methods of the disclosure. Certain of these oligonucleotides are additionally specifically hybridizable to JNK genes from other species as indicated herein. The oligonucleotides described in this Example were tested for their ability to modulate rat JNK mRNA levels essentially according to the methods described in the preceding Examples, with the exceptions that the cell line used was rat A 10 aortic smooth muscle cells (ATCC No. ATCC CRL-1476) and the probes used were specific for rat JNK1, JNK2 or JNK3 (see infra). A10 cells were grown and treated with oligonucleotides essentially as described by (Cioffi et al. *Mol. Pharmacol.*, 1997, 51, 383).

JNK1: Table 19 describes the sequences and structures of a set of oligonucleotides, ISIS Nos. 21857 to 21870 (SEQ ID NOS: 111 to 124, respectively) that were designed to be specifically hybridizable to nucleic acids from *Rattus norvegicus* that encode a stress-activated protein kinase named "p54?" or "SAPK?" that is homologous to the human protein JNK1 (Kyriakis et al., *Nature*, 1994, 369, 156; GenBank accession No. L27129 (SEQ ID NO: 88), locus name "RATSAPKD"). In Table 19, emboldened residues are 2'-methoxyethoxy-residues (others are 2'-deoxy-); "C" residues are 2'-methoxyethoxy-5-methyl-cytosines and "C" residues are 5-methyl-cytosines; "o" indicates a phosphodiester linkage; and "s" indicates a phosphorothioate linkage. The target gene co-ordinates are from GenBank Accession No. L27129 (SEQ ID NO: 88), locus name "RATSAPKD."

These antisense compounds were tested for their ability to modulate levels of (JNK1) and (JNK2) mRNA in A10 cells via Northern assays. Due to the high degree of sequence identity between the human and rat genes, radiolabeled human JNK1 (Example 3) and JNK2 (Example 4) cDNAs functioned as specific probes for the rat homologs.

The results are shown in Table 20. ISIS Nos. 21857 to 21870 (SEQ ID NOS: 111 to 124, respectively) showed 70% to 90% inhibition of rat JNK1 mRNA levels. These oligonucleotides are preferred embodiments of the invention for modulating rat JNK1 expression. Oligonucleotides showing levels of inhibition of at least 90% in this assay include ISIS Nos. 21858, 21859, 21860, 21861, 21862, 21864, 21865, 21866 and 21867 (SEQ ID NOS: 112, 113, 114, 115, 116, 118, 119, 120 and 121, respectively). These oligonucleotides are thus more preferred embodiments of the invention for modulating rat JNK1 expression. ISIS 21859 (SEQ ID NO: 113) was chosen for use in further studies (infra).

Two of the oligonucleotides, ISIS Nos. 21861 and 21867 (SEQ ID NOS: 115 and 121, respectively) demonstrated a capacity to modulate both JNK1 and JNK2. Such oligonucleotides are referred to herein as "Pan JNK" antisense compounds because the term "Pan" is used in immunological literature to refer to an antibody that recognizes, e.g., all isoforms of a protein or subtypes of a cell type. The Pan JNK oligonucleotides are discussed in more detail infra.

In addition to being specifically hybridizable to nucleic acids encoding rat JNK1, some of the oligonucleotides described in Table R-1 are also specifically hybridizable with JNK1-encoding nucleic acids from other species. ISIS 21859 (SEQ ID NO:113) is complementary to bases 4 to 23 of cDNAs encoding human JNK1α1 and JNK1β1 (i.e., GenBank accession Nos. L26318 (SEQ ID NO: 87) and U35004 (SEQ ID NO: 90), respectively). ISIS 21862 (SEQ ID NO: 116) is complementary to bases 294 to 313 of the human JNK1α1 and JNK1β1 cDNAs (GenBank accession Nos.

TABLE 19

Nucleotide Sequences of Rat JNK1 Oligonucleotides

| ISIS NO. | NUCLEOTIDE SEQUENCE (5'→3') | SEQ ID NO | TARGET GENE NUCLEOTIDE CO-ORDINATE | GENE TARGET REGION |
|---|---|---|---|---|
| 21857 | CoAoAoCoGsTsCsCsCsGsCsGsCsTsCsGoGoCoCoG | 111 | 0002-0021 | 5'-UTR |
| 21858 | CoCoToGoCsTsCsGsCsGsGsCsTsCsCsGoCoGoToT | 112 | 0029-0048 | 5'-UTR |
| 21859 | CoToCoAoTsGsAsTsGsGsCsAsAsGsCsAoAoToToA | 113 | 0161-0180 | tIR |
| 21860 | ToGoToToGsTsCsAsCsGsTsTsTsAsCsToToCoToG | 114 | 0181-0200 | ORF |
| 21861 | CoGoGoToAsGsGsCsTsCsGsCsTsTsAsGoCoAoToG | 115 | 0371-0390 | ORF |
| 21862 | CoToAoGoGsGsAsTsTsTsCsTsGsTsGsGoToGoToG | 116 | 0451-0470 | ORF |
| 21863 | CoAoGoCoAsGsAsGsTsGsAsAsGsGsTsGoCoToToG | 117 | 0592-0611 | ORF |
| 21864 | ToCoGoToTsCsCsTsGsCsAsGsTsCsCsToToGoCoC | 118 | 0691-0710 | ORF |
| 21865 | CoCoAoToTsTsCsTsCsCsCsAsTsAsAsToGoCoAoC | 119 | 0811-0830 | ORF |
| 21866 | ToGoAoAoTsTsCsAsGsGsAsCsAsAsGsGoToGoToT | 120 | 0901-0920 | ORF |
| 21867 | AoGoCoToTsCsGsTsCsTsAsCsGsGsAsGoAoToCoC | 121 | 1101-1120 | ORF |
| 21868 | CoAoCoToCsCsTsCsTsAsTsTsGsTsGoToGoCoToC | 122 | 1211-1230 | ORF |
| 21869 | GoCoToGoCsAsCsCsTsAsAsAsGsGsAsGoAoCoGoG | 123 | 1301-1320 | ORF |
| 21870 | CoCoAoGoAsGsTsCsGsGsAsTsCsTsGsToGoGoAoC | 124 | 1381-1400 | ORF |

L26318 (SEQ ID NO: 87) and U35004 (SEQ ID NO: 90), respectively), bases 289 to 308 of the human JNK1β2 cDNA (GenBank accession No. U35005 (SEQ ID NO: 91)), and bases 288 to 307 of the human JNK1a2 cDNA (GenBank accession No. U34822 (SEQ ID NO: 89)). Finally, ISIS 21865 is complementary to bases 654 to 673 of the human JNK1a1 cDNA (GenBank accession No. L26318 (SEQ ID NO: 87)) and to bases 648 to 667 of the human JNK1a2 cDNA (GenBank accession No. U34822 (SEQ ID NO: 89)). These oligonucleotides are tested for their ability to modulate mRNA levels of human JNK1 genes according to the methods described in Example 3.

TABLE 20

Activities of Oligonucleotides Targeted to Rat JNK1

| ISIS No: | SEQ ID NO: | GENE TARGET REGION | % EXPRESSION JNK1 | % EXPRESSION JNK2 |
|---|---|---|---|---|
| control[1] | — | — | 100% | 100% |
| 21857 | 111 | 5'-UTR | 24% | 91% |
| 21858 | 112 | 5'-UTR | 8% | 89% |
| 21859 | 113 | tIR | 5% | 106% |
| 21860 | 114 | ORF | 8% | 98% |
| 21861 | 115 | ORF | 6% | 13% |
| 21862 | 116 | ORF | 6% | 133% |
| 21863 | 117 | ORF | 24% | 107% |
| 21864 | 118 | ORF | 8% | 106% |
| 21865 | 119 | ORF | 5% | 50% |
| 21866 | 120 | ORF | 8% | 98% |
| 21867 | 121 | ORF | 5% | 21% |
| 21868 | 122 | ORF | 15% | 112% |

TABLE 20-continued

Activities of Oligonucleotides Targeted to Rat JNK1

| ISIS No: | SEQ ID NO: | GENE TARGET REGION | % EXPRESSION JNK1 | % EXPRESSION JNK2 |
|---|---|---|---|---|
| 21869 | 123 | ORF | 30% | 93% |
| 21870 | 124 | ORF | 11% | 87% |

[1]Cells treated with LIPOFECTIN ™ only (no oligonucleotide).

JNK2: Table 21 describes the sequences and structures of a set of oligonucleotides, ISIS Nos. 18254 to 18267 (SEQ ID NOS: 125 to 138, respectively) that were designed to be specifically hybridizable to nucleic acids that encode a stress-activated protein kinase from *Rattus norvegicus* that encode a stress-activated protein kinase named "p54a" or "SAPKa" (Kyriakis et al., Nature, 1994, 369, 156). The structures of three control oligonucleotides, ISIS Nos. 21914 to 21916 (SEQ ID NOS: 139 to 141, respectively) are also shown in the table. Two isoforms of p54a have been described: "p54a1" (GenBank accession No. L27112 (SEQ ID NO: 93), locus name "RATSAPKA") and "p54a2" (GenBank accession No. L27111 (SEQ ID NO: 104), locus name "RATSAPKB"). With the exception of ISIS 18257 (SEQ ID NO: 128), the oligonucleotides described in Table 21 are specifically hybridizable to nucleic acids encoding either p54a1 or p54a2. ISIS 18257 is specifically hybridizable to nucleic acids encoding p54a2 (i.e., GenBank accession No. L27112 (SEQ ID NO: 93), locus name "RATSAPKB"). In Table 21, emboldened residues are 2'-methoxyethoxy-residues (others are 2'-deoxy-); "C" residues are 2'-methoxyethoxy-5-methyl-cytosines and "C" residues are 5-methyl-cytosines; "o" indicates a phosphodiester linkage; and "s" indicates a phosphorothioate linkage. The target gene co-ordinates are from GenBank Accession No. L27112 (SEQ ID NO: 93), locus name "RATSAPKB."

TABLE 21

Nucleotide Sequences of Rat JNK2 Oligonucleotides

| ISIS NO. | NUCLEOTIDE SEQUENCE (5'→3') | SEQ ID NO: | TARGET GENE NUCLEOTIDE CO-ORDINATES | GENE TARGET REGION |
|---|---|---|---|---|
| 18254 | ToCoAoToGsAsTsGsTsAsGsTsGsTsCsAoToAoCoA | 125 | 0001-0020 | tIR |
| 18255 | ToGoToGoGsTsGsTsGsAsAsCsAsCsAsToToToAoA | 126 | 0281-0300 | ORF |
| 18256 | CoCoAoToAsTsGsAsAsTsAsAsCsCsTsGoAoCoAoT | 127 | 0361-0380 | ORF |
| 18257 | GoAoToAoTsCsAsAsCsAsTsTsCsTsCsCoToToGoT | 128 | 0621-0640 | ORF |
| 18258 | GoCoToToCsGsTsCsCsAsCsAsGsAsGsAoToCoCoG | 129 | 0941-0960 | ORF |
| 18259 | GoCoToCoAsGsTsGsGsAsCsAsTsGsGsAoToGoAoG | 130 | 1201-1220 | ORF |
| 18260 | AoToCoToGsCsGsAsGsGsTsTsTsCsAsToCoGoGoC | 131 | 1281-1300 | tIR |
| 18261 | CoCoAoCoCsAsGsCsTsCsCsCsAsTsGsToGoCoToC | 132 | 1341-1360 | 3'-UTR |
| 18262 | CoAoGoToTsAsCsAsCsAsTsGsAsTsCsToGoToCoA | 133 | 1571-1590 | 3'-UTR |

TABLE 21-continued

Nucleotide Sequences of Rat JNK2 Oligonucleotides

| ISIS NO. | NUCLEOTIDE SEQUENCE (5'→3') | SEQ ID NO: | TARGET GENE NUCLEOTIDE CO-ORDINATES | GENE TARGET REGION |
|---|---|---|---|---|
| 18263 | AoAoGoAoGsGsAsTsTsAsAsGsAsGsAs ToToAoToT | 134 | 1701-1720 | 3'-UTR |
| 18264 | AoGoCoAoGsAsGsTsGsAsAsAsTsAsCs AoAoCoToT | 135 | 2001-2020 | 3'-UTR |
| 18265 | ToGoToCoAsGsCsTsCsTsAsCsAsTsTs AoGoGoCoA | 136 | 2171-2190 | 3'-UTR |
| 18266 | AoGoToAoAsGsCsCsCsGsGsTsCsTsCs CoToAoAoG | 137 | 2371-2390 | 3'-UTR |
| 18267 | AoAoAoToGsGsAsAsAsAsGsGsAsCsAs GoCoAoGoC | 138 | 2405-2424 | 3'-UTR |
| 21914 | GoCoToCoAsGsTsGsGsAsTsAsTsGsGs AoToGoAoG | 139 | 18259 control— | |
| 21915 | GoCoToAoAsGsCsGsGsTsCsAsAsGsGs ToToGoAoG | 140 | 18259 control— | |
| 21916 | GoCoToCoGsGsTsGsGsAsAsAsTsGsGs AoToCoAoG | 141 | 18259 control— | |

TABLE 22

Activities of Oligonucleotides Targeted to Rat JNK2

| ISIS No: | SEQ ID NO: | GENE TARGET REGION | % EXPRESSION | % INHIBITION |
|---|---|---|---|---|
| control[1] | — | — | 100% | 0% |
| 18254 | 125 | tIR | 20% | 80% |
| 18255 | 126 | ORF | 21% | 79% |
| 18256 | 127 | ORF | 80% | 20% |
| 18257 | 128 | ORF | 32% | 68% |
| 18258 | 129 | ORF | 19% | 81% |
| 18259 | 130 | ORF | 15% | 85% |
| 18260 | 131 | ORF | 41% | 59% |
| 18261 | 132 | 3'-UTR | 47% | 53% |
| 18262 | 133 | 3'-UTR | 50% | 50% |
| 18263 | 134 | 3'-UTR | 63% | 37% |
| 18264 | 135 | 3'-UTR | 48% | 52% |
| 18265 | 136 | 3'-UTR | 38% | 62% |
| 18266 | 137 | 3'-UTR | 66% | 34% |
| 18267 | 138 | 3'-UTR | 84% | 16% |

[1]Cells treated with LIPOFECTIN ™ only (no oligonucleotide).

These antisense compounds were tested for their ability to modulate levels of p54a (JNK2) mRNA in A10 cells using the radiolabeled human JNK2 cDNA as a probe as described supra. The results are shown in Table 22. Oligonucleotides showing levels of inhibition from ≧ about 60% to about 100% of rat JNK2 mRNA levels include ISIS Nos. 18254, 18255, 18257, 18258, 18259, 18260 and 18265 (SEQ ID NOS: 125, 126, 128, 129, 130, 131 and 136, respectively). These oligonucleotides are preferred embodiments of the invention for modulating rat JNK2 expression. Oligonucleotides showing levels of inhibition of rat JNK1 mRNAs by at least 80% in this assay include ISIS Nos. 18254, 18255, 18258 and 18259 (SEQ ID NOS: 125, 126, 129 and 130, respectively). These oligonucleotides are thus more preferred embodiments of the invention for modulating rat JNK2 expression. ISIS 18259 (SEQ ID NO:130) was chosen for use in further studies (infra).

Dose Response: A dose response study was conducted using oligonucleotides targeted to rat JNK1 (ISIS 21859; SEQ ID NO: 113) and JNK2 (ISIS 18259; SEQ ID NO: 130) and Northern assays. The results (Table 23) demonstrate an increasing effect as the oligonucleotide concentration is raised and confirm that ISIS Nos. 21859 and 18259 (SEQ ID NOS: 113 and 130, respectively) specifically modulates levels of in RNA encoding JNK1 and JNK2, respectively.

TABLE 23

Dose-Dependent Response to Rat JNK Antisense Oligonucleotides (ASOs)

| ISIS # | SEQ ID NO: | ASO Description | Dose | % EXPRESSION JNK1 | % EXPRESSION JNK2 |
|---|---|---|---|---|---|
| 21859 | 113 | rat JNK1 active ASO | 0 nM | 100 | 100 |
| | | | 10 nM | 74 | 101 |
| | | | 50 nM | 25 | 98 |
| | | | 100 nM | 11 | 99 |
| | | | 200 nM | 8 | 101 |
| 18259 | 130 | rat JNK2 active ASO | 0 nM | 100 | 100 |
| | | | 10 nM | 95 | 81 |
| | | | 50 nM | 101 | 35 |
| | | | 100 nM | 94 | 15 |
| | | | 200 nM | 89 | 5 |

JNK3: Table 24 describes the sequences and structures of a set of oligonucleotides, ISIS Nos. 21899 to 21912 (SEQ ID NOS: 142 to 155, respectively) that were designed to be specifically hybridizable to nucleic acids from *Rattus norvegicus* that encode a stress-activated protein kinase named "p54β" that is homologous to the human protein JNK3 (Kyriakis et al., *Nature,* 1994, 369, 156; GenBank accession No. L27128 (SEQ ID NO: 99), locus name "RATSAPKC"). In Table 24, emboldened residues are 2'-methoxyethoxy-residues (others are 2'-deoxy-); "C" residues are 2'-methoxy-ethoxy-5-methyl-cytosines and "C" residues are 5-methyl-cytosines; "o" indicates a phosphodiester linkage; and "s" indicates a phosphorothioate linkage. The target gene coordinates are from GenBank Accession No. L27128 (SEQ ID NO: 99), locus name "RATSAPKC." The oligonucleotides are tested for their ability to modulate rat JNK3 mRNA levels essentially according to the methods described in the preceding Examples.

In addition to being specifically hybridizable to nucleic acids encoding rat JNK3, some of the oligonucleotides described in Table 24 are also specifically hybridizable with JNK3-encoding nucleic acids from humans and *Mus musculus* (mouse). Table 25 sets out these relationships. These oligonucleotides are tested for their ability to modulate mRNA levels of the human JNK genes according to the methods described in Example 5.

TABLE 25

Cross-Hybridizations of Rat JNK3 Oligonucleotides

| ISIS NO. | SEQ ID NO: | Hybridizes to: | | |
|---|---|---|---|---|
| | | Human JNK3a1[1] | Human JNK3a2[2] | MouseJNK3[3] |
| 21900 | 143 | — | — | bp 329-348 |
| 21901 | 144 | bp 193-212 | bp 169-188 | bp 411-430 |
| 21904 | 147 | — | — | bp 961-980 |
| 21905 | 148 | bp 943-962 | bp 919-938 | — |
| 21906 | 149 | — | — | bp 1381-1400 |
| 21908 | 151 | bp 1478-1497 | bp 1449-1468 | bp 1696-1715 |

[1]GenBank accession No. U34820 (SEQ ID NO: 101), locus name "HSU34820" (see also Mohit et al., Neuron, 1995, 14, 67 and Gupta et al., EMBO Journal, 1996, 15, 2760).
[2]GenBank accession No. U34819 (SEQ ID NO: 102), locus name "HSU34819" (see also Gupta et al., EMBO Journal, 1996, 15, 2760).
[3]Also known as p459[3F12] MAPK; GenBank accession No. L35236 (SEQ ID NO: 100), locus name "MUSMAPK" (see also Martin et al., Brain Res. Mol. Brain Res., 1996, 35, 47).

Pan JNK Oligonucleotides: Certain of the oligonucleotides of the invention are capable of modulating two or more JNK proteins and are referred to herein as "Pan JNK" oligonucleotides. For example, ISIS Nos. 21861 and 21867 (SEQ ID NOS: 115 and 121, respectively) demonstrated a capacity to modulate both JNK1 and JNK2 (Table 20). Such oligonucleotides are useful when the concomitant modulation of several JNK proteins is desired.

TABLE 24

Nucleotide Sequences of Rat JNK3 Oligonucleotides

| ISIS NO. | NUCLEOTIDE SEQUENCE (5'→3') | SEQ ID NO: | TARGET GENE NUCLEOTIDE CO-ORDINATES | GENE TARGET REGION |
|---|---|---|---|---|
| 21899 | GoGoGoCoTsTsTsCsAsTsTsAsGsCsCsAoCoAoToT | 142 | 0021-0040 | 5'-UTR |
| 21900 | GoGoToToGsGsTsTsCsAsCsTsGsCsAsGoToAoGoT | 143 | 0241-0260 | 5'-UTR |
| 21901 | ToGoCoToCsAsTsGsTsTsGsTsAsAsTsGoToToToG | 144 | 0351-0370 | tIR |
| 21902 | GoToCoGoAsGsGsAsCsAsGsCsGsTsCsAoToAoCoG | 145 | 0491-0510 | ORF |
| 21903 | CoGoAoCoAsTsCsCsGsCsTsCsGsTsGsGoToCoCoA | 146 | 0731-0750 | ORF |
| 21904 | AoCoAoToAsCsGsGsAsGsTsCsAsTsCsAoToGoAoA | 147 | 0901-0920 | ORF |
| 21905 | GoCoAoAoTsTsTsCsTsTsCsAsTsGsAsAoToToCoT | 148 | 1101-1120 | ORF |
| 21906 | ToCoGoToAsCsCsAsAsAsCsGsTsTsGsAoToGoToA | 149 | 1321-1340 | ORF |
| 21907 | CoGoCoCoGsAsGsGsCsTsTsCsCsAsGsGoCoToGoC | 150 | 1601-1620 | ORF |
| 21908 | GoGoCoToAsGsTsCsAsCsCsTsGsCsAsAoCoAoAoC | 151 | 1631-1650 | tIR |
| 21909 | GoCoGoToGsCsGsTsGsCsGsTsGsCsTsToGoCoGoT | 152 | 1771-1790 | 3'-UTR |
| 21910 | GoCoToCoAsGsCsTsGsCsGsAsTsAsCsAoGoAoAoC | 153 | 1891-1910 | 3'-UTR |
| 21911 | AoGoCoGoCsGsAsCsTsAsGsAsAsGsTsToAoAoGoT | 154 | 1921-1940 | 3'-UTR |
| 21912 | AoGoGoGoAsGsAsCsCsAsAsAsGsTsCsGoAoGoCoG | 155 | 1941-1960 | 3'-UTR |

Human Pan JNK oligonucleotides are described in Table 26. These oligonucleotides are designed to be complementary to sequences that are identically conserved in (i.e., SEQ ID NOS: 156, 158, 159, 160 and 161), or which occur with no more than a one-base mismatch (SEQ ID NO: 157), in nucleic acids encoding human JNK1a1, JNK1a2, JNK2a1 and JNK2a2. The oligonucleotides described in Table 26 are evaluated for their ability to modulate JNK1 and JNK2 mRNA levels in A549 cells using the methods and assays described in Examples 3 and 4.

In instances where such common sequences encompass one or more base differences between the JNK genes that it is desired to modulate, hypoxanthine (inosine) can be incorporated at the positions of the oligonucleotide corresponding to such base differences. ("Hypoxanthine" is the art-accepted term for the base that corresponds to the nucleoside inosine; however, the term "inosine" is used herein in accordance with U.S. and PCT rules regarding nucleotide sequences.) As is known in the art, inosine (I) is capable of hydrogen bonding with a variety of nucleobases and thus serves as a "universal" base for hybridization purposes. For example, an oligonucleotide having a sequence that is a derivative of SEQ ID NO:157 having one inosine substitution (TAGGAIATTCTTTCATGATC, SEQ ID NO:162) is predicted to bind to nucleic acids encoding human JNK1a1, JNK1a2, JNK2a1 and JNK2a2 with no mismatched bases. As another example, an oligonucleotide having a sequence that is a derivative of SEQ ID NO:161 having one inosine substitution (GGTTGCAITTTCTTCATGAA, SEQ ID NO:163) is predicted to bind with no mismatched bases to nucleic acids encoding human JNK3a1 and JNK3a2 in addition to JNK1a1, JNK1a2, JNK2a1 and JNK2a2. Such oligonucleotides are evaluated for their ability to modulate JNK1 and JNK2 mRNA levels in A549 cells, and JNK3 mRNA levels in SH-SY5Y cells, using the methods and assays described in Examples 3, 4 and 5.

TABLE 26

Human Pan JNK Oligonucleotides

| NUCLEOTIDE SEQUENCE (5'→3') AND CHEMICAL MODIFICATIONS* | SEQ ID NO: |
|---|---|
| A$^S$C$^S$A$^S$T$^S$C$^S$T$^S$T$^O$G$^O$A$^O$A$^O$A$^O$T$^O$T$^O$C$^S$T$^S$T$^S$C$^S$T$^S$A$^S$G | 156 |
| T$^S$A$^S$G$^S$G$^S$A$^S$T$^S$A$^O$T$^O$T$^O$C$^O$T$^O$T$^O$T$^O$C$^S$A$^S$T$^S$G$^S$A$^S$T$^S$C | 157 |
| A$^S$G$^S$A$^S$A$^S$G$^S$G$^S$T$^O$A$^O$G$^O$G$^O$A$^O$C$^O$A$^O$T$^S$T$^S$C$^S$T$^S$T$^S$T$^S$C | 158 |
| T$^S$T$^S$T$^S$A$^S$T$^S$T$^S$C$^O$C$^O$A$^O$C$^O$T$^O$G$^O$A$^O$T$^S$C$^S$A$^S$A$^S$T$^S$A$^S$T | 159 |
| T$^S$C$^S$A$^S$A$^S$T$^S$A$^S$A$^O$C$^O$T$^O$T$^O$T$^O$A$^O$T$^O$T$^S$C$^S$C$^S$A$^S$C$^S$T$^S$G | 160 |
| G$^S$G$^S$T$^S$T$^S$G$^S$C$^S$A$^O$G$^O$T$^O$T$^O$T$^O$C$^O$T$^O$T$^S$C$^S$A$^S$T$^S$G$^S$A$^S$A | 161 |

Emboldened residues, 2'-methoxyethoxy-residues (others are 2'-deoxy-); all "C" residues are 5-methyl-cytosines; "$^O$", phosphodiester linkage; "$^S$", phosphorothioate linkage.

Example 9

Effect of Oligonucleotides Targeted to Human JNK1 and JNK2 on TNFa-induced JNK Activity Human umbilical vein endothelial cells (HUVEC, Clonetics, San Diego Calif.) were incubated with oligonucleotide with LipofectinJ in Opti-MEMJ for 4 hours at 37° C./5% CON. The medium was then replaced with 1% FBS/EGM (Clonetics, Walkersville Md.) and incubated for 24 hours at 37° C./5% $CO_2$. Cells were treated with 5 ng/ml TNFa for 15 minutes before lysis. JNK activity was determined by incubating lysates (normalized for protein) with immobilized GST-c-Jun fusion protein (e.g., New England Biolabs, Beverly, Mass.)+$^{32}$P-ATP. GST-c-Jun beads were washed and SDS-PAGE sample buffer was added. Samples were resolved by SDS-PAGE and phosphorylated c-Jun was visualized using a Molecular Dynamics PhosphorImager.

Compared to a control oligonucleotide, the JNK1 oligonucleotide ISIS 15346 (SEQ ID NO: 16; 100 nM concentration) inhibited TNFa-induced JNK activity by approximately 70%. The JNK2 oligonucleotide ISIS 15353 (SEQ ID NO: 31; 100 nM) inhibited TNFa-induced JNK activity by approximately 55%. A combination of 50 nM each oligonucleotide inhibited TNFa-induced JNK activity by approximately 68% and a combination of 100 nM each oligonucleotide inhibited TNFa-induced JNK activity by approximately 83%.

Example 12

Inhibition of Inflammatory Responses by Antisense Oligonucleotides Targeting JNK Family Members JNKs have been implicated as key mediators of a variety of cellular responses and pathologies. JNKs can be activated by environmental stress, such as radiation, heat shock, osmotic shock, or growth factor withdrawal as well as by pro-inflammatory cytokines.

Antisense oligonucleotides targeting any of the JNK family members described in Examples 3-5 are synthesized and purified as in Example 1 and evaluated for their activity in inhibiting inflammatory responses. Such inhibition is evident in the reduction of production of pro-inflammatory molecules by inflammatory cells or upon the attenuation of proliferation of infiltrating or inflammatory cells, the most prominent of which are lymphocytes, neutrophils, macrophages and monocytes. Following synthesis, oligonucleotides are tested in an appropriate model system using optimal tissue or cell culture conditions. Inflammatory cells including lymphocytes, neutrophils, monocytes and macrophages are treated with the antisense oligonucleotides by the method of electroporation. Briefly, cells (5×10$^6$ cells in PBS) are transfected with oligonucleotides by electroporation at 200V, 000 uF using a BTX Electro Cell Manipulator 600 (Genetronics, San Diego, Calif.). For an initial screen, cells are electroporated with 10 uM oligonucleotide and RNA is collected 24 hours later. Controls without oligonucleotide are subjected to the same electroporation conditions.

Total cellular RNA is then isolated using the RNEASY7 kit (Qiagen, Santa Clarita, Calif.). RNAse protection experiments are conducted using RIBOQUANT™ kits and template sets according to the manufacturer's instructions (Pharmingen, San Diego, Calif.).

Adherent cells such as endothelial and A549 cells are transfected using the LIPOFECTIN™ protocol described in Example 2. Reduced JNK mRNA expression is measured by Northern analysis while protein expression is measured by Western blot analysis, both described in Example 1. Negative control oligonucleotides with mismatch sequences are used to establish baselines and non-specific effects.

The degree of inflammatory response is measured by determining the levels of inflammatory cytokine expression by Northern or Western analysis, or cytokine secretion by enzyme-linked immunosorbent assay (ELISA) techniques. Enzyme-linked immunosorbent assays (ELISA) are standard in the art and can be found at, for example, Ausubel, F. M. et al., *Current Protocols in Molecular Biology*, Volume 2, pp. 11.2.1-11.2.22, John Wiley & Sons, Inc., 1991.

The degree of inflammatory response is also determined by measuring the expression of known immediate-early genes by the method of Northern or Western blot analysis. Further into the inflammatory response, levels of apoptosis are measured by flow cytometry as described in Example 10.

Example 13

Inhibition of Fibrosis by Antisense Oligonucleotides Targeting JNK Family Members Pulmonary fibrosis is characterized by inflammatory and fibroproliferative changes in the lung and an excess accumulation of collagen in the interstitium. There is also an increased recruitment of immune and inflammatory cells to the lung which act not only in the initial damage to the lung but in the progression of the fibrotic process.

In the rodent bleomycin (BL)-induced pulmonary fibrosis model, inhibition of fibrosis in the lung is determined by measuring any of several markers for the condition. The BL-induced model is widely accepted in the art and can be found at, for example, Thrall, R. S. et al., Bleomycin In: *Pulmonary Fibrosis*, pp. 777-836, Eds. Phan, S. H. and Thrall, R. S., Marcel Dekker, New York, 1995 and Giri, S, N. et al., Miscellaneous mediator systems in pulmonary fibrosis In: *Pulmonary Fibrosis*, pp. 231-292, Eds. Phan, S. H. and Thrall, R. S., Marcel Dekker, New York, 1995.

Antisense oligonucleotides targeting any of the JNK family members described in Examples 3-5 are synthesized and purified as in Example 1 and evaluated for their ability to prevent or inhibit pulmonary fibrosis. These fibrotic markers include release of various pro-inflammatory mediators including cytokines and chemokines such as TNFa, interleukin-8 and interleukin-6, increased numbers of proteases and metalloproteinases, generation of reactive oxygen species (ROS), edema, hemorrhage and cellular infiltration predominated by neutrophils and macrophages.

Following synthesis, oligonucleotides are tested in the rodent BL-induced pulmonary fibrosis model using optimal conditions. Mice receive an intratracheal dose of bleomycin (0.125 U/mouse) or saline, followed by treatment with antisense oligonucleotide (i.p.) over 2 weeks. After 2 weeks mice are sacrificed and biochemical, histopathological and immunohistochemical analyses are performed.

Biochemical and immunohistochemical analysis involves the measurement of the levels of pro-inflammatory cytokine expression by Northern or Western analysis, or cytokine secretion by enzyme-linked immunosorbent assay (ELI SA) techniques as described in Example 12. Histopathological analyses are performed for the presence of fibrotic lesions in the BL-treated lungs and for the presence of and number of cells with the fibrotic phenotype by methods which are standard in the art.

Example 14

Sensitization to Chemotherapeutic Agents by Antisense Oligonucleotides Targeting JNK Family Members Manipulation of cancer chemotherapeutic drug resistance can also be accomplished using antisense oligonucleotides targeting JNK family members. Antisense oligonucleotides targeting any of the JNK family members described in Examples 3-5 are synthesized and purified as in Example 1 and evaluated for their ability to sensitize cells to the effects of chemotherapeutic agents. Sensitization is evident in the increased number of target cells undergoing apoptosis subsequent to treatment. Following synthesis, oligonucleotides are tested in an appropriate model system using optimal tissue or cell culture conditions. Cells are treated with the compounds of the invention in conjunction with one or more chemotherapeutic agents in a treatment regimen wherein the chemotherapeutic agents can be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide).

For nonadherent cells, treatment is by the method of electroporation. Briefly, cells ($5 \times 10^6$ cells in PBS) are transfected with oligonucleotides by electroporation either before, during or after treatment with the chemotherapeutic agent, at 200V, 1000 uF using a BTX Electro Cell Manipulator 600 (Genetronics, San Diego, Calif.). For an initial screen, cells are electroporated with 10 uM oligonucleotide and RNA is collected 24 hours later. Controls without oligonucleotide or chemotherapeutic agent are subjected to the same electroporation conditions.

Total cellular RNA is then isolated using the RNEASY7 kit (Qiagen, Santa Clarita, Calif.). RNAse protection experiments are conducted using RIBOQUANT™ kits and template sets according to the manufacturer's instructions (Pharmingen, San Diego, Calif.).

Adherent cells such as endothelial and A549 cells are transfected using the LIPOFECTIN™ protocol described in Example 2. Reduced JNK mRNA expression is measured by Northern analysis while protein expression is measured by Western blot analysis, both described in Example 1. Negative control oligonucleotides with mismatch sequences can be used to establish baselines and non-specific effects.

The degree of apoptosis, and consequently sensitization is measured by flow cytometry as described in Example 10.

Example 15

Oligonucleotide-Mediated Inhibition of Human JNK2 Expression Using a Cross-Species Oligonucleotide, ISIS 101759

In a further embodiment, chemical modifications to ISIS 18259 (SEQ ID NO: 130), designed to the rat JNK2 target were made and the oligonucleotide was investigated for activity in human cell lines.

The modified oligonucleotide, ISIS 101759, has identical base and sugar compositions as ISIS 18259 and differs only in the linker composition. ISIS 101759 contains phosphorothioate linkages throughout. A comparison of the two oligonucleotides is shown below.

"GoCoToCoAsGsTsGsGsAsCsAsTsGsGsAoToGoAoG"   ISIS 18259

"GsCsTsCsAsGsTsGsGsAsCsAsTsGsGsAsTsGsAsG"   ISIS 101759

Both oligonucleotides have the following base sequence 5'-GCTCAGTGGACATGGATGAG-3' and emboldened residues are 2'-methoxyethoxy-residues (others are 2'-deoxy-); "C" residues are 2'-methoxyethoxy-5-methyl-cytosines and "C" residues are 5-methyl-cytosines; "o" indicates a phosphodiester linkage; and "s" indicates a phosphorothioate linkage.

While ISIS 18259 was designed to target gene co-ordinates 1201-1220 from GenBank Accession No. L27112 (SEQ ID NO: 93) (herein incorporated as SEQ ID NO: 168), locus name "RATSAPKB as dileneated in Table 21, this same sequence is also complementary over 18 of its 20 nucleobases to coordinates 1248-1265 of human JNK2 from GenBank accession No. L31951 (SEQ ID NO: 92) (herein incorporated as SEQ ID NO: 167), locus name "HUMJNK2". The region of complementarity between ISIS 18259 (and consequently 101759 since it has the same base sequence as ISIS 18259) and the human gene is shown here in bold, 5'-GCTCAGTG-GACATGGATGAG-3'. In fact it is only the two nucleobases at the 3' end of the oligonucleotide that are not complementary to the human JNK2 gene.

Using three human cell lines, ISIS 101759 (SEQ ID NO: 130) was tested for its ability to reduce human JNK2 RNA levels. The control oligonucleotide for the three studies was ISIS 101760 (SEQ ID NO: 166; a 7-base mismatch). The control oligonucleoted has the same sugar and linker sequence as ISIS 101759 and the nucleobase sequence, 5'GsCsAsCsAsTsTsGsCsAsCsGsTsGsAsAsTsTsAsC-3', where emboldened residues are 2'-methoxyethoxy-residues (others are 2'-deoxy-); "C" residues are 2'-methoxyethoxy-5-methyl-cytosines and "C" residues are 5-methyl-cytosines; and "s" indicates a phosphorothioate linkage.

Inhibition of human JNK2 in HuVEC cells
HuVEC Cells:

The human umbilical vein endothelial cell line HuVEC was obtained from Clonetics (Clonetics Corporation Walkersville, Md.). HuVEC cells were routinely cultured in EBM (Clonetics Corporation Walkersville, Md.) supplemented with SingleQuots supplements (Clonetics Corporation, Walkersville, Md.). Cells were routinely passaged by trypsinization and dilution when they reached 90% confluence were maintained for up to 15 passages. Cells were seeded into 100 mm dishes and incubated overnight at 37° C./5% $CO_2$. (Falcon-Primaria #3872).

For Northern blotting or other analyses, cells can be seeded onto 100 mm or other standard tissue culture plates and treated similarly, using appropriate volumes of medium and oligonucleotide.

Treatment of HuVEC Cells with Antisense Compounds:

When cells reached 70% confluency, they were treated with oligonucleotide. For cells grown in 10 cm dishes, cells were washed once with 5 ml PBS and then treated with 5 ml of OPTI-MEM-1 containing 3 ul LIPOFECTIN (Invitrogen Corporation, Carlsbad, Calif.)/100 nM oligonucleotide/ml OPTI-MEM-1. For other oligonucleotide concentrations the oligonucleotide/Lipofectin ration was held constant. After 4-7 hours of treatment, the medium was replaced with fresh medium. Cells were harvested 16-24 hours after oligonucleotide treatment.

In accordance with the present invention, HuVEC cells were treated with 100 nM ISIS 101759 or the control oligonucleotide and mRNA levels of human JNK2 were monitored over a time-course of 0-72 hours and quantitated by Northern analysis. The data is shown in Table 29.

TABLE 29

Time-course Response to Rat JNK2 Antisense Oligonucleotides (ASOs) in HuVEC cells

| ISIS Number | Percent Inhibition of human JNK2 mRNA Expression | | | | |
|---|---|---|---|---|---|
| | 0 hr | 12 hr | 24 hr | 48 hr | 72 hr |
| Control | 0 | 6 | 7 | 23 | 16 |
| 101759 | 0 | 93 | 92 | 88 | 70 |

From the data, it is evident that the rat JNK2 oligonucleotide was capable of reducing the expression of human JNK2 in human HuVEC cells, and that by 72 hours the expression began to recover.

Inhibition of Human JNK2 in Hela Cells
Hela Cells:

The human cervix epithelial adenocarcinoma cell line HeLa was obtained from the American Type Culture Collection (Manassas, Va.). HeLa cells were routinely cultured in Minimum essential medium (Eagle) with 2 mM L-glutamine and Earle's BSS adjusted to contain 1.5 g/L sodium bicarbonate, 0.1 mM non-essential amino acids, and 1.0 mM sodium pyruvate, 90%; fetal bovine serum, 10% at a temperature of 37° C. Cells were seeded into 100 mm dishes and incubated overnight at 37° C./5% $CO_2$.

For Northern blotting or other analyses, cells can be seeded onto 100 mm or other standard tissue culture plates and treated similarly, using appropriate volumes of medium and oligonucleotide.

Treatment of Hela Cells with Antisense Compounds:

When cells reached 70% confluency, they were treated with oligonucleotide. For cells grown in 10 cm dishes, cells were washed once with 5 ml PBS and then treated with 5 ml of OPTI-MEM-1 containing 3 ul LIPOFECTIN (Invitrogen Corporation, Carlsbad, Calif.)/100 nM oligonucleotide/ml OPTI-MEM-1. For other oligonucleotide concentrations the oligonucleotide/Lipofectin ration was held constant. After 4-7 hours of treatment, the medium was replaced with fresh medium. Cells were harvested 16-24 hours after oligonucleotide treatment.

In accordance with the present invention, HeLa cells were treated with 10, 50 or 200 nM ISIS 101759 or the control oligonucleotide and mRNA levels of human JNK2 were quantitated by Northern analysis. The data is shown in Table 30.

TABLE 30

Dose Response to Rat JNK2 Antisense Oligonucleotides (ASOs) in HeLa cells

| ISIS No: | Percent Inhibition of human JNK2 mRNA | | |
|---|---|---|---|
| | 10 nM | 50 nM | 200 nM |
| Control | 0 | 0 | 1 |
| 101759 | 0 | 90 | 99 |

From the data, it is evident that the rat JNK2 oligonucleotide was capable of reducing the expression of human JNK2 in human HeLa cells in a dose-dependent manner. HeLa cells were also treated with the transfection reagent, lipofectamine, alone at 50 and 200 nM with no reduction in expression being observed.

Inhibition of Human JNK2 in Jurkat Cells

Jurkat Cells:

The human Jurkat cell line was obtained from the American Type Culture Collection (ATCC) (Manassas, Va.). Jurkat cells were routinely cultured in RPMI Medium 1640(Gibco/Life Technologies, Gaithersburg, Md.) supplemented with 20% fetal calf serum (Gibco/Life Technologies, Gaithersburg, Md.). Cells were routinely passaged by aspirating media that contained excess cells and replenishing with new media.

For electroporation, cells were diluted to $28 \times 10^6$ cells/mL and placed into 1 mm electroporation cuvettes. Electroporation is performed by treating with 1-20 μM oligonucleotide, at 160 Volts for 6 msec. The entire electroporated samples are then placed into 5 mL of 10% FBS/RPMI Medium 1640 in 100 mm plates. Plates are then left overnight at 37° C./5% $CO_2$.

Each sample is then transferred to 15 mL conical tubes and spun down at 1200 rpm for 5 minutes followed by aspiration of the supernatant. Cells are then suspended in 5 mL PBS followed by a second centrifugation at 1200 rpm for 5 minutes followed by aspiration of the supernatant. Cells are then washed and lysed. Following the lysis step, total cellular RNA is then isolated using the RNEASY kit (Qiagen, Santa Clarita, Calif.) as described in other examples herein.

In accordance with the present invention, Jurkat cells were treated by electroporation with 1, 5 or 20 uM ISIS 101759 or the control oligonucleotide and mRNA levels of human JNK2 were quantitated by Northern analysis. The data is shown in Table 31.

TABLE 31

Dose Response to Rat JNK2 Antisense Oligonucleotides (ASOs) in Jurkat cells

| ISIS No: | Percent Inhibition of human JNK2 mRNA | | |
|---|---|---|---|
| | 1 uM | 5 uM | 20 uM |
| Control | 12 | 18 | 19 |
| 101759 | 14 | 56 | 92 |

From the data, it is evident that the rat JNK2 oligonucleotide was capable of reducing the expression of human JNK2 in human Jurkat cells in a dose-dependent manner. Jurkat cells were also electroporated with reagents alone (no oligonucleotides) with no reduction in expression being observed.

Targeting JNK1 for Metabolic Disorders

Example 16

In vivo Studies in an ob/ob Model of Obesity

Leptin is a hormone produced by fat that regulates appetite. Deficiencies in this hormone in both humans and non-human animals leads to obesity. ob/ob mice have a mutation in the leptin gene which results in obesity and hyperglycemia. As such, these mice are a useful model for the investigation of obesity and metabolic syndrome and treatments designed to treat these conditions. ob/ob mice have higher circulating levels of insulin and are less hyperglycemic than db/db mice, which harbor a mutation in the leptin receptor. In accordance with the present invention, the oligomeric compounds of the invention are tested in the ob/ob model of obesity and diabetes.

Seven-week old male C57B1/6J-Lep ob/ob mice (Jackson Laboratory, Bar Harbor, Me.) were divided into a saline group (n=6), an oligonucleotide control group (n=6) and a treatment group (n=6). All animals were fed a diet with a fat content of 10-15% for 6 weeks. The oligonucleotide control group and the treatment group received a 25 mg/kg subcutaneous injection of either the control oligonucleotide or the treatment oligonucleotide twice a week for the 6 week period. The saline group received a saline injection on the same injection schedule. The control oligonucleotide in this study was a chimeric oligonucleotide that is 20 nucleosides in length and is not targeted to a nucleic acid encoding JNK. (CCTTCCCTGAAGGTTCCTCC, SEQ ID NO: 107, (Isis No. 141923). The treatment oligonucleotide is also a chimeric oligonucleotide that is 20 nucleotides in length, but it is targeted to a nucleic acid that encodes JNK1 polypeptide. The nucleic acid encoding JNK1 polypeptide has a nucleoside sequence that is substantially similar to GenBank Accession No.: L27129 (SEQ ID NO: 88).1; SEQ ID NO.: 88. The oligonucleotide compound is also targeted to a nucleic acid that encodes mouse JNK1 polypeptide with only a 1-nucleobase mismatch. The nucleic acid preferably being substantially similar to GenBank Accession No.: NM_016700.2; SEQ ID NO. 106. The treatment oligo contains the nucleobase sequence of TGTTGTCACGTTTACTTCTG, SEQ ID NO.: 114 (Isis No. 104492). The oligonucleotide compound is also targeted to a nucleic acid that encodes human JNK1 polypeptide with only a 2-nucleobase mismatch. The nucleic acid preferably being substantially similar to GenBank Accession NOs.: L26318 (SEQ ID NO: 87), U34822 (SEQ ID NO: 89), U35004 (SEQ ID NO: 90) or U35005 (SEQ ID NO: 91); SEQ ID NOs.: 87, 89, 90, and 91 respectively.

During the treatment period, weekly food intake was monitored, as were changes in body weight. Body composition, blood biochemistry, metabolic rate, insulin tolerance, and oral glucose tolerance was also measured at certain time points during the treatment period. After the treatment period, in mice were sacrificed and target in RNA levels were evaluated in liver, brown adipose tissue (BAT) and white adipose tissue (WAT), as were histological, biochemical and molecular biology parameters. RNA isolation and target mRNA expression level quantitation are performed as described by other examples herein unless otherwise stated.

mRNA Levels

Total RNA was isolated by homogenizing tissues in RLT buffer (Qiagen, Md.) followed by centrifugation with cesium chloride gradient. Real-time quantitative RT-PCR analysis was then performed to analyze the gene expression.

JNK1, but not JNK 2 in mRNA levels were reduced in the liver, white adipose tissue and brown adipiose tissue for the treatment group compared to saline and oligonucleotide control groups (80% reduction in liver, 80% reduction in WAT and 78% reduction in BAT). There were no significant differences in JNK1 mRNA levels between the saline and oligonucleotide control groups. Additionally, there were no significant differences in JNK2 mRNA levels between treatment, saline and oligonucleotide control groups. Thus, the treatment compound is specific for JNK1 over JNK2 in reducing mRNA expression.

JNK1 activity assay and Western immunoblotting analysis.

There was a corresponding reduction in JNK activity as determined by immunoprecipitation using an antibody raised to JNK1 (Cell Signaling, Beverly, Mass.). JNK1 ASO resulted in a decrease in JNK1 activity by greater than 95%, 80% and 65% in liver, WAT and BAT, respectively.

Feed Efficiency, Body Weight and Fat

As compared to control groups, the treatment group had an improved feed efficiency (change in body weight per volume of food intake). The treatment group feed efficiency was 0.052±0.0026 and the control oligonucleotide group was 0.060±0.002. The treatment group also showed a reduction in body weight gain by about 20%, indicating an increased metabolic rate. Epididymal fat pad weight (3.8 g v. 4.5 g) and whole body fat content (31.6% v. 35.5%) were also reduced. Indirect calorimetry measurement confirmed that the treatment group had an increased metabolic rate as reflected in a higher $VO_2$ as compared to the oligonucleotide control group ($VO_2$ increase over control group of >7% (greater than 7%) in the dark and 23% or greater in the light).

Glucose and Insulin Levels

Fed and fasting plasma glucose and plasma insulin levels were improved for the treatment group over the control group. (see Table 32). Glucose levels were completely normalized and insulin levels were lowered by greater than 50% after 6 weeks of treatment (Table 32) demonstrating increased insulin sensitization. Plasma glucose levels are measured using an Olympus Clinical Analysis (Olympus AU400, Olympus American Inc, Melville, N.Y.) and insulin levels are measure using an Alpco insulin-specific ELISA kit from (Windham, N.H.).

TABLE 32

Plasma Glucose and Insulin Levels in ob/ob Mice

| | | Saline | Control | ISIS 104492 |
|---|---|---|---|---|
| Glucose (mg/dl) | Baseline | 378.3 ± 33.0 | 374.2 ± 17.2 | 375.2 ± 33.7 |
| | Fed | 600.5 ± 48.7 | 445.5 ± 57.4 | 177.6 ± 12.3** |
| | Fasting | 142.7 ± 11.8 | 152.3 ± 23.5 | 90.6 ± 10.7* |
| Insulin (ng/ml) | Baseline | 30.2 ± 4.1 | 30.6 ± 3.7 | 29.8 ± 1.8 |
| | Fed | 24.4 ± 3.4 | 26.5 ± 5.8 | 11.0 ± 4.8* |
| | Fasting | 17.6 ± 1.8 | 16.9 ± 3.4 | 7.9 ± 0.4** |

Data are expressed as the mean ± SEM (n = 5-6).
*P < 0.05 and
**P < 0.01 when compared to either control group.

To confirm this ASO-caused insulin-sensitizing effect, both Glucose (OGTT) and insulin tolerance tests (ITT) were administered in fed and fasted mice. Mice receive intraperitoneal injections of either glucose or insulin, and the blood glucose and insulin levels are measured before the insulin or glucose challenge and at 15, or 30 minute intervals for up to 2 hours. Blood glucose levels were measured using a Glucometer (Abbott Laboratories, Bedford, Mass.).

Insulin tolerance and oral glucose tolerance was improved for the treatment group compared to the control groups. A glucose tolerance test in medical practice is the administration of glucose to determine how quickly it is cleared from the blood and is used to test for diabetes, insulin resistance, and sometimes reactive hypoglycemia. The results of an oral glucose tolerance test of the mice of Example 16 are shown in Table 33.

TABLE 33

OGTT performed at 6 weeks (0.75 g/kg Glucose)

| | Glucose mg/dL | | | |
|---|---|---|---|---|
| | 0 min | 30 min | 60 min | 100 min |
| Saline | 150 | 425 | 320 | 375 |
| Control | 150 | 420 | 325 | 300 |
| 104492 | 100 | 245 | 210 | 225 |

In response to glucose challenge, animals treated with JNK antisense oligonucleotide show improved glucose tolerance. Peak plasma glucose level at the 30 minute time point was decreased by over 40% from controls and the subsequent drop in glucose was lessened compared to controls. The AUC for glucose excursion was significantly lowered after treatment with JNK antisense oligonucleotide, indicating that inhibition of JNK by antisense improves glucose tolerance. The results indicate that glucose is cleared much more quickly from the blood of mice treated with JNK antisense oligonucleotide relative to the control groups. In addition, a markedly lower level of plasma insulin was observed during OGTT in the ASO treatment group versus controls (5 ng/ml JNK ASO treated vs 23 ng/ml saline treated).

An insulin tolerance test was also completed. There was an increase in rate and magnitude of glucose lowering after injecting insulin in the animals treated with JNK antisense oligonucleotide. AUC is reduced by about 50% by administration of JNK antisense oligonucleotide compared to saline treated control. These data demonstrate that reduction of JNK1 expression with JNK1 ASO significantly improved insulin sensitivity.

These date indicate that inhibition of JNK by antisense improves glucose tolerance and insulin sensitivity and, therefore, JNK1 antisense oligonucleotides are useful for treating, preventing and/or ameliorating disorders of or associated with glucose intolerance and/or insulin resistance, such as, for example, obesity, metabolic syndrome, diabetes, and hyperglycemia.

Liver Steatosis

To examine if the ASO treatment improved liver steatosis, both liver TG content and histology were analyzed.

Liver TG content was found to be greater than 40% lower in JNK ASO-treated group than in controls in ob/ob mice (120 mg/g vs 200 mg/g). Histological examinations with both H&E staining and oil-red O staining confirmed a significant improvement in liver steatosis in JNK1 ASO treated mice (much smaller and fewer fat droplets than those in controls). In addition, the histological examination did not reveal any sign of ASO-related liver damage. Rather, improved liver steatosis was accompanied by improved liver function, as assessed by plasma ALT and AST measurements (133.2±10.1 U/L ALT vs 311.5±21.1 and 113.2±8.2 U/LAST vs 187.8±14.6).

In addition to Liver steatosis, plasma transaminase levels and plasma cholesterol levels were improved for the treatment groups over the control group.

As compared to controls, treatment with JNK1 ASO for 6 weeks lowered plasma total cholesterol levels by 40% in ob/ob mice in the fed state. Lipoprotein profile analysis confirmed that JNK1 ASO treatment lowered the cholesterol content in all three major lipoprotein fractions, namely VLDL-, LDL- and HDL-cholesterol.

Plasma triglycerides, total cholesterol, HDL-cholesterol, LDL-cholesterol, free fatty acids and transaminases are measured by routine clinical analyzer instruments (e.g. Olympus Clinical Analyzer, Melville, N.Y.). Tissue triglyceride levels are measured using a Triglyceride GPO Assay from Roche Diagnostics (Indianapolis, Ind.). Liver triglyceride levels are used to assess hepatic steatosis, or clearing of lipids from the liver.

Hepatic steatosis is also assessed by routine histological analysis of frozen liver tissue sections stained with oil red 0 stain, which is commonly used to visualize lipid deposits, and counterstained with hematoxylin and eosin, to visualize nuclei and cytoplasm, respectively. For H&E staining, liver, epididymal WAT and intrascapular BAT samples from ob/ob mice were fixed in 10% buffered formalin and embedded in paraffin wax. For oil-red O staining, liver samples were collected in embedding medium. Multiple adjacent 4-μm sections were cut and mounted on glass slides. After dehydration, the sections were stained. Images of the histological sections were analyzed.

Metabolic Gene Expression

The ob/ob mice that received treatment were further evaluated at the end of the treatment period for the effects of target inhibition on the expression genes that participate in lipid metabolism, cholesterol biosynthesis, fatty acid oxidation, fatty acid storage, gluconeogenesis and glucose metabolism. Briefly, mRNA levels in liver and white and brown adipose tissue were quantitated by real-time PCR as described in other examples herein, employing primer-probe sets that are generated using published sequences of each gene of interest. The observations showed 1) increased in RNA levels of adrenoceptor .beta.3 by >2-fold and UCP1 mRNA by >1.2-fold in BAT; 2) reduced mRNA levels of ACC1, ACC2, FAS, SCD1, DGAT-1 and DGAT-2 by 30-60% in WAT; and 3) reduced mRNA levels of ACC1, FAS and G6Pase by >55%, and increased mRNA levels of both UCP2 and PPAR.alpha. by >2-fold in liver (see Table 35).

These data indicate that specific reduction of JNK1 expression with ASOs results in increased fuel combustion and decreased lipogenesis in this model. Thus, JNK1 appears to play an important role in whole body metabolism and therapeutic inhibition of JNK1 in major metabolic tissues could provide clinical benefit for obesity and metabolic syndrome.

Example 17

In vivo Studies in a Diet-Induced Model of Obesity (DIO)

To further confirm the metabolic effects of antisense suppression of JNK1 expression, DIO mice were also treated with JNK1 antisense oligonucleotides.

The C57BL/6 mouse strain is reported to be susceptible to hyperlipidemia-induced atherosclerotic plaque formation. Accordingly, these mice were fed a high-fat diet and used in the following studies to evaluate the effects of JNK1 antisense oligonucleotides on mRNA expression in a model of diet-induced obesity.

Male C57BL/6J mice at 6 weeks of age were fed a diet containing 58 kcal % fat (Research Diet D12330, Research Diets Inc., New Brunswick, N.J.) for 15 weeks to induce obesity and insulin resistance. The animals were then divided into different groups (n=6) and treated with JNK1 ASO or control ASO at a dose of 25 mg/kg BW or with saline twice a week for 7 weeks. Two JNK1 treatment oligonucleotides targeting two different region of JNK1 mRNA were used. The treatment oligonucleotides share the nucleobase sequence of SEQ ID NO.: 114, Isis No. 104492, or TGTTGT-CACGTTTGCTTCTG, SEQ ID NO: 108, ISIS NO. 256463. Each were given at the same dose. The control oligonucleotide is the same as described above. The treatment oligonucleotides are chimeric oligonucleotide 20 nucleotides in length, targeted to a nucleic acid that encodes JNK1 polypeptide. The nucleic acid encoding JNK1 polypeptide has a nucleoside sequence that is substantially similar to SEQ ID NO 87, 89, 90, 91.

During the treatment, weekly food intake and BW were monitored, and body composition and other metabolic measurements were conducted (see below). At the end of the studies, animals were sacrificed. Blood samples were collected by cardiac puncture, and tissues were dissected, weighed, and then saved for further analysis.

mRNA Levels

Total RNA was isolated by homogenizing tissues in RLT buffer (Qiagen, Md.) followed by centrifugation with cesium chloride gradient. Real-time quantitative RT-PCR analysis was then performed to analyze the gene expression. In DIO mice, treatment with 104492 reduced JNK1 mRNA by 78%, 66% and 70% in liver, WAT and BAT, respectively. Treatment with ISIS 256463 caused similar reduction of JNK1 expression in these tissues.

Plasma Glucose and Insulin Levels

Plasma insulin was measured with an insulin ELISA kit (ALPCO Diagnostics, Windham, N.H.). Plasma glucose were measured with a biochemistry analyzer (Olympus AU400, Olympus American Inc, Melville, N.Y.).

Treatment with JNK1 ASO lowered plasma glucose and insulin levels in both fed and fasted states when compared to controls (See Table 34). Treatment resulted in complete normalization of glucose levels and insulin levels in DIO mice confirming the improved insulin sensitivity shown in the ob/ob model.

TABLE 34

Plasma Glucose and Insulin Levels in DIO Mice

|  |  | Saline | Control | ISIS 104492 |
|---|---|---|---|---|
| Glucose (mg/dl) | Baseline | 207.2 ± 8.2 | 200.8 ± 9.7 | 206.3 ± 7.8 |
|  | Fed | 193.5 ± 9.8 | 189.0 ± 6.5 | 174.0 ± 4.2* |
|  | Fasting | 141.0 ± 8.6 | 124.3 ± 13.0 | 76.5 ± 6.4** |
| Insulin (ng/ml) | Baseline | 2.23 ± 0.13 | 2.41 ± 0.34 | 2.26 ± 0.12 |
|  | Fed | 2.51 ± 0.12 | 2.17 ± 0.39 | 0.75 ± 0.11** |
|  | Fasting | 1.30 ± 0.50 | 0.92 ± 0.21 | 0.48 ± 0.05** |

Data are expressed as the mean ± SEM (n = 5-6).
*P < 0.05 and
** P < 0.01 when compared to either control group.

Improved Hepatic Steatosis plasma transaminase (AST and ALT) activities were measured with a biochemistry analyzer (Olympus AU400, Olympus American Inc, Melville, N.Y.). Liver triglycerides (TG) was measured as previously described (Desai et al., 2001).

JNK1 ASO treatment lowered liver TG content by greater than 40% in DIO mice without causing liver toxicity, as assessed by plasma ALT and ASL activities.

Plasma Cholesterol Levels

Total cholesterol and FFA concentrations were measured with a biochemistry analyzer (Olympus AU400, Olympus American Inc, Melville, N.Y.).

As compared to controls, treatment with JNK1 ASO for 6 weeks lowered plasma total cholesterol levels by about 35% in DIO mice in the fasted state.

To investigate whether lowered plasma cholesterol levels with ASO treatment in the ob/ob and DIO models were caused by reducing hepatic synthesis and secretion, mouse primary hepatocytes were treated with JNK1 ASO and then de novo sterol synthesis was determined by measuring the incorporation of [14C]-acetate into sterols. JNK1 ASO transfected hepatocytes showed reduced de novo sterol synthesis by 13% as compared to controls. Furthermore, gene expression analysis found that JNK1 ASO-treated in mice had significantly lower hepatic ApoB100 mRNA levels versus controls. Reduction of ApoB100 expression has been well demonstrated to reduce plasma cholesterol levels in rodents and several other species. Therefore, without being bound by any theory, decreased plasma cholesterol levels can be at least in part due to decreased hepatic cholesterol output.

Feed Efficiency, Body Weight and Fat

In DIO mice, treatment with either of the two JNK1 oligonucleotides did not result in a change in food intake compared to controls. Treatment with JNK1 ASOs lowered BW by greater than 10%, which resulted in significant difference from the controls. Both JNK1 ASO-treated groups also showed greater than 35% lower epididymal fat depot weight and greater than 20% lower percentage body fat content with no difference on lean body mass.

Metabolic rate was measured for a 24-h period using indirect calorimetry (Oxymax System, Columbus Instruments, Columbus, Ohio). JNK1 ASO-treated mice had higher $VO_2$ than controls (about 12% or greater in the dark and about 4% or greater in the light).

Expression of Metabolic Genes

The expression of representative metabolic genes in DIO mice was analyzed. Similar changes as seen in ob/ob mice were founding the DIO mouse model. Additionally, about a 70% increase in the expression of both UCP2 and UCP3 in WAT was found in JNK1 treated DIO mice versus controls (see Table 35), further indicating that reduction of JNK1 expression not only inhibits lipogenesis but also increases metabolic rate.

Decreased De Novo Fatty Acid and Sterol Synthesis and Increased Fatty Acid Oxidation De novo fatty acid and sterol synthesis in transfected mouse hepatocytes were determined by measuring the incorporation of [$^{14}$C]acetate into fatty acids and sterols, respectively, as previously described (Jiang et al., 2005; Yu et al., 2005). Fatty acid oxidation was determined by measuring the oxidation of [$^{14}$C]oleate into acid soluble products and $CO_2$ as described (Choi et al., 2007; Savage et al., 2006; Yu et al., 1997; Yu et al., 2005).

To confirm that the JNK1 ASO-caused changes in gene expression translated into functional effects, cultured mouse primary hepatocytes were transfected with JNK1 ASO and fatty acid oxidation and de novo fatty acid synthesis were determined. Consistent with the changes in gene expression seen in vivo, fatty acid oxidation rate was about 35% higher or more whereas de novo fatty acid synthesis was about 20% lower in JNK1 ASO transfected cells than controls.

Improved Insulin Signaling

In support of the increased insulin sensitivity seen in the insulin and glucose tolerance tests in Example 16 above and the fed/fasted glucose and insulin measurements in both Example 16 and 17, mechanistic insulin signaling assays were performed. The enhanced insulin sensitivity resulting from reduction of JNK1 expression was verified by analyzing the activities of some key insulin signaling enzymes in both WAT and liver from DIO mice (treated with JNK1 ASO or control ASO and challenged with insulin).

DIO mice were treated with JNK1 ASO or control ASO at a dose of 37.5 mg/kg BW twice a week for 3 weeks. The mice were then fasted overnight and given a bolus i.p. injection of insulin at 2 U/kg BW or vehicle. The animals were then sacrificed, and liver and epididymal WAT were collected and quickly frozen in liquid $N_2$ for further analysis. Equal amount of total proteins contained in pre-cleared fat or liver homogenates were separated on gradient SDS-PAGE gels (BioRad, Hercules, Calif.) under reduced conditions and then transferred onto PVDF membranes. The blots were then incubated with primary antibody against Akt, Serine473-phosphorylated Akt (pAkt$^{Ser473}$) (Cell Signaling, Danvers, Mass.), or Ser302/307-phosphorylated IRS1 (pIRS1$^{Ser302/307}$) (Biosource, Camarillo, Calif.). Signals were then detected by using HRP-conjugated secondary antibody and ECL detection reagents (Amershan Biosciences).

A decreased level of pIRS$^{Ser302/307}$ was found not only under basal conditions (without insulin challenge) but also after insulin challenge in both tissues from JNK1 ASO-treated mice versus those from control ASO-treated mice. To evaluate whether decreased pIRS$^{Ser302/307}$ caused increased downstream insulin signaling activity, the level of pAkt$^{Ser473}$ in WAT was analyzed. A much higher level of pAkt$^{Ser473}$ was found in JNK1 ASO-treated mice versus controls after insulin challenge although its basal level was lower in the JNK1 ASO-treated mice; the latter was probably due to the lower plasma insulin levels in these mice. These data indicate that reduction of JNK1 expression with ASO improved insulin signaling activity which supports at least in part the increased insulin sensitivity detected in the tolerance tests and fed/fasted glucose and insulin measurements.

Statistical Analysis

Values presented represent the mean±SEM of three in vitro or 5-6 in vivo independent measures per treatment. Statistical difference between treatment groups was determined using one-way ANOVA with Tukey HSD multiple comparisons or two-tailed student t-test. P<0.05 was considered to be significant.

TABLE 35

Metabolic Gene Expression in ob/ob and DIO Mice

| Gene | Liver | | | WAT | | |
|---|---|---|---|---|---|---|
| | saline | control ASO | JNK1 ASO | saline | control ASO | JNK1 ASO |
| ACL | 100.0 ± 11.0 | 90.2 ± 7.7 | 54.0 ± 6.6** | | | |
| ACC1 | 100.0 ± 11.0 | 81.2 ± 12 | 34.3 ± 1.2** | | | |
| ACC2 | 100.0 ± 11 | 100.7 ± 15 | 121.1 ± 15 | 100.0 ± 9.6 | 77.6 ± 7.9 | 38.1 ± 3.7** |
| FAS | 100.0 ± 13.2 | 79.4 ± 13.3 | 44.3 ± 3.2** | 100.0 ± 4.1 | 110.7 ± 9.3 | 44.5 ± 3.7** |
| Gyk | 100.0 ± 6.2 | 106.3 ± 5.4 | 107.2 ± 6.4 | 100.0 ± 2.7 | 102.5 ± 4.6 | 65.8 ± 2.2** |
| SCD1 | 100.0 ± 28.4 | 78.3 ± 17.4 | 134.6 ± 12.3 | 100.0 ± 5.9 | 80.8 ± 4.3 | 45.3 ± 2.6** |
| DGAT1 | 100.0 ± 4.0 | 93.4 ± 2.3 | 113.4 ± 6.4 | 100.0 ± 3.1 | 90.3 ± 4.1 | 67.2 ± 5.1** |
| DGAT2 | 100.0 ± 9.8 | 119.6 ± 6.2 | 128 ± 6.7 | 100.0 ± 4.1 | 87.6 ± 3.7 | 67.4 ± 2.7** |
| HSL | | | | 100.0 ± 6.8 | 89.2 ± 6.2 | 91.1 ± 3.3 |
| ATGL | | | | 100.0 ± 4.2 | 88.1 ± 4.8 | 79.9 ± 11.7 |
| PPARα | 100.0 ± 51.9 | 130.2 ± 28.9 | 212.8 ± 7.1** | | | |
| UCP2 | 100.0 ± 11.1 | 110.2 ± 21.2 | 209.8 ± 49.6** | 100.0 ± 5.6 | 93 ± 5.1 | 110.3 ± 6.9 |
| ARβ3 | | | | 100.0 ± 7.3 | 152.3 ± 20 | 143.8 ± 20.5 |
| GK | 100.0 ± 7.2 | 97.3 ± 5.4 | 146.1 ± 16.6* | | | |
| G6Pase | 100.0 ± 3.0 | 92.1 ± 6.7 | 44.6 ± 3.3** | | | |
| GS | 100.0 ± 4.5 | 107.4 ± 7.7 | 185.3 ± 16.6** | | | |

TABLE 35-continued

Metabolic Gene Expression in ob/ob and DIO Mice

| | Liver | | | WAT | | |
| --- | --- | --- | --- | --- | --- | --- |
| Gene | saline | control ASO | JNK1 ASO | saline | control ASO | JNK1 ASO |
| PKCε | 100.0 ± 8.9 | 84.2 ± 5.3 | 62.1 ± 8.3* | | | |
| RBP4 | | | | 100.0 ± 13.9 | 118.7 ± 7.3 | 63.2 ± 11.2* |
| ApoB100 | 100.0 ± 10.2 | 99.1 ± 8.9 | 75.1 ± 2.5* | | | |

The analysis was performed with quantitative RT-PCR. Total RNA was isolated from tissues of ob/ob mice treated with JNK1 ASO or control ASO at 25 mg/kg BW or with saline twice a week for 6 weeks. Data are expressed as the mean ± SEM (n = 5-6).
*P < 0.05 and
**P < 0.01 when compared to either control group.

---

What is claimed is:

1. A method of reducing lipid levels in a subject in need thereof, comprising administering to the subject a therapeutically effective amount of an antisense compound targeted to a JNK1 nucleic acid, thereby reducing lipid levels.

2. The method of claim 1, wherein the administering further results in a reduction in glucose levels, body weight, adiposity, or an increase in metabolic rate or insulin sensitivity or any combination thereof.

3. The method of claim 1, wherein the lipid levels are triglyceride or cholesterol or a combination thereof.

4. The method of claim 1, wherein the subject has Type 2 diabetes.

5. The method of claim 2, wherein the administering further results in reducing glucose levels or improving insulin sensitivity or both.

6. A method of treating obesity or metabolic syndrome in a subject comprising administering to said subject a lipid-lowering agent and a therapeutically effective amount of an antisense compound targeted to a JNK 1 nucleic acid, wherein said antisense compound targeted to said JNK 1 nucleic acid reduces lipid levels in said subject, thereby treating obesity or metabolic syndrome.

7. The method of claim 6, wherein said lipid-lowering agent is a HMG-CoA reductase inhibitor or a cholesterol absorption inhibitor.

8. The method of claim 7, wherein the HMG-CoA reductase inhibitor is a statin.

9. The method of claim 8, wherein the statin is atorvastatin, simvastatin, pravastatin, fluvastatin or rosuvastatin.

10. The method of claim 7, wherein the cholesterol absorption inhibitor is ezetimibe.

11. The method of claim 1, wherein the administering comprises parenteral administration.

12. The method of claim 11, wherein the parenteral administration comprises subcutaneous or intravenous administration.

13. The method of claim 1, wherein the antisense compound is complementary to SEQ ID NO: 87, 89, 90 or 91.

14. The method of claim 1, wherein the antisense compound is 12 to 30 nucleosides in length.

15. The method of claim 1, wherein the antisense compound is an antisense oligonucleotide.

16. The method of claim 1, wherein the antisense compound comprises at least one modified sugar moiety.

17. The method of claim 16, wherein the modified sugar moiety is a 2'-O-methoxyethyl sugar moiety.

18. The method of claim 1, wherein the antisense compound comprises at least one modified internucleoside linkage.

19. The method of claim 18, wherein each internucleoside linkage of the antisense compound is a phosphorothioate internucleoside linkage.

20. The method of claim 1, wherein the antisense compound comprises at least one modified nucleobase.

21. The method of claim 1, wherein each cytosine of the antisense compound is a 5-methylcytosine.

22. The method of claim 1, wherein the antisense compound is a gapmer antisense oligonucleotide.

23. The method of claim 22, wherein the antisense compound is a gap-widened antisense oligonucleotide.

24. The method of claim 1, wherein the antisense oligonucleotide comprises a gap segment of ten 2'-deoxynucleotides positioned between wing segments of five 2'-O-methoxyethyl modified nucleosides.

25. The method of claim 1, wherein the subject has hyperlipidemia.

26. The method of claim 13, wherein the antisense compound has 100% complementarity to SEQ ID NO: 87, 89, 90 or 91.

27. The method of claim 25, wherein hyperlipidemia is hypercholesterolemia, hypertriglyceridemia or hyperfattyacidemia.

28. The method of claim 6, wherein the administering further results in reducing glucose levels or improving insulin sensitivity or both.

29. The method of claim 1, wherein the subject is obese.

30. The method of claim 1, wherein the subject has metabolic syndrome.

* * * * *

SEQUENCE LISTING

```
<160> NUMBER OF SEQ ID NOS: 163

<210> SEQ ID NO 1
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 1
attctttcca ctcttctatt                                                 20

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
ctcctccaag tccataactt                                                 20

<210> SEQ ID NO 3
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 3
cccgtataac tccattcttg                                                 20

<210> SEQ ID NO 4
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 4
ctgtgctaaa ggagagggct                                                 20

<210> SEQ ID NO 5
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 5
atgatggatg ctgagagcca                                               20

<210> SEQ ID NO 6
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 6
gttgacattg aagacacatc                                               20

<210> SEQ ID NO 7
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 7
ctgtatcaga ggccaaagtc                                               20

<210> SEQ ID NO 8
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 8
tgctgcttct agactgctgt                                               20

<210> SEQ ID NO 9
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 9
agtcatctac agcagcccag                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 10
ccatccctcc caccccccga                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 11
atcaatgact aaccgactcc                                               20
```

```
<210> SEQ ID NO 12
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 12
caaaaataag accactgaat                                                    20

<210> SEQ ID NO 13
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 13
cacgcttgct tctgctcatg                                                    20

<210> SEQ ID NO 14
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 14
cggcttagct tcttgattgc                                                    20

<210> SEQ ID NO 15
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 15
cccgcttggc atgagtctga                                                    20

<210> SEQ ID NO 16
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 16
ctctctgtag gcccgcttgg                                                    20

<210> SEQ ID NO 17
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 17
atttgcatcc atgagctcca                                                    20

<210> SEQ ID NO 18
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 18
cgttcctgca gtcctggcca                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 19
ggatgacctc gggtgctctg                                              20

<210> SEQ ID NO 20
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 20
cccataatgc accccacaga                                              20

<210> SEQ ID NO 21
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 21
cgggtgttgg agagcttcat                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 22
tttggtggtg gagcttctgc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 23
ggctgccccc gtataactcc                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 24
tgctaaagga gagggctgcc                                              20
```

```
<210> SEQ ID NO 25
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 25
aggccaaagt cggatctgtt                                                  20

<210> SEQ ID NO 26
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 26
ccaccccccg atggcccaag                                                  20

<210> SEQ ID NO 27
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 27
ccaagcgggc ctacagagag                                                  20

<210> SEQ ID NO 28
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 28
ctttccgttg gacccctggg                                                  20

<210> SEQ ID NO 29
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 29
gtttcagatc cctcgcccgc                                                  20

<210> SEQ ID NO 30
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 30
tgcagcacaa acaatccctt                                                  20

<210> SEQ ID NO 31
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 31
gtccgggcca ggccaaagtc                                               20

<210> SEQ ID NO 32
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 32
caggatgact tcgggcgccc                                               20

<210> SEQ ID NO 33
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 33
gctctcccat gatgcaaccc                                               20

<210> SEQ ID NO 34
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 34
atgggtgacg cagagcttcg                                               20

<210> SEQ ID NO 35
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 35
ctgctgcatc tgaaggctga                                               20

<210> SEQ ID NO 36
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 36
tgagaaggag tggcgttgct                                               20

<210> SEQ ID NO 37
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 37
tgctgtctgt gtctgaggcc                                               20

```
<210> SEQ ID NO 38
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 38
ggtcccgtcg aggcatcaag                                               20

<210> SEQ ID NO 39
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 39
catttcaggc ccacggaggt                                               20

<210> SEQ ID NO 40
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 40
ggtctgaata gggcaaggca                                               20

<210> SEQ ID NO 41
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 41
gggcaagtcc aagcaagcat                                               20

<210> SEQ ID NO 42
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 42
gactttggcc tggcccggac                                               20

<210> SEQ ID NO 43
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 43
gtgcgcgcga gcccgaaatc                                               20

<210> SEQ ID NO 44
<211> LENGTH: 20
<212> TYPE: DNA
<213> ORGANISM: Artificial Sequence
<220> FEATURE:
<223> OTHER INFORMATION: Synthetic Oligonucleotide
```

-continued

<400> SEQUENCE: 44
ttcaacagtt tcttgcataa                                       20

<210> SEQ ID NO 45
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 45
ctcatctata ggaaacgggt                                       20

<210> SEQ ID NO 46
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 46
tggaggctca taaataccac                                       20

<210> SEQ ID NO 47
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 47
tataagaaat ggaggctcat                                       20

<210> SEQ ID NO 48
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 48
tcacatccaa tgttggttca                                       20

<210> SEQ ID NO 49
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 49
ttatcgaatc cctgacaaaa                                       20

<210> SEQ ID NO 50
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 50
gtttggcaat atatgacaca                                       20

```
<210> SEQ ID NO 51
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 51
ctgtcaagga cagcatcata                                                 20

<210> SEQ ID NO 52
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 52
aatcacttga cataagttgg                                                 20

<210> SEQ ID NO 53
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 53
taaatccctg tgaataattc                                                 20

<210> SEQ ID NO 54
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 54
gcatcccaca gaccatatat                                                 20

<210> SEQ ID NO 55
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 55
tgttctcttt catccaactg                                                 20

<210> SEQ ID NO 56
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 56
tctcactgct gttcactgct                                                 20

<210> SEQ ID NO 57
<211> LENGTH: 20
<212> TYPE: DNA
<213> ORGANISM: Artificial Sequence
<220> FEATURE:
<223> OTHER INFORMATION: Synthetic Oligonucleotide
```

```
<400> SEQUENCE: 57
gggtctggtc ggtggacatg                                               20

<210> SEQ ID NO 58
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 58
aggctgctgt cagtgtcaga                                               20

<210> SEQ ID NO 59
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 59
tcacctgcaa caacccaggg                                               20

<210> SEQ ID NO 60
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 60
gcggctagtc acctgcaaca                                               20

<210> SEQ ID NO 61
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 61
cgctgggttt cgcaggcagg                                               20

<210> SEQ ID NO 62
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 62
atcatctcct gaagaacgct                                               20

<210> SEQ ID NO 63
<211> LENGTH: 35
<212> TYPE: DNA
<213> ORGANISM: Homo sapien

<400> SEQUENCE: 63
aacgtggatt tatggtctgt ggggtgcatt atggg                              35

<210> SEQ ID NO 64
<211> LENGTH: 35
<212> TYPE: DNA
<213> ORGANISM: Homo sapien
```

```
<400> SEQUENCE: 64
aacgttgaca tttggtcagt tgggtgcatc atggg                             35

<210> SEQ ID NO 65
<211> LENGTH: 35
<212> TYPE: DNA
<213> ORGANISM: Homo sapien

<400> SEQUENCE: 65
cccataatgc accccacaga ccataaatcc acgtt                             35

<210> SEQ ID NO 66
<211> LENGTH: 35
<212> TYPE: DNA
<213> ORGANISM: Homo sapien

<400> SEQUENCE: 66
cccatgatgc acccaactga ccaaatgtca acgtt                             35

<210> SEQ ID NO 67
<211> LENGTH: 44
<212> TYPE: DNA
<213> ORGANISM: Homo sapien

<400> SEQUENCE: 67
aaatggtttg ccacaaaatc ctctttccag gaagggacta tatt                   44

<210> SEQ ID NO 68
<211> LENGTH: 44
<212> TYPE: DNA
<213> ORGANISM: Homo sapien

<400> SEQUENCE: 68
aaatgatcaa aggtggtgtt ttgttcccag gtacagatca tatt                   44

<210> SEQ ID NO 69
<211> LENGTH: 44
<212> TYPE: DNA
<213> ORGANISM: Homo sapien

<400> SEQUENCE: 69
aatatagtcc cttcctggaa agaggatttt gtggcaaacc attt                   44

<210> SEQ ID NO 70
<211> LENGTH: 44
<212> TYPE: DNA
<213> ORGANISM: Homo sapien

<400> SEQUENCE: 70
aatatgatct gtacctggga acaaaacacc acctttgatc attt                   44

<210> SEQ ID NO 71
<211> LENGTH: 32
<212> TYPE: DNA
<213> ORGANISM: Homo sapien

<400> SEQUENCE: 71
ccctctcctt tagcacaggt gcagcagtga tc                                32

<210> SEQ ID NO 72
<211> LENGTH: 27
<212> TYPE: DNA
<213> ORGANISM: Homo sapien
```

```
<400> SEQUENCE: 72
ccctctcctt taggtgcagc agtgatc                                          27

<210> SEQ ID NO 73
<211> LENGTH: 32
<212> TYPE: DNA
<213> ORGANISM: Homo sapien

<400> SEQUENCE: 73
gatcactgct gcacctgtgc taaaggagag gg                                    32

<210> SEQ ID NO 74
<211> LENGTH: 27
<212> TYPE: DNA
<213> ORGANISM: Homo sapien

<400> SEQUENCE: 74
gatcactgct gcacctaaag gagaggg                                          27

<210> SEQ ID NO 75
<211> LENGTH: 60
<212> TYPE: DNA
<213> ORGANISM: Homo sapien

<400> SEQUENCE: 75
gtgggttgca tcatgggaga gctggtgaaa ggttgtgtga tattccaagg cactgaccat      60

<210> SEQ ID NO 76
<211> LENGTH: 60
<212> TYPE: DNA
<213> ORGANISM: Homo sapien

<400> SEQUENCE: 76
gtcgggtgca tcatggcaga aatggtcctc cataaagtcc tgttcccggg aagagactat      60

<210> SEQ ID NO 77
<211> LENGTH: 60
<212> TYPE: DNA
<213> ORGANISM: Homo sapien

<400> SEQUENCE: 77
atggtcagtg ccttggaata tcacacaacc tttcaccagc tctcccatga tgcaacccac      60

<210> SEQ ID NO 78
<211> LENGTH: 60
<212> TYPE: DNA
<213> ORGANISM: Homo sapien

<400> SEQUENCE: 78
atagtctctt cccgggaaca ggactttatg gaggaccatt tctgccatga tgcacccgac      60

<210> SEQ ID NO 79
<211> LENGTH: 35
<212> TYPE: DNA
<213> ORGANISM: Homo sapien

<400> SEQUENCE: 79
gatcagcctt cagcacagat gcagcagtaa gtagc                                 35

<210> SEQ ID NO 80
<211> LENGTH: 30
<212> TYPE: DNA
<213> ORGANISM: Homo sapien
```

```
<400> SEQUENCE: 80
gatcagcctt cagatgcagc agtaagtagc                                      30

<210> SEQ ID NO 81
<211> LENGTH: 35
<212> TYPE: DNA
<213> ORGANISM: Homo sapien

<400> SEQUENCE: 81
gctacttact gctgcatctg tgctgaaggc tgatc                                35

<210> SEQ ID NO 82
<211> LENGTH: 30
<212> TYPE: DNA
<213> ORGANISM: Homo sapien

<400> SEQUENCE: 82
gctacttact gctgcatctg aaggctgatc                                      30

<210> SEQ ID NO 83
<211> LENGTH: 38
<212> TYPE: DNA
<213> ORGANISM: Homo sapien

<400> SEQUENCE: 83
ggacagcctt ctccttcagc acaggtgcag cagtgaac                             38

<210> SEQ ID NO 84
<211> LENGTH: 33
<212> TYPE: DNA
<213> ORGANISM: Homo sapien

<400> SEQUENCE: 84
ggacagcctt ctccttcagg tgcagcagtg aac                                  33

<210> SEQ ID NO 85
<211> LENGTH: 38
<212> TYPE: DNA
<213> ORGANISM: Homo sapien

<400> SEQUENCE: 85
gttcactgct gcacctgtgc tgaaggagaa ggctgtcc                             38

<210> SEQ ID NO 86
<211> LENGTH: 33
<212> TYPE: DNA
<213> ORGANISM: Homo sapien

<400> SEQUENCE: 86
gttcactgct gcacctgaag gagaaggctg tcc                                  33

<210> SEQ ID NO 87
<211> LENGTH: 1418
<212> TYPE: DNA
<213> ORGANISM: Homo sapien

<400> SEQUENCE: 87
cattaattgc ttgccatcat gagcagaagc aagcgtgaca caatttttta tagtgtagag     60
attggagatt ctacattcac agtcctgaaa cgatatcaga atttaaaacc tataggctca    120
ggagctcaag gaatagtatg cgcagcttat gatgccattc ttgaaagaaa tgttgcaatc    180
aagaagctaa gccgaccatt tcagaatcag actcatgcca agcgggccta cagagagcta    240
```

```
gttcttatga aatgtgttaa tcacaaaaat ataattggcc ttttgaatgt tttcacacca      300
cagaaatccc tagaagaatt tcaagatgtt tacatagtca tggagctcat ggatgcaaat      360 cttttgccaag tgattcagat ggagctagat catgaaagaa tgtcctacct tctctatcag    420
atgctgtgtg gaatcaagca ccttcattct gctggaatta ttcatcggga cttaaagccc     480
agtaatatag tagtaaaatc tgattgcact ttgaagattc ttgacttcgg tctggccagg     540
actgcaggaa cgagttttat gatgacgcct tatgtagtga ctcgctacta cagagcaccc     600
gaggtcatcc ttggcatggg ctacaaggaa aacgtggatt tatggtctgt ggggtgcatt    660
atgggagaaa tggtttgcca caaaatcctc tttccaggaa gggactatat tgatcagtgg    720
aataaagtta ttgaacagct tggaacacca tgtcctgaat tcatgaagaa actgcaacca    780
acagtaagga cttacgttga aaacagacct aaatatgctg gatatagctt tgagaaactc   840
ttccctgatg tccttttccc agctgactca gaacacaaca aacttaaagc cagtcaggca   900
agggatttgt tatccaaaat gctggtaata gatgcatcta aaaggatctc tgtagatgaa    960
gctctccaac acccgtacat caatgtctgg tatgatcctt ctgaagcaga agctccacca   1020
ccaaagatcc ctgacaagca gttagatgaa agggaacaca aatagaaga gtggaaagaa    1080 ttgatatata aggaagttat ggacttggag gagagaacca agaatggagt tatacggggg   1140
cagccctctc ctttagcaca ggtgcagcag tgatcaatgg ctctcagcat ccatcatcat   1200
cgtcgtctgt caatgatgtg tcttcaatgt caacagatcc gactttggcc tctgatacag   1260
acagcagtct agaagcagca gctgggcctc tgggctgctg tagatgacta cttgggccat   1320
cggggggtgg gagggatggg gagtcggtta gtcattgata gaactacttt gaaaacaatt   1380
cagtggtctt attttgggt gattttcaa aaaatgta                              1418

<210> SEQ ID NO 88
<211> LENGTH: 1408
<212> TYPE: DNA
<213> ORGANISM: Rattus norvegicus

<400> SEQUENCE: 88
gcggccgagc gcgggacgtt gcggccgaaa cgcggagccg cgagcaggat taagtagcgg     60
cccggccacc ggcacggcgc cgctctccgc tactggcttc caggtctccg ttggctgcac    120
tgccggccgg ttgttgaata tttggatgaa gccattagac taattgcttg ccatcatgag    180
cagaagtaaa cgtgacaaca atttttatag tgtagagatc gcagattcta cattcacagt    240
cctaaaacga taccagaact taaagcctat aggctcagga gctcaaggaa tagtgtgtgc    300
agcttatgat gctattcttg aaagaaatgt tgcaatcaag aagctcagcc ggccatttca    360
gaatcagacc catgctaagc gagcctaccg agaactagtt cttatgaagt gtgttaatca    420
caaaaatata attggccttt tgaatgtttt cacaccacag aaatccctag aagaatttca    480
agatgtttac atagtcatgg agctcatgga tgcaaatctt tgccaagtga ttcagatgga    540
gttagatcat gaaagaatgt cctaccttct ctatcaaatg ctgtgtggaa tcaagcacct    600
tcactctgct ggaattattc atcgggactt aaagccagt aatatagtag tcaaatcaga    660
ctgcactttg aagattcttg attttggact ggcaaggact gcaggaacga gttttatgat    720
gacgccttac gtggtaactc gttactacag agcaccagag gtcattctcg gcatgggcta    780
caaggagaac gtggatttat ggtctgtggg gtgcattatg ggaaaatgg tttgcctcaa    840 aatcctcttt ccaggaaggg actatattga tcagtggaat aaagttattg aacagctcgg    900
```

| | | | | | |
|---|---|---|---|---|---|
| aacaccttgt | cctgaattca | tgaagaaact | acaaccaaca | gtaaggactt | acgttgaaaa | 960 |
| cagacctaag | tacgctggct | atagctttga | gaaactgttt | cctgatgtgc | ttttcccagc | 1020 |
| tgactcagaa | cataacaaac | ttaaagccag | tcaggcgaga | gatttgttat | ctaaaatgct | 1080 |
| ggtgatagat | gcgtccaaaa | ggatctccgt | agacgaagct | ctccagcacc | cgtacatcaa | 1140 |
| cgtctggtat | gatccttcag | aagcagaggc | cccaccacca | aagatccctg | acaagcagtt | 1200 |
| agatgaaagg | gagcacacaa | tagagagtg | gaaagaactg | atatacaagg | aggtcatgga | 1260 |
| tttggaggag | cgaactaaga | atggcgtcat | aagagggcag | ccgtctcctt | taggtgcagc | 1320 |
| agtgatcaat | ggctctcagc | atccggtctc | ttcgccgtct | gtcaatgaca | tgtcttcaat | 1380 |
| gtccacagat | ccgactctgg | cctcggat | | | 1408 |

<210> SEQ ID NO 89
<211> LENGTH: 1365
<212> TYPE: DNA
<213> ORGANISM: Homo sapien

<400> SEQUENCE: 89

| | | | | | |
|---|---|---|---|---|---|
| ttgcttgcca | tcatgagcag | aagcaagcgt | gacaacaatt | tttatagtgt | agagattgga | 60 |
| gattctacat | tcacagtcct | gaaacgatat | cagaatttaa | aacctatagg | ctcaggagct | 120 |
| caaggaatag | tatgcgcagc | ttatgatgcc | attcttgaaa | gaaatgttgc | aatcaagaag | 180 |
| ctaagccgac | catttcagaa | tcagactcat | gccaagcggg | cctacagaga | gctagttctt | 240 |
| atgaaatgtg | ttaatcacaa | aaatataatt | ggccttttga | atgttttcac | accacagaaa | 300 |
| tccctagaag | aatttcaaga | tgtttacata | gtcatggagc | tcatggatgc | aaatctttgc | 360 |
| caagtgattc | agatggagct | agatcatgaa | agaatgtcct | accttctcta | tcagatgctg | 420 |
| tgtggaatca | agcaccttca | ttctgctgga | attattcatc | gggacttaaa | gcccagtaat | 480 |
| atagtagtaa | aatctgattg | cactttgaag | attcttgact | tcggtctggc | caggactgca | 540 |
| ggaacgagtt | ttatgatgac | gccttatgta | gtgactcgct | actacagagc | acccgaggtc | 600 |
| atccttggca | tgggctacaa | ggaaaacgtg | gatttatggt | ctgtggggtg | cattatggga | 660 |
| gaaatggttt | gccacaaaat | cctctttcca | ggaagggact | atattgatca | gtggaataaa | 720 |
| gttattgaac | agcttggaac | accatgtcct | gaattcatga | agaaactgca | accaacagta | 780 |
| aggacttacg | ttgaaaacag | acctaaatat | gctggatata | gctttgagaa | actcttccct | 840 |
| gatgtccttt | tcccagctga | ctcagaacac | aacaaactta | agccagtca | ggcaagggat | 900 |
| ttgttatcca | aaatgctggt | aatagatgca | tctaaaagga | tctctgtaga | tgaagctctc | 960 |
| caacacccgt | acatcaatgt | ctggtatgat | ccttctgaag | cagaagctcc | accaccaaag | 1020 |
| atccctgaca | agcagttaga | tgaaagggaa | cacacaatag | aagagtggaa | agaattgata | 1080 |
| tataaggaag | ttatggactt | ggaggagaga | accaagaatg | gagttatacg | ggggcagccc | 1140 |
| tctcctttag | gtgcagcagt | gatcaatggc | tctcagcatc | catcatcatc | gtcgtctgtc | 1200 |
| aatgatgtgt | cttcaatgtc | aacagatccg | actttggcct | ctgatacaga | cagcagtcta | 1260 |
| gaagcagcag | ctgggcctct | gggctgctgt | agatgactac | ttgggccatc | gggggtggg | 1320 |
| agggatgggg | agtcggttag | tcattgatag | aactactttg | aaaac | | 1365 |

<210> SEQ ID NO 90
<211> LENGTH: 1311
<212> TYPE: DNA
<213> ORGANISM: Homo sapien

<400> SEQUENCE: 90

```
cattaattgc ttgccatcat gagcagaagc aagcgtgaca acaattttta tagtgtagag      60
attggagatt ctacattcac agtcctgaaa cgatatcaga atttaaaacc tataggctca     120
ggagctcaag gaatagtatg cgcagcttat gatgccattc ttgaaagaaa tgttgcaatc     180
aagaagctaa gccgaccatt tcagaatcag actcatgcca agcgggccta cagagagcta     240
gttcttatga aatgtgttaa tcacaaaaat ataattggcc ttttgaatgt tttcacacca     300
cagaaatccc tagaagaatt tcaagatgtt tacatagtca tggagctcat ggatgcaaat     360
ctttgccaag tgattcagat ggagctagat catgaaagaa tgtcctacct tctctatcag     420
atgctgtgtg aatcaagca ccttcattct gctggaatta ttcatcggga cttaaagccc     480
agtaatatag tagtaaaatc tgattgcact ttgaagattc ttgacttcgg tctggccagg     540
actgcaggaa cgagttttat gatgacgcct tatgtagtga ctcgctacta cagagcaccc     600
gaggtcatcc ttggcatggg ctacaaggaa acgttgaca tttggtcagt tgggtgcatc      660
atgggagaaa tgatcaaagg tggtgttttg ttcccaggta cagatcatat tgatcagtgg     720
aataaagtta ttgaacagct tggaacacca tgtcctgaat tcatgaagaa actgcaacca     780
acagtaagga cttacgttga aaacagacct aaatatgctg gatatagctt tgagaaactc     840
ttccctgatg tccttttccc agctgactca gaacacaaca aacttaaagc cagtcaggca     900
agggatttgt tatccaaaat gctggtaata gatgcatcta aaaggatctc tgtagatgaa     960
gctctccaac acccgtacat caatgtctgg tatgatcctt ctgaagcaga agctccacca    1020
ccaaagatcc ctgacaagca gttagatgaa agggaacaca aatagaaga gtggaaagaa    1080
ttgatatata aggaagttat ggacttggag gagagaacca agaatggagt tatacggggg    1140
cagccctctc ctttagcaca ggtgcagcag tgatcaatgg ctctcagcat ccatcatcat    1200
cgtcgtctgt caatgatgtg tcttcaatgt caacagatcc gactttggcc tctgatacag    1260
acagcagtct agaagcagca gctgggcctc tgggctgctg tagatgacta c             1311
```

<210> SEQ ID NO 91
<211> LENGTH: 1349
<212> TYPE: DNA
<213> ORGANISM: Homo sapien

<400> SEQUENCE: 91

```
attgcttgcc atcatgagca gaagcaagcg tgacaacaat ttttatagtg tagagattgg      60
agattctaca ttcacagtcc tgaaacgata tcagaattta aaacctatag gctcaggagc     120
tcaaggaata gtatgcgcag cttatgatgc cattcttgaa agaaatgttg caatcaagaa     180
gctaagccga ccatttcaga tcagactca tgccaagcgg gcctacagag agctagttct     240
tatgaaatgt gttaatcaca aaatataat tggccttttg aatgttttca ccacagaa       300
atccctagaa gaatttcaag atgtttacat agtcatggag ctcatggatg caaatctttg     360
ccaagtgatt cagatggagc tagatcatga agaatgtcc taccttctct atcagatgct     420
gtgtggaatc aagcaccttc attctgctgg aattattcat cggacttaa agcccagtaa     480
tatagtagta aatctgatt gcactttgaa gattcttgac ttcggtctgg ccaggactgc     540
aggaacgagt tttatgatga cgccttatgt agtgactcgc tactacagag cacccgaggt     600
catccttggc atgggctaca aggaaaacgt tgacatttgg tcagttgggt gcatcatggg     660
agaaatgatc aaaggtggtg ttttgttccc aggtacagat catattgatc agtggaataa     720
agttattgaa cagcttggaa caccatgtcc tgaattcatg aagaaactgc aaccaacagt     780
```

```
aaggacttac gttgaaaaca gacctaaata tgctggatat agctttgaga aactcttccc      840
tgatgtcctt ttcccagctg actcagaaca caacaaactt aaagccagtc aggcaaggga      900
tttgttatcc aaaatgctgg taatagatgc atctaaaagg atctctgtag atgaagctct      960
ccaacacccg tacatcaatg tctggtatga tccttctgaa gcagaagctc caccaccaaa     1020
gatccctgac aagcagttag atgaaaggga acacacaata gaagagtgga agaattgat      1080 atataaggaa gttatggact tggaggagag aaccaagaat ggagttatac gggggcagcc     1140
ctctccttta ggtgcagcag tgatcaatgg ctctcagcat ccatcatcat cgtcgtctgt     1200
caatgatgtg tcttcaatgt caacagatcc gactttggcc tctgatacag acagcagtct     1260
agaagcagca gctgggcctc tgggctgctg tagatgacta cttgggccat cggggggtgg     1320
gagggatggg gagtcggtta gtcattgat                                       1349

<210> SEQ ID NO 92
<211> LENGTH: 1782
<212> TYPE: DNA
<213> ORGANISM: Homo sapien

<400> SEQUENCE: 92
gggcgggcga gggatctgaa acttgcccac ccttcgggat attgcaggac gctgcatcat       60
gagcgacagt aaatgtgaca gtcagtttta tagtgtgcaa gtggcagact caaccttcac      120
tgtcctaaaa cgttaccagc agctgaaacc aattggctct ggggcccaag ggattgtttg      180
tgctgcattt gatacagttc ttgggataag tgttgcagtc aagaaactaa gccgtccttt      240
tcagaaccaa actcatgcaa agagagctta tcgtgaactt gtcctcttaa aatgtgtcaa      300
tcataaaaat ataattagtt tgttaaatgt gtttacacca caaaaaactc tagaagaatt      360
tcaagatgtg tatttggtta tggaattaat ggatgctaac ttatgtcagg ttattcacat      420
ggagctggat catgaaagaa tgtcctacct tctttaccag atgctttgtg gtattaaaca      480
tctgcattca gctggtataa ttcatagaga tttgaagcct agcaacattg ttgtgaaatc      540
agactgcacc ctgaagatcc ttgactttgg cctggcccgg acagcgtgca ctaacttcat      600
gatgacccct tacgtggtga cacggtacta ccgggcgccc gaagtcatcc tgggtatggg      660
ctacaaagag aacgttgata tctggtcagt gggttgcatc atgggagagc tggtgaaagg      720
ttgtgtgata ttccaaggca ctgaccatat tgatcagtgg aataaagtta ttgagcagct      780
gggaacacca tcagcagagt tcatgaagaa acttcagcca actgtgagga attatgtcga      840
aaacagacca aagtatcctg gaatcaaatt tgaagaactc tttccagatt ggatattccc      900
atcagaatct gagcgagaca aaataaaaac aagtcaagcc agagatctgt tatcaaaaat      960
gttagtgatt gatcctgaca gcggatctct gtagacgaa gctctgcgtc acccatacat      1020
cactgtttgg tatgacccccg ccgaagcaga agccccacca cctcaaattt atgatgccca     1080 gttgaagaa agagaacatg caattgaaga atggaaagag ctaatttaca aagaagtcat      1140
ggattgggaa gaaagaagca agaatggtgt tgtaaaagat cagccttcag atgcagcagt      1200
aagtagcaac gccactcctt ctcagtcttc atcgatcaat gacatttcat ccatgtccac      1260
tgagcagacg ctggcctcag acacagacag cagtcttgat gcctcgacgg gacccttga      1320 aggctgtcga tgataggtta gaaatagcaa acctgtcagc attgaaggaa ctctcacctc      1380
cgtgggcctg aaatgcttgg gagttgatgg aaccaaatag aaaaactcca tgttctgcat      1440
gtaagaaaca caatgccttg ccctattcag acctgatagg attgcctgct tagatgataa      1500
aatgaggcag aatatgtctg aagaaaaaaa ttgcaagcca cacttctaga gatttttgttc     1560
```

-continued

| | |
|---|---|
| aagatcattt caggtgagca gttagagtag gtgaatttgt ttcaaattgt actagtgaca | 1620 |
| gtttctcatc atctgtaact gttgagatgt atgtgcatgt gaccacaaat gcttgcttgg | 1680 |
| acttgcccat ctagcacttt ggaaatcagt atttaaatgc caaataatct tccaggtagt | 1740 |
| gctgcttctg aagttatctc ttaatcctct taagtaattt gg | 1782 |

<210> SEQ ID NO 93
<211> LENGTH: 2622
<212> TYPE: DNA
<213> ORGANISM: Rattus norvegicus

<400> SEQUENCE: 93

| | |
|---|---|
| tgtatgacac tacatcatga gtgacagtaa aagcgatggc cagttttaca gtgtgcaagt | 60 |
| ggcagactca actttcactg ttctaaaacg ttaccagcag ttgaaaccaa ttggctctgg | 120 |
| agcccaagga attgtttgtg ctgcttttga tacagttctt ggaataaatg ttgctgtcaa | 180 |
| gaagttaagt cgtccttttc agaaccaaac gcatgcaaag agagcctacc gtgaacttgt | 240 |
| cctcctaaag tgtgtcaatc ataaaaatat aattagcttg ttaaatgtgt tcacaccaca | 300 |
| aaaaacgcta aagaattcc aagatgtgta cttggttatg gagttaatgg acgctaactt | 360 |
| atgtcaggtt attcatatgg agctggacca tgaaagaatg tcatacctcc tctaccagat | 420 |
| gctttgtggc attaagcacc tgcattcagc tggcataatt cataggggatt tgaagcctag | 480 |
| caacattgta gtaaaatcag actgtactct caagatcctt gactttggcc tggcacggac | 540 |
| agcctgtacc aactttatga tgactcccta tgtggtaact cgctactatc gggctccaga | 600 |
| agtcatcctg ggcatgggct acaaggagaa tgttgatatc tggtcagtgg gttgcatcat | 660 |
| gggagagctg gtgaaaggtt gtgtgatatt ccaaggtact gaccatattg atcaatggaa | 720 |
| taaagttatt gaacagctag gaacaccatc cgcagagttc atgaagaaac ttcagccaac | 780 |
| tgtaaggaat tatgtggaaa acagaccaaa gtaccctgga atcaaatttg aagagctctt | 840 |
| tccagattgg atatttccgt cagaatccga acgagacaaa ataaaaacaa gtcaagccag | 900 |
| agatctgtta tcgaaaatgt tagtgattga tccggacaag cggatctctg tggacgaagc | 960 |
| cttgcgccac ccgtatatta ctgtttggta tgaccccgct gaagcagaag cgccaccacc | 1020 |
| tcaaatttat gatgcccagt tggaagaaag agagcatgcg attgaagagt ggaaagaact | 1080 |
| aatttacaaa gaagtgatgg actgggaaga agaagcaag aatggggtga agaccagcc | 1140 |
| ttcagatgca gcagtaagca gcaaggctac tccttctcag tcgtcatcca tcaatgacat | 1200 |
| ctcatccatg tccactgagc acaccctggc ctcagacaca gacagcagtc tcgatgcctc | 1260 |
| aaccggaccc ctggaaggct gccgatgaaa cctcgcagat ggcgcacttg tctgtgaagg | 1320 |
| actctggctt ccatggccct gagcacatgg gagctggtgg aacaaatcaa gaagctccat | 1380 |
| gttctgcatg taagaaacac gacgccttgc ccccactcag ttccagtagg attgcctgcg | 1440 |
| tagactgtaa catgaggcag acgatgtctg gagaaaaagt acaaaccaca ctgttagaaa | 1500 |
| ttttgttcaa gatcattcag gtgagcaatt agaatagccg agttcttttc aagtcgtgtg | 1560 |
| gtgtccttgg tgacagatca tgtgtaactg tggggactcg tatgcatgtg accacaaatg | 1620 |
| cttgcttgaa cttgcccatg tagcactttg ggaatcagta tttaaatgcc aaataatctt | 1680 |
| ccaggtagtt ctgcttctag aataatctct taatcctctt tagtaatttg gtgtctgtcc | 1740 |
| acaaaaaaat agattatgtg tgtatgaatt ggccactatc atattatcat attttaccca | 1800 |
| ctttttatggt atgattttatt ctgtcttttg tatttcagaa ggaatataat taaatttatt | 1860 |
| taataaaataa aactacagct tttcttaaat ttgtgatgtt ttaggctgag aattaccact | 1920 |

```
gctttatatc gacactctgt gtcctttaaa ctgcccacta tgggaaactt tacgtacagc    1980
tttctgcatg acaaagttcc aagttgtatt tcactctgct taacgactta tgtcaccttg    2040
aatcctgacc acacatttcc ttttcttgg tcctctgaac ttggatctag aatccctcac     2100
agaacttcac cttctttatc acaaagcacc ccatctcagt agaatgaatc ggcagattcc    2160
tgagccccgc tgcctaatgt agagctgaca gggtggcttc cccagaacgg tgggtgggtg    2220
catccttccc tgagcccacc catcctttgc tcccctctct ttatttaagg tgaaaggtga    2280
ttgggtctca tagcctttcc ttttgtagca ttgcctaact tgtctttctc actgacagaa    2340
gccaccacgt ccagccagag cacatggtct cttaggagac cgggcttact taccatgcat    2400
gtttgctgct gtccttttcc attttgtgga ggcatttcct ttttctaagg gaattcctca    2460
gatgttctag aaacattcag aagaacgcag aagaaatatt ctagagaatt gggggttcat    2520
tcttgaatat tttctgattt aaaactgctc acctgaaatt gatactttca gatcctgatc    2580
ttgtaaatta ctcgagattt ggtaagatgc tgagttctct gt                       2622

<210> SEQ ID NO 94
<211> LENGTH: 1873
<212> TYPE: DNA
<213> ORGANISM: Homo sapien

<400> SEQUENCE: 94
caaactacgt gctgtacagc tgcatcagct gctcgtagac atgtccagca gctggtcgag      60
gtccacgccg cggtaggtga agttgcggaa ggtccggcga gggatctgaa acttgcccct     120 taccttcgg gatattgcag gacgctgcat catgagcgac agtaaatgtg acagtcagtt      180
ttatagtgtc caagtggcag actcaacctt cactgtccta aaacgttacc agcagctgaa     240
accaattggc tctggggccc aagggattgt tgtgctgca tttgatacag ttcttgggat      300
aaatgttgca gtcaagaaac taagccgtcc ttttcagaac caaactcatg caaagagagc     360
ttatcgtgaa cttgtcctct aaaatgtgt caatcataaa aatataatta gtttgttaaa      420
tgtgtttaca ccacaaaaaa ctctagaaga atttcaagat gtgtatttgg ttatggaatt     480
aatggatgct aacttatgtc aggttattca catggagctg gatcatgaaa gaatgtccta    540
ccttctttac cagatgcttt gtggtattaa acatctgcat tcagctggta taattcatag    600
agatttgaag cctagcaaca ttgttgtgaa atcagactgc accctgaaga tccttgactt    660
tggcctggcc cggacagcgt gcactaactt catgatgacc ccttacgtgg tgacacggta    720
ctaccgggcg cccgaagtca tcctgggtat gggctacaaa gagaacgttg atatctggtc    780
agtgggttgc atcatgggag agctggtgaa aggttgtgtg atattccaag gcactgacca    840
tattgatcag tggaataaag ttattgagca gctgggaaca ccatcagcag agttcatgaa    900
gaaacttcag ccaactgtga ggaattatgt cgaaaacaga ccaaagtatc ctggaatcaa    960
atttgaagaa ctcttccag attggatatt cccatcagaa tctgagcgag acaaaataaa     1020
aacaagtcaa gccagagatc tgttatcaaa atgttagtg attgatcctg acaagcggat    1080
ctctgtagac gaagctctgc gtcacccata catcactgtt tggtatgacc ccgccgaagc    1140
agaagcccca cccctcaaa tttatgatgc ccagttggaa gaaagagaac atgcaattga    1200
agaatggaaa gagctaattt acaaagaagt catggattgg gaagaaagaa gcaagaatgg    1260
tgttgtaaaa gatcagcctc cagatgcagc agtaagtagc aacgccactc cttctcagtc    1320
ttcatcgatc aatgacattt catccatgtc cactgagcag acgctggcct cagacacaga    1380
cagcagtctt gatgcctcga cgggaccct tgaaggctgt cgatgatagg ttagaaatag     1440
```

| | |
|---|---|
| caaacctgtc agcattgaag gaactctcac ctccgtgggc ctgaaatgct tgggagttga | 1500 |
| tggaaccaaa tagaaaaact ccatgttctg catgtaagaa acacaatgcc ttgccctact | 1560 |
| cagacctgat aggattgcct gcttagatga taaaatgagg cagaatatgt ctgaagaaaa | 1620 |
| aaattgcaag ccacacttct agagattttg ttcaagatca tttcagttga gcagttagag | 1680 |
| taggtgaatt tgtcaaattg tactagtgac agtttctcat catctgtaac tgttgagatg | 1740 |
| attgtgcatg tgaccacaaa tgcttgcttg gacttgccca tctagcactt tggaaatcag | 1800 |
| tatttaaatg ccaaataatc ttccaggtag tgctgcttct gaagttatct cttaatcctc | 1860 |
| ttaagtaatt tgg | 1873 |

<210> SEQ ID NO 95
<211> LENGTH: 1392
<212> TYPE: DNA
<213> ORGANISM: Homo sapien

<400> SEQUENCE: 95

| | |
|---|---|
| tctgaaactt gcccacccett cgggatattg caggacgctg catcatgagc gacagtaaat | 60 |
| gtgacagtca gttttatagt gtgcaagtgg cagactcaac cttcactgtc ctaaaacgtt | 120 |
| accagcagct gaaaccaatt ggctctgggg cccaagggat tgtttgtgct gcatttgata | 180 |
| cagttcttgg gataagtgtt gcagtcaaga aactaagccg tccttttcag aaccaaactc | 240 |
| atgcaaagag agcttatcgt gaacttgtcc tcttaaaatg tgtcaatcat aaaaatataa | 300 |
| ttagtttgtt aaatgtgttt acaccacaaa aaactctaga agaatttcaa gatgtgtatt | 360 |
| tggttatgga attaatggat gctaacttat gtcaggttat tcacatggag ctggatcatg | 420 |
| aaagaatgtc ctaccttctt taccagatgc tttgtggtat taaacatctg cattcagctg | 480 |
| gtataattca tagagatttg aagcctagca acattgttgt gaaatcagac tgcacccctga | 540 |
| agatccttga ctttggcctg gcccggacag cgtgcactaa cttcatgatg accccttacg | 600 |
| tggtgacacg gtactaccgg gcgcccgaag tcatcctggg tatgggctac aaagagaacg | 660 |
| ttgatatctg gtcagtgggt tgcatcatgg gagagctggt gaaaggttgt gtgatattcc | 720 |
| aaggcactga ccatattgat cagtggaata aagttattga gcagctggga acaccatcag | 780 |
| cagagttcat gaagaaactt cagccaactg tgaggaatta tgtcgaaaac agaccaaagt | 840 |
| atcctggaat caaatttgaa gaactctttc cagattggat attcccatca gaatctgagc | 900 |
| gagacaaaat aaaaacaagt caagccagag atctgttatc aaaaatgtta gtgattgatc | 960 |
| ctgacaagcg gatctctgta gacgaagctc tgcgtcaccc atacatcact gtttggtatg | 1020 |
| accccgccga agcagaagcc ccaccacctc aaatttatga tgcccagttg gaagaaagag | 1080 |
| aacatgcaat tgaagaatgg aaagagctaa tttacaaaga agtcatggat tgggaagaaa | 1140 |
| gaagcaagaa tggtgttgta aaagatcagc cttcagcaca gatgcagcag taagtagcaa | 1200 |
| cgccactcct tctcagtctt catcgatcaa tgacatttca tccatgtcca ctgagcagac | 1260 |
| gctggcctca gacacagaca gcagtcttga tgcctcgacg ggacccccttg aaggctgtcg | 1320 |
| atgataggtt agaaatagca aacctgtcag cattgaagga actctcacct ccgtgggcct | 1380 |
| gaaatgcttg gg | 1392 |

<210> SEQ ID NO 96
<211> LENGTH: 1523
<212> TYPE: DNA
<213> ORGANISM: Homo sapien

<400> SEQUENCE: 96

```
ggatattgca ggacgctgca tcatgagcga cagtaaatgt gacagtcagt tttatagtgt      60
gcaagtggca gactcaacct tcactgtcct aaaacgttac cagcagctga aaccaattgg     120
ctctggggcc caagggattg tttgtgctgc atttgataca gttcttggga taagtgttgc     180
agtcaagaaa ctaagccgtc cttttcagaa ccaaactcat gcaaagagag cttatcgtga     240
acttgtcctc ttaaaatgtg tcaatcataa aaatataatt agtttgttaa atgtgtttac     300
accacaaaaa actctagaag aatttcaaga tgtgtatttg gttatggaat taatggatgc     360
taacttatgt caggttattc acatggagct ggatcatgaa agaatgtcct accttcttta     420
ccagatgctt tgtggtatta aacatctgca ttcagctggt ataattcata gagatttgaa     480
gcctagcaac attgttgtga atcagactgc accctgaag atccttgact ttggcctggc      540
ccggacagcg tgcactaact tcatgatgac cccttacgtg gtgacacggt actaccgggc     600
gcccgaagtc atcctgggta tgggctacaa agagaacgtt gatatctggt cagtcgggtg     660
catcatggca gaaatggtcc tccataaagt cctgttcccg ggaagagact atattgatca     720
gtggaataaa gttattgagc agctgggaac accatcagca gagttcatga agaaacttca     780
gccaactgtg aggaattatg tcgaaaacag accaaagtat cctggaatca aatttgaaga     840
actctttcca gattggatat tcccatcaga atctgagcga gacaaaataa aaacaagtca     900
agccagagat ctgttatcaa aaatgttagt gattgatcct gacaagcgga tctctgtaga     960
cgaagctctg cgtcacccat acatcactgt ttggtatgac cccgccgaag cagaagcccc    1020
accacctcaa atttatgatg cccagttgga agaaagagaa catgcaattg aagaatggaa    1080
agagctaatt tacaaagaag tcatggattg ggaagaaaga agcaagaatg gtgttgtaaa    1140
agatcagcct tcagcacaga tgcagcagta agtagcaacg ccactccttc tcagtcttca    1200
tcgatcaatg acatttcatc catgtccact gagcagacgc tggcctcaga cacagacagc    1260
agtcttgatg cctcgacggg acccttgaa ggctgtcgat gataggttag aaatagcaaa     1320
cctgtcagca ttgaaggaac tctcacctcc gtgggcctga aatgcttggg agttgatgga    1380
accaaataga aaaactccat gttctgcatg taagaaacac aatgccttgc cctattcaga    1440
cctgatagga ttgcctgctt agatgataaa atgaggcaga atatgtctga agaaaaaaat    1500
tgcaagccac acttctagag att                                             1523
```

<210> SEQ ID NO 97
<211> LENGTH: 1619
<212> TYPE: DNA
<213> ORGANISM: Homo sapien

<400> SEQUENCE: 97

```
gcccacccctt cgggatattg caggacgctg catcatgagc gacagtaaat gtgacagtca      60
gttttatagt gtgcaagtgg cagactcaac cttcactgtc ctaaaacgtt accagcagct     120
gaaaccaatt ggctctgggg cccaagggat tgtttgtgct gcatttgata cagttcttgg     180
gataagtgtt gcagtcaaga aactaagccg tccttttcag aaccaaactc atgcaaagag     240
agcttatcgt gaacttgtcc tcttaaaatg tgtcaatcat aaaaatataa ttagtttgtt     300
aaatgtgttt acaccacaaa aactctaga agaatttcaa gatgtgtatt tggttatgga      360
attaatggat gctaacttat gtcaggttat tcacatggag ctggatcatg aaagaatgtc     420
ctaccttctt taccagatgc tttgtggtat taaacatctg cattcagctg gtataattca     480
tagagatttg aagcctagca acattgttgt gaaatcagac tgcaccctga gatccttga     540
```

```
ctttggcctg gcccggacag cgtgcactaa cttcatgatg acccCttacg tggtgacacg      600
gtactaccgg gcgcccgaag tcatcctggg tatgggctac aaagagaacg ttgatatctg      660
gtcagtcggg tgcatcatgg cagaaatggt cctccataaa gtcctgttcc cgggaagaga      720
ctatattgat cagtggaata agttattga gcagctggga acaccatcag cagagttcat       780
gaagaaactt cagccaactg tgaggaatta tgtcgaaaac agaccaaagt atcctggaat      840
caaatttgaa gaactctttc cagattggat attcccatca gaatctgagc gagacaaaat      900
aaaaacaagt caagccagag atctgttatc aaaaatgtta gtgattgatc ctgacaagcg      960
gatctctgta gacgaagctc tgcgtcaccc atacatcact gtttggtatg accccgccga     1020
agcagaagcc ccaccacctc aaatttatga tgcccagttg gaagaaagag aacatgcaat     1080
tgaagaatgg aaagagctaa tttacaaaga gatcatggat tgggaagaaa gaagcaagaa     1140
tggtgttgta aaagatcagc cttcagatgc agcagtaagt agcaacgcca ctccttctca     1200
gtcttcatcg atcaatgaca tttcatccat gtccactgag cagacgctgg cctcagacac     1260
agacagcagt cttgatgcct cgacgggacc ccttgaaggc tgtcgatgat aggttagaaa     1320
tagcaaacct gtcagcattg aaggaactct cacctccgtg ggcctgaaat gcttgggagt     1380
tgatggaacc aaatagaaaa actccatgtt ctgcatgtaa gaaacacaat gccttgccct     1440
attcagacct gataggattg cctgcttaga tgataaaatg aggcagaata tgtctgaaga     1500
aaaaaattgc aagccacact tctagagatt ttgttcaaga tcatttcagg tgagcagtta     1560
gagtaggtga atttgtttca aattgtacta gtgacagttt ctcatcatct gtaactgtt      1619

<210> SEQ ID NO 98
<211> LENGTH: 2372
<212> TYPE: DNA
<213> ORGANISM: Homo sapien

<400> SEQUENCE: 98
gagaaatggc gtggcagggg acccagcgag cccagaggga ttttgccgct gcttcctcta       60
cccctgtatt tcacgcagct ctctaaattg actcagctcc aggctagtgt gagaaacacc      120
aacagcaggc ccatctcaga tcttcactat ggcaacttat gcaagaaact gttgaattag      180
acccgtttcc tatagatgag aaaccataca agctgtggta tttatgagcc tccatttctt      240
atactactgc agtgaaccaa cattggatgt gaaaattgcc ttttgtcagg gattcgataa      300
acaagtggat gtgtcatata ttgccaaaca ttacaacatg agcaaaagca agttgacaa       360 ccagttctac agtgtggaag tgggagactc aaccttcaca gttctcaagc gctaccagaa      420
tctaaagcct attggctctg gggctcaggg catagtttgt gccgcgtatg atgctgtcct      480
tgacagaaat gtggccatta agaagctcag cagaccctTt cagaaccaaa cacatgccaa      540
gagagcgtac cgggagctgg tcctcatgaa gtgtgtgaac cataaaaaca ttattagttt      600
attaaatgtc ttcacacccc agaaaacgct ggaggagttc caagatgttt acttagtaat      660
ggaactgatg gatgccaact tatgtcaagt gattcagatg gaattagacc atgagcgaat      720
gtcttacctg ctgtaccaaa tgttgtgtgg cattaagcac ctccattctg ctggaattat      780
tcacagggat ttaaaaccaa gtaacattgt agtcaagtct gattgcacat gaaaatcct       840 ggactttgga ctgccagga cagcaggcac aagcttcatg atgactccat atgtggtgac       900
acgttattac agagcccctg aggtcatcct ggggatgggc tacaaggaga cgtggatat       960 atggtctgtg gatgcatta tgggagaaat ggttcgccac aaaatcctct ttccaggaag     1020
ggactatatt gaccagtgga ataaggtaat tgaacaacta ggaacaccat gtccagaatt     1080
```

```
catgaagaaa ttgcaaccca cagtaagaaa ctatgtggag aatcggccca agtatgcggg   1140
actcaccttc cccaaactct tcccagattc cctcttccca gcggactccg agcacaataa   1200
actcaaagcc agccaagcca gggacttgtt gtcaaagatg ctagtgattg acccagcaaa   1260
aagaatatca gtggacgacg ccttacagca tccctacatc aacgtctggt atgacccagc   1320
cgaagtggag gcgcctccac ctcagatata tgacaagcag ttggatgaaa gagaacacac   1380
aattgaagaa tggaaagaac ttatctacaa ggaagtaatg aattcagaag aaaagactaa   1440
aaatggtgta gtaaaaggac agccttctcc ttcagcacag gtgcagcagt gaacagcagt   1500
gagagtctcc ctccatcctc gtctgtcaat gacatctcct ccatgtccac cgaccagacc   1560
ctggcatctg acactgacag cagcctggaa gcctcggcag gacccctggg ttgttgcagg   1620
tgactagccg cctgcctgcg aaacccagcg ttcttcagga gatgatgtga tggaacacac   1680
acacacgcag acacacacac acacacaaat gcagacacac aacatcaaga aaacagcaag   1740
ggagagaatc caagcctaaa attaaataaa tctttcagcc tgcttcttcc ccagggttct   1800
gtattgcagc taagctcaaa tgtatattta acttctagtt gctcttgctt tggtcttctt   1860
ccaatgatgc ttactacaga aagcaaatca gacacaatta gagaagccct ttccataaag   1920
tgtaatttta atggctgcaa aaccggcaac ctgtaactgc cctttttaaat ggcatgacaa   1980 ggtgtgcagt ggccccatcc agcatgtgtg tgtctctatc ttgcatctac ctgctccttg   2040
gcctagtcag atggatgtag atacagatcc gcatgtgtct gtattcatac agcactactt   2100
acttagagat gctactctca gtgtcctcag ggctctacca agacaataatg cactggggta   2160 ccacatggtc catttcatgt gatctattac tctgacataa acccatctgt aatatattgc   2220
cagtatataa gctgtttagt ttgttaattg attaaactgt atgtcttata agaaaacatg   2280 taaagggga atatattggg ggagtgagct ctctcagacc cttgaagatg tagcttccaa   2340
atttgaatgg attaaatggc acctgtatac ca                                 2372

<210> SEQ ID NO 99
<211> LENGTH: 1975
<212> TYPE: DNA
<213> ORGANISM: Rattus norvegicus

<400> SEQUENCE: 99
ccctccttat tccggtttgg aatgtggcta atgaaagccc agtaggagga tttctggggc     60
aaacaggtgg accaggatcc tggttctcag gcacggaatg gctattgtga gagcgccacc    120
agcaggacca tcgcagatct tggttatggc tgctcacgca agaggctgtt gatgtagacc    180 cccttcccg tagatgagaa atcacacgag cagtggtatt tatgagcctc catttcttat     240
actactgcag tgaaccaacc ttggatgtga aaattgcctt ttgtcaggtg tgtgttcctt    300
acaggtaaaa caagggatt cgacaaacac gtggatgtgt cttctgttgt caaacattac     360
aacatgagca aaagcaaggt agataaccag ttctacagtg tggaagtggg agactcaacc    420
ttcacagttc taaagcgcta ccagaacctg aagccgatcg gctctgggc tcagggaata     480 gtttgtgctg cgtatgacgc tgtcctcgac agaaatgtgg ccattaagaa gctcagcaga    540
cccttccaga accaaactca tgccaagagg gcttaccggg agctggtcct catgaagtgt    600
gtgaaccata aaacattat tagcttatta aatgtcttta caccccagaa acactggag     660 gagttccaag atgttttact tagtgatgaa ctgatggacg ccaacttgtg tcaggtgatt    720
cagatggagc tggaccacga gcggatgtcg tacttgctgt accagatgct gtcggcgatc    780
aaacacctcc actccgctgg gatcatccac agggacttaa aacccagtaa catcgtagtc    840
```

-continued

```
aagtctgatt gcacactgaa atcctggac tttggactgg ccaggacagc gggcacaagc    900
ttcatgatga ctccgtatgt ggtgacgaga tattacagag cccccgaggt catcctgggc    960
atgggctaca aggagaacgt ggacatatgg tctgtgggct gcatcatggg agaaatggtt   1020
cgtcacaaaa tcctctttcc cggaagggac tatattgacc agtggaacaa agtcatagag   1080
cagctaggaa ctccgtgtcc agaattcatg aagaaattgc agcccaccgt cagaaactac   1140
gtggagaacc ggcccaagta tgcaggcctc accttcccca agctctttcc agattccctc   1200
ttcccagcgg attccgagca caataaactt aaagccagcc aagccaggga cttgttgtca   1260
aagatgttag tgattgaccc agcgaagagg atatcggtgg atgacgcatt gcagcatccg   1320
tacatcaacg tttggtacga ccctgctgaa gtggaggcgc ctccgcctca gatatatgac   1380
aagcaattgg atgaaaggga gcacaccatc gaagaatgga agaactcat ctacaaggaa    1440
gtaatgaact cagaagagaa gactaagaac ggcgtagtca aaggccagcc ctcaccttca   1500
ggtgcagcag tgaacagcag tgagagtctc cctccatcct catctgtcaa cgacatctcc   1560
tccatgtcca ccgaccagac cctcgcatcc gacactgaca gcagcctgga agcctcggcg   1620
ggaccgctgg gttgttgcag gtgactagcc gcctgcctgc gaaacccagc gttcttcagg   1680
agatgacgcc atgatagaac acagcgcaca tgcacacaca cagagcttgt acacacacac   1740
acacacacac acacacgcac gcacgcacgc acgcaagcac gcacgcacgc acaaatgcac   1800
tcacgcaatg tcaagaaaaa aaaagtagc gagagagagc gagagagcca acgtaaaact    1860
aagttaaatc tttctgcgtg cttctccaga gttctgtatc gcagctgagc tgaaatgtat   1920
acttaacttc tagtcgcgct cgctcgactt tggtctcct ccggcagtgc ttact          1975
```

<210> SEQ ID NO 100
<211> LENGTH: 2522
<212> TYPE: DNA
<213> ORGANISM: Mus musculus

<400> SEQUENCE: 100

```
ggggcttgag tgagctaaag attgggtctt cttggaaatc acctgtctgt tattattttt     60
aaacaatcgc tacacctcca aagactctgc tccttactcc ggtttggaat gtggctaatg    120
actacccagt agggaggatt tctggggcaa acagccggac caggatccta gttctcaggc    180
acggaatggc tattgtgaga acagcaccag caggatcatc gcagatcttg ttatggcca     240
ctcaggcaag acgctgttga gttaagaccc cttcccata gatgagaagc cacagaagca     300
gtggtattta tgagcctcca tttcttatac tactgcagtg aaccaacctt ggatgtgaaa    360
attgcctttt gtcagggatt cgataaacac gtggatgtgt catctattgc caaacattac    420
aacatgagca aaagcaaggt ggacaaccag ttctacagtg tggaagtggg ggactcaacc    480
ttcaccgttc ttaagcgcta ccagaacctg aagccaattg gctctggggc tcagggaata    540
gtctgtgctg cgtacgacgc tgtccttgac agaaatgtgg ccattaagaa gctcagcaga    600
cccttccaga accaaactca cgccaagagg gcttaccggg agctggtgct catgaagtgt    660
gtgaaccata aaacattat agcttatta aatgttttta cacccagaa aacgctggag       720
gagttccaag atgtctactt agtgatgaa ctgatggacg ccaacctgtg tcaggtgatt     780
cagatggagc tggaccacga gcggatgtct tacttgctgt accagatgct gtgtggcatc    840
aagcacctcc actccgctgg gatcatccac agggacttaa aacccagtaa cattgtagtc    900
aagtctgatt gcacactgaa aatcctggac ttcggactgg ccaggacagc gggtacaagc    960
ttcatgatga ctccgtatgt ggtgacgcga tattacagag cccctgaggt catcctgggc   1020
```

| | |
|---|---:|
| atgggctaca aggagaacgt ggacatatgg tctgtgggat gcatcatggg agaaatggtt | 1080 |
| cgccacaaaa tcctctttcc cggaaggagc tatattgacc agtggaacaa agtcatcgag | 1140 |
| cagctaggaa ctccgtgtcc agagttcatg aagaaattgc agcccacagt cagaaactac | 1200 |
| gtggagaatc ggcccaagta cgcaggactc accttcccca agctctttcc agattccctc | 1260 |
| ttcccagcgg attctgagca caataaactt aaagccagcc aagccaggga tttgttgtct | 1320 |
| aagatgttag tgattgaccc agtgaagagg atatcggtgg acgacgcact gcagcatccg | 1380 |
| tacatcaacg tttggtacga cccggctgaa gtggaggcgc tccgcctca gatatatgat | 1440 |
| aagcagctgg atgaaaggga gcacaccatc gaagaatgga agaacttat ctacaaggag | 1500 |
| gtaatgaact cagaagagaa gactaagaat ggcgtagtca aaagccagcc ctcgccttca | 1560 |
| gcacaggtgc agcagtgaac agcagtgaga gtctccctcc atcctcggct gtcaacgaca | 1620 |
| tctcctccat gtccaccgac cagaccctcg catctgacac tgacagcagc ctggaggcct | 1680 |
| cggcgggacc gttgggttgt tgcaggtgac tagccgcctg cctgcgaaac ccagcgttct | 1740 |
| tcaggagatg acgcgataga acacagcaca catgcacaca cacagcttgc tctcacacac | 1800 |
| actcagcttg ctcacacaca cacacacaca tacacacaaa cacacactgt ctctctctca | 1860 |
| cacacacaca ctgtcacaac gcactcacga aaggtcaaga aaaaaataac aatagagaga | 1920 |
| tccaacataa aattaagtta aattttctg cgtgcttctc caaagttctg tatcacagct | 1980 |
| gagctgaaat gtatacttaa cttctagttg cgctcgcttt ggtttccctc cagcagtgct | 2040 |
| tactacacaa gacaaatcag acacaattag agaaaccttt ccctaaagtg taacttaagt | 2100 |
| ggctgcagaa ccagcaacct gtaactgccc ttcaaatggc atgaggaggt gggcacgggt | 2160 |
| cccgcccagc atgtgtgtgt ctctatctcg cgtctacctg ctcttccggc ctagtcagat | 2220 |
| ggatgtagat acagatcccg catgtgtctg tattcaaaca gcacttagag atgctcctgt | 2280 |
| cagtgtcctc caggctccac caagacacac accggggtac cacatggtcc atttcatgtg | 2340 |
| atctattact ctgacataaa tccatctgta atatattgcc agtatataag ctgtttagtt | 2400 |
| tgttaattgc ttaagctgta tgtcttataa gagactatgt aaaggggaa atggaggcg | 2460 |
| tgaactctca gacccttgaa gatgtagctt ccgaatttga ccgttaaatg gcaccgtata | 2520 |
| cc | 2522 |

<210> SEQ ID NO 101
<211> LENGTH: 1773
<212> TYPE: DNA
<213> ORGANISM: Homo sapien

<400> SEQUENCE: 101

| | |
|---|---:|
| atctcagatc ttcactatgg caacttatgc aagaaactgt tgaattagac ccgtttccta | 60 |
| tagatgagaa accatacaag ctgtggtatt tatgagcctc catttcttat actactgcag | 120 |
| tgaaccaaca ttggatgtga aaattgcctt ttgtcaggga ttcgataaac aagtggatgt | 180 |
| gtcatatatt gccaaacatt acaacatgag caaaagcaaa gttgacaacc agttctacag | 240 |
| tgtggaagtg ggagactcaa ccttcacagt tctcaagcgc taccagaatc taaagcctat | 300 |
| tggctctggg gctcagggca tagtttgtgc cgcgtatgat gctgtccttg acagaaatgt | 360 |
| ggccattaag aagctcagca gacccttca gaaccaaaca catgccaaga gagcgtaccg | 420 |
| ggagctggtc ctcatgaagt gtgtgaacca taaaaacatt attagtttat taaatgtctt | 480 |
| cacaccccag aaaacgctgg aggagttcca agatgtttac ttagtaatgg aactgatgga | 540 |
| tgccaactta tgtcaagtga ttcagatgga attagaccat gagcgaatgt cttacctgct | 600 |

```
gtaccaaatg ttgtgtggca ttaagcacct ccattctgct ggaattattc acagggattt    660
aaaaccaagt aacattgtag tcaagtctga ttgcacattg aaaatcctgg actttggact    720
ggccaggaca gcaggcacaa gcttcatgat gactccatat gtggtgacac gttattacag    780 agccctgag gtcatcctgg ggatgggcta caaggagaac gtggatatat ggtctgtggg    840
atgcattatg ggagaaatgg ttcgccacaa atcctctttt ccaggaaggg actatattga    900
ccagtggaat aaggtaattg aacaactagg aacaccatgt ccagaattca tgaagaaatt    960
gcaacccaca gtaagaaact atgtggagaa tcggcccaag tatgcgggac tcaccttccc   1020
caaactcttc ccagattccc tcttcccagc ggactccgag cacaataaac tcaaagccag   1080
ccaagccagg gacttgttgt caaagatgct agtgattgac ccagcaaaaa gaatatcagt   1140
ggacgacgcc ttacagcatc cctacatcaa cgtctggtat gacccagccg aagtggaggc   1200
gcctccacct cagatatatg acaagcagtt ggatgaaaga gaacacacaa ttgaagaatg   1260
gaaagaactt atctacaagg aagtaatgaa ttcagaagaa aagactaaaa atggtgtagt   1320
aaaaggacag ccttctcctt cagcacaggt gcagcagtga acagcagtga gagtctccct   1380
ccatcctcgt ctgtcaatga catctcctcc atgtccaccg accagaccct ggcatctgac   1440
actgacagca gcctggaagc tcggcagga cccctgggtt gttgcaggtg actagccgcc   1500
tgcctgcgaa acccagcgtt cttcaggaga tgatgtgatg gaacacacac acacgcagac   1560
acacacacac acacaaatgc agacacacaa catcaagaaa acagcaaggg agagaatcca   1620
agcctaaaat taaataaatc tttcagcctg cttcttcccc agggttctgt attgcagcta   1680
agctcaaatg tatatttaac ttctagttgc tcttgctttg gtcttcttcc aatgatgctt   1740
actacagaaa gcaaatcaga cacaattaga gaa                                 1773
```

<210> SEQ ID NO 102
<211> LENGTH: 1505
<212> TYPE: DNA
<213> ORGANISM: Homo sapien

<400> SEQUENCE: 102

```
ttatgcaaga aactgttgaa ttagacccgt ttcctataga tgagaaacca tacaagctgt     60
ggtatttatg agcctccatt tcttatacta ctgcagtgaa ccaacattgg atgtgaaaat    120
tgccttttgt cagggattcg ataaacaagt ggatgtgtca tatattgcca aacattacaa    180
catgagcaaa agcaaagttg acaaccagtt ctacagtgtg gaagtgggag actcaacctt    240
cacagttctc aagcgctacc agaatctaaa gcctattggc tctggggctc agggcatagt    300
ttgtgccgcg tatgatgctg tccttgacag aaatgtggcc attaagaagc tcagcagacc    360
ctttcagaac caaacacatg ccaagagagc gtaccgggag ctggtcctca tgaagtgtgt    420
gaaccataaa acattatta gtttattaaa tgtcttcaca ccccagaaaa cgctggagga    480
gttccaagat gtttacttag taatggaact gatggatgcc aacttatgtc aagtgattca    540
gatggaatta gaccatgagc gaatgtctta cctgctgtac caaatgttgt gtggcattaa    600
gcacctccat tctgctggaa ttattcacag ggatttaaaa ccaagtaaca ttgtagtcaa    660
gtctgattgc acattgaaaa tcctggactt tggactggcc aggacagcag gcacaagctt    720
catgatgact ccatatgtgg tgacacgtta ttacagagcc cctgaggtca tcctggggat    780
gggctacaag gagaacgtgg atatatggtc tgtgggatgc attatgggag aaatggttcg    840
ccacaaaatc ctctttccag gaagggacta tattgaccag tggaataagg taattgaaca    900
actaggaaca ccatgtccag aattcatgaa gaaattgcaa cccacagtaa gaaactatgt    960
```

-continued

```
ggagaatcgg cccaagtatg cgggactcac cttccccaaa ctcttcccag attccctctt    1020
cccagcggac tccgagcaca ataaactcaa agccagccaa gccagggact tgttgtcaaa    1080
gatgctagtg attgacccag caaaagaat atcagtggac gacgccttac agcatcccta     1140
catcaacgtc tggtatgacc cagccgaagt ggaggcgcct ccacctcaga tatatgacaa    1200
gcagttggat gaaagagaac acacaattga agaatggaaa gaacttatct acaaggaagt    1260
aatgaattca gaagaaaaga ctaaaaatgg tgtagtaaaa ggacagcctt ctccttcagg    1320
tgcagcagtg aacagcagtg agagtctccc tccatcctcg tctgtcaatg acatctcctc    1380
catgtccacc gaccagaccc tggcatctga cactgacagc agcctggaag cctcggcagg    1440 accccctgggt tgttgcaggt gactagccgc ctgcctgcga acccagcgt tcttcaggag    1500 atgat                                                                1505
```

<210> SEQ ID NO 103

<400> SEQUENCE: 103

000

<210> SEQ ID NO 104
<211> LENGTH: 2622
<212> TYPE: DNA
<213> ORGANISM: Rattus norvegicus

<400> SEQUENCE: 104

```
tgtatgacac tacatcatga gtgacagtaa aagcgatggc cagttttaca gtgtgcaagt      60
ggcagactca actttcactg ttctaaaacg ttaccagcag ttgaaaccaa ttggctctgg     120
agcccaagga attgtttgtg ctgcttttga tacagttctt ggaataaatg ttgctgtcaa     180
gaagttaagt cgtccttttc agaaccaaac gcatgcaaag agagcctacc gtgaacttgt     240
cctcctaaag tgtgtcaatc ataaaaatat aattagcttg ttaaatgtgt tcacaccaca     300
aaaaacgcta gaagaattcc aagatgtgta cttggttatg gagttaatgg acgctaactt     360
atgtcaggtt attcatatgg agctggacca tgaaagaatg tcatacctcc tctaccagat     420
gctttgtggc attaagcacc tgcattcagc tggcataatt catagggatt tgaagcctag     480
caacattgta gtaaaatcag actgtactct caagatcctt gactttggcc tggcacggac     540
agcctgtacc aactttatga tgactcccta tgtggtaact cgctactatc gggctccaga     600
agtcatcctg ggcatgggct acaaggagaa tgtggacatc tggtctgtcg ggtgcatcat     660
ggcagaaatg gtcctccata atcctgttc cccaggaaga gactatattg atcaatggaa     720
taaagttatt gaacagctag gaacaccatc cgcagagttc atgaagaaac ttcagccaac     780
tgtaaggaat tatgtggaaa acagaccaaa gtaccctgga atcaaatttg aagagctctt     840
tccagattgg atatttccgt cagaatccga acgagacaaa ataaaaacaa gtcaagccag     900
agatctgtta tcgaaaatgt tagtgattga tccggacaag cggatctctg tggacgaagc     960
cttgcgccac ccgtatatta ctgtttggta tgaccccgct gaagcagaag cgccaccacc    1020
tcaaatttat gatgcccagt tggaagaaag agagcatgcg attgaagagt ggaaagaact    1080
aatttacaaa gaagtgatgg actgggaaga agaagcaag aatggggtga agaccagcc      1140 ttcagatgca gcagtaagca gcaaggctac tccttctcag tcgtcatcca tcaatgacat    1200
ctcatccatg tccactgagc acacctggc ctcagacaca gacagcagtc tcgatgcctc     1260
aaccggaccc ctggaaggct gccgatgaaa cctcgcagat ggcgcacttg tctgtgaagg    1320
actctggctt ccatggccct gagcacatgg gagctggtgg aacaaatcaa gaagctccat    1380
```

```
gttctgcatg taagaaacac gacgccttgc ccccactcag ttccagtagg attgcctgcg    1440
tagactgtaa catgaggcag acgatgtctg gagaaaaagt acaaaccaca ctgttagaaa    1500
ttttgttcaa gatcattcag gtgagcaatt agaatagccg agttcttttc aagtcgtgtg    1560
gtgtccttgg tgacagatca tgtgtaactg tggggactcg tatgcatgtg accacaaatg    1620
cttgcttgaa cttgcccatg tagcactttg ggaatcagta tttaaatgcc aaataatctt    1680
ccaggtagtt ctgcttctag aataatctct taatcctctt tagtaatttg gtgtctgtcc    1740
acaaaaaaat agattatgtg tgtatgaatt ggccactatc atattatcat attttaccca    1800
cttttatggt atgattttat ctgtcttttg tatttcagaa ggaatataat taaatttatt    1860
taataaataa aactacagct tttcttaaat ttgtgatgtt ttaggctgag aattaccact    1920
gctttatatc gacactctgt gtcctttaaa ctgcccacta tgggaaactt tacgtacagc    1980
tttctgcatg acaaagttcc aagttgtatt tcactctgct taacgactta tgtcaccttg    2040
aatcctgacc acacatttcc tttttcttgg tcctctgaac ttggatctag aatccctcac    2100
agaacttcac cttctttatc acaaagcacc ccatctcagt agaatgaatc ggcagattcc    2160
tgagccccgc tgcctaatgt agagctgaca gggtggcttc cccagaacgg tgggtgggtg    2220
catccttccc tgagcccacc catcctttgc tcccctctct ttatttaagg tgaaaggtga    2280
ttgggtctca tagcctttcc ttttgtagca ttgcctaact tgtctttctc actgacagaa    2340
gccaccacgt ccagccagag cacatggtct cttaggagac cgggcttact taccatgcat    2400
gtttgctgct gtccttttcc attttgtgga ggcatttcct ttttctaagg gaattcctca    2460
gatgttctag aaacattcag aagaacgcag aagaaatatt ctagagaatt ggggttcat    2520 tcttgaatat tttctgattt aaaactgctc acctgaaatt gatactttca gatcctgatc    2580
ttgtaaatta ctcgagattt ggtaagatgc tgagttctct gt                      2622
```

<210> SEQ ID NO 105

<400> SEQUENCE: 105

000

<210> SEQ ID NO 106
<211> LENGTH: 1646
<212> TYPE: DNA
<213> ORGANISM: Mus musculus

<400> SEQUENCE: 106

```
gctgttagtc agcggagcgg ccgaggccgg acgttgcggc cgaaacgcgg agccgcgaac      60
aggattgagt agcggccgcg gccaccgcag gacggcgccg ttctccgcta cgggcttcca     120
ggtcgccgtt ggctgcactg ccggccttgg tgaatatttg gatgaagcca ttagactaat     180
tgcttgccat catgagcaga agcaaacgtg acaacaattt ttatagtgta gagattggag     240
attctacatt cacagtccta aaacgatacc agaatttaaa gcctataggc tcaggagctc     300
aaggaatagt gtgtgcagct tatgatgcca ttcttgaaag aaatgttgca atcaagaagc     360
tcagccggcc atttcagaat cagacccatg ctaagcgcgc ctaccgagaa ctagttctta     420
tgaagtgtgt taatcacaaa aatataattg gccttttgaa tgttttcaca ccacagaaat     480
ccctagaaga atttcaagat gtttacatag tcatggagct catggatgca aatctttgcc     540
aagtgattca gatggagtta gatcatgaaa gaatgtccta ccttctctat caaatgctgt     600
gtggaatcaa gcaccttcac tctgctggaa ttattcatcg ggacttaaag cctagtaata     660
tagtagtcaa atcagactgc actttgaaga ttcttgattt tggactggcg aggactgcag     720
```

```
gaacgagttt tatgatgacg ccttatgtgg tgactcgcta ctacagagca ccagaggtca    780
ttctcggcat gggctacaag gagaacgtgg acttatggtc tgtggggtgc attatgggag    840
aaatggtttg ccacaaaatc ctcttccag gaagggacta tattgatcag tggaataaag     900
ttattgaaca gctcggaaca ccttgtcctg aattcatgaa gaaactacaa ccaacagtaa    960
ggacttatgt tgaaaacagg cctaaatacg ctggatatag ctttgagaaa ctgttccccg   1020
atgtgctttt cccagctgac tcagagcata acaaacttaa agccagtcag gcaagagatt   1080
tgttatccaa aatgctagta atagatgcat ccaaaaggat ctccgtagat gaagctctcc   1140
agcacccata catcaacgtc tggtatgatc cttcagaagc agaagcccca ccaccaaaga   1200
tcccggacaa gcagttagat gagagggagc acacaataga ggagtggaaa gaactgatat   1260
acaaggaggt aatggatttg gaggaacgaa ctaagaatgg agtcataaga gggcagccgt   1320
ctcctttagc acaggtgcag caatgatcaa tggctctcag catccatcgt cttcgccgtc   1380
tgtcaatgac atgtcttcaa tgtccacaga tccgactttg gcctcggata cagacagcag   1440
tctagaagca tcagctggac ctctgggctg ctgtagatga ctacttgggc cttgggtggg   1500
tgggagggat ggggaattgg ttagtcattg atagaactgc tttaaaaaca attcagtggt   1560
catatttttg agtgattttt cagaaaatgt agaattcatt ttgtagtaaa gtagtttatt   1620 tttttaatt tcaagtgttg taattc                                         1646
```

<210> SEQ ID NO 107
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 107
ccttccctga aggttcctcc                                                 20

<210> SEQ ID NO 108
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 108
tgttgtcacg tttgcttctg                                                 20

<210> SEQ ID NO 109

<400> SEQUENCE: 109

000

<210> SEQ ID NO 110

<400> SEQUENCE: 110

000

<210> SEQ ID NO 111
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 111
caacgtcccg cgctcggccg                                              20

<210> SEQ ID NO 112
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 112
cctgctcgcg gctccgcgtt                                              20

<210> SEQ ID NO 113
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 113
ctcatgatgg caagcaatta                                              20

<210> SEQ ID NO 114
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 114
tgttgtcacg tttacttctg                                              20

<210> SEQ ID NO 115
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 115
cggtaggctc gcttagcatg                                              20

<210> SEQ ID NO 116
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 116
ctagggattt ctgtggtgtg                                              20

<210> SEQ ID NO 117
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 117
cagcagagtg aaggtgcttg                                              20
```

<210> SEQ ID NO 118
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 118
tcgttcctgc agtccttgcc                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 119
ccatttctcc cataatgcac                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 120
tgaattcagg acaaggtgtt                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 121
agcttcgtct acggagatcc                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 122
cactcctcta ttgtgtgctc                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 123
gctgcaccta aaggagacgg                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic Oligonucleotide

```
<400> SEQUENCE: 124
ccagagtcgg atctgtggac                                              20

<210> SEQ ID NO 125
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 125
tcatgatgta gtgtcataca                                              20

<210> SEQ ID NO 126
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 126
tgtggtgtga acacatttaa                                              20

<210> SEQ ID NO 127
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 127
ccatatgaat aacctgacat                                              20

<210> SEQ ID NO 128
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 128
gatatcaaca ttctccttgt                                              20

<210> SEQ ID NO 129
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 129
gcttcgtcca cagagatccg                                              20

<210> SEQ ID NO 130
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 130
gctcagtgga catggatgag                                              20
```

```
<210> SEQ ID NO 131
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 131
atctgcgagg tttcatcggc                                               20

<210> SEQ ID NO 132
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 132
ccaccagctc ccatgtgctc                                               20

<210> SEQ ID NO 133
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 133
cagttacaca tgatctgtca                                               20

<210> SEQ ID NO 134
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 134
aagaggatta agagattatt                                               20

<210> SEQ ID NO 135
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 135
agcagagtga aatacaactt                                               20

<210> SEQ ID NO 136
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 136
tgtcagctct acattaggca                                               20

<210> SEQ ID NO 137
<211> LENGTH: 20
<212> TYPE: DNA
<213> ORGANISM: Artificial Sequence
<220> FEATURE:
<223> OTHER INFORMATION: Synthetic Oligonucleotide
```

<400> SEQUENCE: 137
agtaagcccg gtctcctaag                                                 20

<210> SEQ ID NO 138
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 138
aaatggaaaa ggacagcagc                                                 20

<210> SEQ ID NO 139
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 139
gctcagtgga tatggatgag                                                 20

<210> SEQ ID NO 140
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 140
gctaagcggt caaggttgag                                                 20

<210> SEQ ID NO 141
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 141
gctcggtgga aatggatcag                                                 20

<210> SEQ ID NO 142
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 142
gggctttcat tagccacatt                                                 20

<210> SEQ ID NO 143
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 143
ggttggttca ctgcagtagt                                                 20

```
<210> SEQ ID NO 144
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 144
tgctcatgtt gtaatgtttg                                               20

<210> SEQ ID NO 145
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 145
gtcgaggaca gcgtcatacg                                               20

<210> SEQ ID NO 146
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 146
cgacatccgc tcgtggtcca                                               20

<210> SEQ ID NO 147
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 147
acatacggag tcatcatgaa                                               20

<210> SEQ ID NO 148
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 148
gcaatttctt catgaattct                                               20

<210> SEQ ID NO 149
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 149
tcgtaccaaa cgttgatgta                                               20

<210> SEQ ID NO 150
<211> LENGTH: 20
<212> TYPE: DNA
<213> ORGANISM: Artificial Sequence
<220> FEATURE:
<223> OTHER INFORMATION: Synthetic Oligonucleotide
```

-continued

```
<400> SEQUENCE: 150
cgccgaggct tccaggctgc                                              20

<210> SEQ ID NO 151
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 151
ggctagtcac ctgcaacaac                                              20

<210> SEQ ID NO 152
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 152
gcgtgcgtgc gtgcttgcgt                                              20

<210> SEQ ID NO 153
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 153
gctcagctgc gatacagaac                                              20

<210> SEQ ID NO 154
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 154
agcgcgacta gaagttaagt                                              20

<210> SEQ ID NO 155
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 155
agggagacca aagtcgagcg                                              20

<210> SEQ ID NO 156
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 156
acatcttgaa attcttctag                                              20
```

```
<210> SEQ ID NO 157
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 157
taggatattc tttcatgatc                                               20

<210> SEQ ID NO 158
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 158
agaaggtagg acattctttc                                               20

<210> SEQ ID NO 159
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 159
tttattccac tgatcaatat                                               20

<210> SEQ ID NO 160
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 160
tcaataactt tattccactg                                               20

<210> SEQ ID NO 161
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 161
ggttgcagtt tcttcatgaa                                               20

<210> SEQ ID NO 162
<211> LENGTH: 20
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 6
<223> OTHER INFORMATION: n = I

<400> SEQUENCE: 162
tagganattc tttcatgatc                                               20

<210> SEQ ID NO 163
<211> LENGTH: 20
<212> TYPE: DNA
<213> ORGANISM: Artificial Sequence
```

```
<220> FEATURE:
<223> OTHER INFORMATION: Synthetic Oligonucleotide
<220> FEATURE:
<221> NAME/KEY: misc_feature
<222> LOCATION: 8
<223> OTHER INFORMATION: n = I

<400> SEQUENCE: 163
ggttgcantt tcttcatgaa                                                   20
```